US007972615B2

(12) United States Patent
Orgambide et al.

(10) Patent No.: US 7,972,615 B2
(45) Date of Patent: *Jul. 5, 2011

(54) PEPTIDE COMPOSITIONS FOR COATING METAL MEDICAL DEVICES WITH VANCOMYCIN

(75) Inventors: Guy Orgambide, Morrisville, NC (US); Mohmed Anwer, Cary, NC (US); Shrikumar A. Nair, Cary, NC (US); Paul Hamilton, Cary, NC (US)

(73) Assignee: Affinergy, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/413,285

(22) Filed: Mar. 27, 2009

(65) Prior Publication Data

US 2009/0246251 A1 Oct. 1, 2009

Related U.S. Application Data

(60) Provisional application No. 61/039,946, filed on Mar. 27, 2008.

(51) Int. Cl.

| | |
|---|---|
| ***A61F 13/00*** | (2006.01) |
| ***A61K 38/00*** | (2006.01) |
| ***A61K 38/10*** | (2006.01) |
| ***A61K 38/08*** | (2006.01) |
| ***A61K 38/28*** | (2006.01) |
| ***A61K 38/16*** | (2006.01) |
| ***A61K 38/04*** | (2006.01) |

(52) U.S. Cl. ....... 424/422; 514/1.1; 514/21.3; 514/21.4; 514/21.5; 514/21.6; 514/21.7; 514/21.8; 530/300; 530/304; 530/324; 530/326; 530/327; 530/328; 530/329

(58) Field of Classification Search ........................ None
See application file for complete search history.

(56) References Cited

U.S. PATENT DOCUMENTS

| | | | | |
|---|---|---|---|---|
| 5,070,156 | A | 12/1991 | Feldman | |
| 5,760,176 | A | 6/1998 | Pierschbacher | |
| 6,428,579 | B1 * | 8/2002 | Valentini | 623/23.76 |
| 7,030,093 | B2 | 4/2006 | Vogt | |
| 2003/0108743 | A1 | 6/2003 | Anderson | |
| 2004/0106544 | A1 | 6/2004 | Cooper | |
| 2005/0064431 | A1 | 3/2005 | Leon | |
| 2005/0260275 | A1 * | 11/2005 | Patt | 424/490 |
| 2006/0263830 | A1 | 11/2006 | Grinstaff | |
| 2007/0041904 | A1 | 2/2007 | Jiang | |
| 2007/0269369 | A1 | 11/2007 | Gegg | |

FOREIGN PATENT DOCUMENTS

WO 2006007368 * 1/2006

OTHER PUBLICATIONS

Written Opinion for the International Searching Authority for PCT/US09/38573, Jun. 15, 2009.

* cited by examiner

*Primary Examiner* — Shulamith H Shafer
(74) *Attorney, Agent, or Firm* — Laura L. Kiefer

(57) ABSTRACT

The presently disclosed subject matter provides compositions comprising a first substrate-binding domain (a peptide or a polymer) having binding affinity for a tissue or a medical device, a second substrate-binding domain having binding affinity for a target molecule, and the target molecule. In some embodiments, the first and second substrate-binding domains are covalently linked. The first and second substrate-binding domains are covalently coupled to at least one hydrophobic interaction tag, negatively charged interaction tag, or positively charged interaction tag. When the substrate-binding domains are combined and coated onto the tissue or medical device, the hydrophobic interaction tags interact with each other and the charged interaction tags interact with the oppositely charged interaction tags or the oppositely charged substrate binding polymers, to form a macromolecular network of non-covalently coupled substrate-binding domains to load the target molecule onto the tissue or medical device.

8 Claims, 6 Drawing Sheets

PEPTIDE COMPOSITIONS FOR COATING METAL MEDICAL DEVICES WITH VANCOMYCIN

CROSS REFERENCE TO RELATED APPLICATIONS

The presently disclosed subject matter claims the benefit of U.S. Provisional Patent Application Ser. No. 61/039,946 filed Mar. 27, 2008; the disclosure of which is herein incorporated by reference in its entirety.

GRANT STATEMENT

This invention was made in part from government support under Grant No. 2R44AR051264-02 from the National Institute of Arthritis and Musculoskeletal and Skin Diseases. Thus, the U.S. Government has certain rights in the invention.

FIELD OF THE INVENTION

The presently disclosed subject matter relates to compositions comprising macromolecular networks comprised of non-covalently coupled substrate binding domains for loading of a target molecule to a tissue or medical device.

BACKGROUND OF THE INVENTION

To provide an efficacious dose of a therapeutic agent at the site of treatment, systemic administration of the therapeutic can often lead to adverse or toxic side effects to the patient. Local delivery provides smaller total amounts of the therapeutic minimizing adverse side effects and targets the therapeutic to the site of treatment. One way to locally deliver a therapeutic agent to a treatment site is to coat the therapeutic agent onto the surface of an implantable medical device.

Many matrix systems have been developed to deliver a bioactive molecule to a substrate, such as the surface of a medical device. Typically, the bioactive molecule is covalently coupled to the substrate, or more commonly, the substrate is coated with a matrix containing bioactive molecule. The matrix may be composed of a polymer into which is trapped the bioactive molecule, and as the matrix degrades, released is the bioactive molecule. Thus, the efficiency of release of the bioactive molecule from the polymer matrix depends on individual matrix characteristics such as the affinity of the matrix for the bioactive molecule; and the matrix degradation rate, density, and pore size. Typically, materials used in such matrix systems include polymers such as polylactides, polyglycolides, polyanhydrides, polyorthoesters, polylactic and polyglycolic acid copolymers, alginate, poly (ethylene glycol), polyoxyethylene oxide, carboxyvinyl polymer, and poly(vinyl alcohol). Natural matrix proteins/polymers used to encapsulate entrap bioactive molecules for release include collagen, glycosaminoglycans, and hyaluronic acid, which are enzymatically digested in the body.

Recently described are biological coating compositions for medical devices (see, e.g., published patent applications US 20060051395, US 20070160644, co-pending and commonly owned) comprising a biofunctional composition. The biofunctional composition comprises a peptide having binding specificity for a surface material comprising the surface onto which is to be applied the coating composition, and a peptide having binding specificity for a therapeutic agent; wherein covalently coupled are the peptide having binding specificity for a surface material and the peptide having binding specificity for a therapeutic agent. The coating composition may further comprise therapeutic agent non-covalently bound to peptide having binding specificity for the therapeutic agent. Peptide-based biomaterials have gained interest as novel materials for biomedical applications (see Fairman R. Akerfeldt K S. *Curr Opin Struct Biol* 2005; 15 (4): 453-63 and Rajagopal K, Schneider J P. *Curr Opin Struct Biol* 2004; 14 (4): 480-6). A large variety of synthetic advantages of peptide-based biomaterials include their programmability, biodegradability, and bioresorbability. In addition, peptides can be isolated that bind to specific therapeutic agents or the surface of biomaterials (Grinstaff et al. U.S. Patent Application 20060263830; Beyer et al. U.S. Patent Application 20060051395).

Certain peptides are able to self assemble into gel like membranes when incubated in the presence of low concentrations of monovalent cations (U.S. Pat. Nos. 5,670,483; 6,548,630) or based on the spatial matching of the complementary functional groups (U.S. Pat. No. 7,399,831). Versatile side-chain functional groups and non-covalent interactions of 20 amino acids enable one to design peptides for numerous applications. Most designed peptide-based biomaterials are amphipathic, with both hydrophilic and hydrophobic amino acids in their sequence. The order and repeat of these amino acids in the primary sequence determines the nature of the secondary structure adopted by these peptides and, thereby, the final morphology of the assembled biomaterials. Assembly of these peptides is driven by the non-covalent interactions between the side-chain functional groups and backbone amides, which mostly involve hydrophobic, electrostatic, hydrogen bonding, and π-stacking interactions (Ramachandran, S. Yu, Y. B. *Biodrugs* 2006; 20 (5): 263-269). Designed proteins offer favorable properties such as precision and tight regulation of self assembly by using environmental cues such as pH, ionic strength and temperature (Whitesides, et al. (1991) *Science* 254, 1312-1319; Yeates, T. O. & Padilla, J. E. (2002) *Curr. Opin. Struct. Biol.* 12, 464-470; MacPhee, C. E., Woolfson, D. N. (2004) *Curr. Opin. Solid State Mater.* 8, 141-149).

Nature forms complex multicomponent three-dimensional structures through spontaneous association of molecules termed "molecular self-assembly" (Whitesides, et al. (1991) *Science* 254, 1312-1319). The self-assembly process is mediated through weak intermolecular bonds, such as van der waals bonds, electrostatic interactions, hydrogen bonds and stacking interactions. These relatively low energy interactions are combined together to form intact and well-ordered supramolecular structures. The self-assembly of peptide amphiphiles into nanostructures creates a dense hydrocarbon-like microenvironment within an aqueous gel. The environment created locally upon assembly makes peptide amphiphile nanostructures and other self-assembling systems potentially ideal candidates for the delivery of hydrophobic or water-insoluble molecules in vivo (Guler, et al. *J Mater Chem* 2005,15, 4507-4512). In addition, peptide sequences that bind to cells or other biologics can be attached to self-assembling peptides to generate peptide nanofibers that bind biologics (U.S. Pat. No. 7,399,831; U.S. Patent Application 20050272662; U.S. Patent Application 20050209145).

Within the art, however, there still exists a need to generate self-assembling peptides that both bind a therapeutic agent and to the surface of a medical device. These dual functional, self-assembling peptides could be used for controlled, local deliver of a therapeutic agent from an implanted medical device.

SUMMARY OF THE INVENTION

The presently disclosed subject matter provides a composition comprising a plurality of a first substrate-binding peptide comprising 3 to 40 amino acids, wherein the first substrate is a tissue or a medical device and the first substrate-binding peptide has binding affinity for the tissue or the medical device; a plurality of a second substrate-binding peptide comprising of 3 to 40 amino acids, wherein the second substrate is a target molecule and the second substrate-binding peptide has binding affinity for the target molecule, wherein the first and second substrate-binding peptides are not covalently linked; and a plurality of the target molecule; wherein each of the first and second substrate-binding peptides is covalently coupled to at least one interaction tag selected from the group consisting of a hydrophobic interaction tag, a positively charged interaction tag, and a negatively charged interaction tag, wherein the hydrophobic interaction tags interact with each other and the positively charged interaction tags interact with the negatively charged interaction tags to form a macromolecular network comprising the plurality of non-covalently coupled first and second substrate-binding peptides.

In another embodiment, the presently disclosed subject matter provides a composition comprising a plurality of a first substrate-binding polymer having a net negative or a net positive charge, wherein the first substrate is a tissue or medical device and the first substrate-binding polymer has binding affinity for the tissue or medical device; a plurality of a second substrate-binding peptide of 3 to 40 amino acids, wherein the second substrate is a target molecule and the second substrate-binding peptide has binding affinity for the target molecule, wherein the first substrate-binding polymer and the second substrate-binding peptide are not covalently linked; and a plurality of the target molecule, wherein the plurality of second substrate-binding peptides are covalently coupled to at least one net positively or net negatively charged interaction tag, wherein the charge of the interaction tag is opposite to the charge of the first substrate-binding polymer, wherein each of the plurality of first substrate-binding polymers and second substrate-binding peptides is optionally covalently coupled to a hydrophobic interaction tag, wherein the charged interaction tag interacts with the first substrate-binding polymer and the optional hydrophobic interaction tags interact with each other to form a macromolecular network comprising the plurality of non-covalently coupled first substrate-binding polymers and second substrate-binding peptides.

In another embodiment, the presently disclosed subject matter provides a composition comprising a plurality of a first substrate-binding peptide comprising 3 to 40 amino acids, wherein the first substrate is a tissue or medical device and the first substrate-binding peptide has binding affinity for the tissue or medical device; a plurality of a second substrate-binding peptide comprising 3 to 40 amino acids, wherein the second substrate is a target molecule and the second substrate-binding peptide has binding affinity for the target molecule, wherein the first and second substrate-binding peptides are covalently linked; and a plurality of the target molecule, wherein the plurality of covalently linked first and second substrate-binding peptides are covalently coupled to at least one interaction tag selected from the group consisting of a hydrophobic interaction tag, a positively charged interaction tag, and a negatively charged interaction tag, wherein the hydrophobic interaction tags interact with each other and the positively charged interaction tags interact with the negatively charged interaction tags to form a macromolecular network comprising the plurality of non-covalently coupled substrate-binding peptides.

In another embodiment, the presently disclosed subject matter provides a composition comprising a composition comprising, a plurality of first molecules comprising a first substrate-binding peptide comprising 3 to 40 amino acids, wherein the first substrate is a tissue or medical device and the first substrate-binding peptide has binding affinity for the tissue or medical device; and a second substrate-binding peptide comprising 3 to 40 amino acids, wherein the second substrate is a target molecule and the second substrate-binding peptide has binding affinity for the target molecule, wherein the first and second substrate-binding peptides are covalently linked; and a plurality of second molecules comprising the second substrate-binding peptide, wherein the second substrate binding peptide is not covalently linked to the first substrate binding peptide; and a plurality of the target molecule, wherein each of the plurality of first and second molecules are covalently coupled to at least one interaction tag selected from the group consisting of a hydrophobic interaction tag, a positively charged interaction tag, and a negatively charged interaction tag, wherein the hydrophobic interaction tags interact with each other and the positively charged interaction tags interact with the negatively charged interaction tags to form a macromolecular network comprising the plurality of non-covalently coupled first and second molecules.

In another embodiment, the presently disclosed subject matter provides methods for coating a tissue or a medical device with the presently disclosed compositions, and medical devices, wherein at least a portion of the medical device is coated with a composition of the presently disclosed subject matter.

BRIEF DESCRIPTION OF THE DRAWINGS

FIG. 4A shows a composition comprising a first substrate-binding peptide (SBD-1) having 2 covalently coupled positively charged interaction tags (+++) (far left) associating through electrostatic interactions with a second substrate-binding peptide (SBD-2) having 1 covalently coupled negatively charged interaction tag (−−−) (left, and association shown in the middle). The diagram further shows how a multitude of the first and second substrate binding domains associate together (far right). FIG. 4B shows a composition comprising a first substrate-binding peptide having 1 covalently coupled positively charged interaction tag and 1 covalently coupled hydrophobic interaction tag (zig zag line) (far left) associating through electrostatic interactions with a second substrate-binding peptide having 1 covalently coupled negatively charged interaction tag (left, and association shown in the middle). The diagram further shows how a multitude of the first and second substrate binding domains associate together through both the charged interaction tags and the hydrophobic interaction tags (far right). FIG. 4C shows a composition comprising a first substrate-binding peptide having 1 covalently coupled positively charged interaction tag and 1 covalently coupled hydrophobic interaction tag (far left) associating through electrostatic and hydrophobic interactions with a second substrate-binding peptide having 1 covalently coupled negatively charged interaction tag and 1 covalently coupled hydrophobic interaction tag (left, and association shown in the middle). The diagram further shows how a multitude of the first and second substrate binding domains associate together through both the charged interaction tags and the hydrophobic interaction tags (far right).

FIG. 5A shows a composition comprising a first substrate-binding polymer (SBD-1) having a positive charge (far left) associating through electrostatic interactions with a second substrate-binding peptide (SBD-2) having 1 covalently coupled negatively charged interaction tag (−−−) (left, and association shown in the middle). The diagram further shows how a multitude of the first and second substrate binding domains associate together (far right). FIG. 5B shows a composition comprising a first substrate-binding polymer having 1 covalently coupled hydrophobic interaction tag (zig zag line) (far left) associating through electrostatic interactions with a second substrate-binding peptide having 1 covalently coupled negatively charged interaction tag (left, and association shown in the middle). The diagram further shows how a multitude of the first and second substrate binding domains associate together through both the charged interaction tags and the hydrophobic interaction tags (far right). FIG. 5C shows a composition comprising a first substrate-binding polymer having 1 covalently coupled hydrophobic interaction tag (far left) associating through electrostatic and hydrophobic interactions with a second substrate-binding peptide having 1 covalently coupled negatively charged interaction tag and 1 covalently coupled hydrophobic interaction tag (left, and association shown in the middle). The diagram further shows how a multitude of the first and second substrate binding domains associate together through both the charged interaction tags and the hydrophobic interaction tags (far right).

FIG. 6A shows a composition starting with 2 molecules of a first substrate-binding peptide (SBD-1) covalently linked to a second substrate binding peptide (SBD-2), wherein the peptides are covalently linked together through a hydrophobic interaction tag (zig zag line) and there is a further covalently coupled positively charged interaction tag (+++) on 1 of the molecules and a negatively charged interaction tag (−−−) on the other molecule (far left). The middle shows an association of the 2 molecules through both electrostatic interactions of the charged interaction tags and hydrophobic interactions of the hydrophobic interaction tags. The diagram further shows (far right) how a multitude of the molecules comprising first and second substrate binding domains and charged and hydrophobic tags associate together. FIG. 6B shows a composition starting with 2 molecules of a first substrate-binding peptide covalently linked to a second substrate binding peptide, wherein the peptides are covalently linked together through a linker (L) and each of the molecules further comprise a covalently coupled hydrophobic interaction tag (far left). The middle shows an association of the 2 molecules through hydrophobic interactions of the hydrophobic interaction tags. The diagram further shows (far right) how a multitude of the molecules comprising first and second substrate binding domains and hydrophobic tags associate together.

FIG. 7 (far left) shows a first top left molecule of a first substrate-binding peptide (SBD-1) covalently linked to a second substrate binding peptide (SBD-2), wherein the peptides are covalently linked together through a hydrophobic interaction tag (zig zag line) and there is a further positively charged interaction tag covalently coupled to the SBD-1 (+++). A second molecule on the bottom far left having a second substrate binding peptide (SBD-2) with a covalently coupled negatively charged interaction tag (−−−) is shown to interact with the first molecule through electrostatic interactions of the charged interaction tags (middle). The diagram further shows (far right) how a multitude of the molecules comprising first and second substrate binding domains and charged and hydrophobic interaction tags associate together.

DETAILED DESCRIPTION OF THE INVENTION

Figure 1:
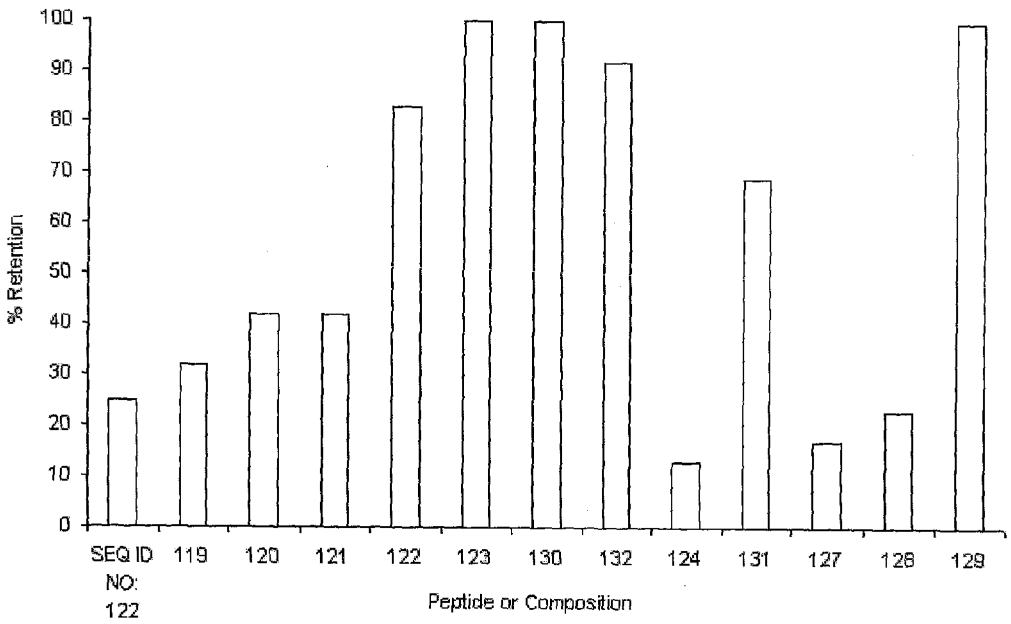
FIG. 1 is a bar graph measuring the retention of substrate-binding peptide by itself (e.g., SEQ ID NO:122) or as coupled to a molecule for promoting self assembly (e.g., conjugates, or compositions 119-124, 127-132; see Example 6 herein for a description of both) to a substrate in assay conditions which mimic the presence of human plasma.

Definition Section While the following terms are believed to be well understood by one of ordinary skill in the art, the following definitions are set forth to facilitate explanation of the invention. Also, additional definitions may be provided in the specification outside of this "Definition Section" to facilitate explanation of the invention.

The term "macromolecular network" is used herein, for purposes of the specification and claims, to mean a structure formed by a plurality of molecules of compound, wherein the structure is formed by non-covalent molecular interactions between fatty acid molecules of the plurality of molecules of compound, resulting in a molecular association between ("linking") two or more molecules of compound together. It is intended to be clear that the use of the term "linking" in this specific instance is referring to a non-covalent molecular association between the fatty acid molecules of two or more molecules of compound, and should not be confused with use of the term "linking" in other places throughout the presently disclosed specification and claims where the term is used to refer to a covalent bond. The macromolecular network, when applied to a substrate, may form at least a monolayer (a layer that is at least one molecule of compound in thickness). Whether a monolayer or multilayer (more than a monolayer) is formed depends on such factors as the number of fatty acids per substrate-binding peptide in each compound, external factors of the surrounding environment (pH, hydrophobicity), concentration of compound (e.g., how many molecules of compound are added together, and relative to the chance of interaction between fatty acid components of individual compounds), and the like. Non-covalent molecular interactions between two or more fatty acid molecules that may contribute to formation of the macromolecular network include one or more of, but are not limited to, hydrogen bonding, van der Waals interactions, hydrophobic interactions, and electrostatic interactions.

The terms "first" and "second" are used herein for purposes of the specification and claims for ease of explanation in differentiating between two different molecules, and are not intended to be limiting the scope of the present invention, nor imply a spatial, sequential, or hierarchical order unless otherwise specifically stated.

The term "non-biological substrate" is used herein for purposes of the specification and claims to mean a substrate that is not a quality or component of a living system. A non-biological substrate can comprise any form suitable to its intended use including, but not limited to, a container, reactor, device, array, medical device, particle (e.g., microparticle, nanoparticle, and the like), a surface of a non-biological substrate, a diagnostic agent, a drug (e.g., synthesized small molecule drug), a chemical catalyst, a formulation, and a combination thereof. Representative non-biological substrates include, but are not limited to, plastic, silicon, synthetic polymer, metal (including mixed metal alloys), metal oxide (e.g., glass), non-metal oxide, ceramic, carbon-based materials (e.g., graphite, carbon nanotubes, carbon "buckyballs", and metallo-carbon composites), and combinations thereof. In addition to medical devices, as described more in detail herein, other non-biological substrates that may benefit from the present invention include, but are not limited to, (a) medical supplies, such as bandages, dressings, sponges, covers, and the like; (b) laboratory equipment, such as bioreactors, fermentors, test tubes, assay plates, arrays, culture containers, and the like; and (c) packaging or product protection (e.g., packaging materials, coverings (such as wraps)), such as applied to perishables such as foods, drugs, and medical devices. Diagnostic agents include, but are not limited to, radiolabels, radiopaque compounds, calorimetric reagents, dyes, fluorophores, fluorescent molecules, fluorescent nanocrystals, luminescent molecules, chromophores, and the like. Catalysts can be selected from the group consisting of heterogeneous catalysts, homogeneous catalysts, biocatalysts (e.g., enzymes in metabolic or biological pathways), electrocatalysts (e.g., metal-rich catalysts used in fuel cells, or energy generation), organocatalysts (simple organic molecules used as catalysts in chemical reactions), as known to those skilled in the art. A preferred non-biological substrate may be used in accordance with the present invention to the exclusion of a non-biological substrate other than the preferred non-biological substrate.

The term "metal" is used herein for purposes of the specification and claims to mean one or more compounds or compositions comprising a metal represented in the Periodic Table (e.g., a transition metal, alkali metals, and alkaline earth metals, each of these comprise metals related in structure and function, as classified in the Periodic Table), and may further refer to a metal alloy, a metal oxide, a silicon oxide, and bioactive glass. Examples of preferred metals include, but are not limited to, titanium, titanium alloy, stainless steel, aluminum, zirconium alloy metal substrate (e.g., Oxinium™), cobalt chromium alloy, gold, silver, rhodium, zinc, tungsten, platinum, rubidium, and copper. A preferred metal may be used in accordance with the present invention to the exclusion of a metal other than the preferred metal.

The term "polymer" is used herein for purposes of the specification and claims to mean a molecule or material comprised of repeating structural units (a structural unit typically referred to as a monomer) connected by covalent chemical bonds. Depending on its intended use, a polymer may be biodegradable (e.g., one or more of self-dissolving, or bioresorbable, or degradable in vivo) or non-biodegradable; or synthetic (manufactured, and not found in nature) or natural (found in nature, as made in living tissues of plants and/or animals).

Non-limiting examples of suitable synthetic polymers described as being biodegradable include: poly-amino acids; polyanhydrides including maleic anhydride polymers; polycarboxylic acid; some polyethylenes including, but not limited to, polyethylene glycol, polyethylene oxide; polypropylenes, including, but not limited to, polypropylene glycol, polypropylene fumarate; one or more of polylactic acid or polyglycolic acid (and copolymers and mixtures thereof, e.g., poly(L-lactic acid) (PLLA), poly(D,L,-lactide), poly(lactic acid-co-glycolic acid), 50/50 (DL-lactide-co-glycolide)); polyorthoesters; polydioxanone; polyphosphazenes; polydepsipeptides; one or more of polycaprolactone (and co-polymers and mixtures thereof, e.g., poly(D,L-lactide-co-caprolactone) or polycaprolactone co-butylacrylate; polyhydroxybutyrate valerate and blends; some polycarbonates (e.g., tyrosine-derived polycarbonates and arylates), polyiminocarbonates, calcium phosphates; cyanoacrylate; some polyamides (including nylon); polyurethane; polydimethyltrimethylcarbonates; synthetic cellulosic polymers (e.g., cellulose acetate, cellulose butyrate, cellophane); and mixtures, combinations, and copolymers of any of the foregoing. Representative natural polymers described as being biodegradable include macromolecules (such as polysaccharides, e.g., alginate, starch, chitosan, cellulose, or their derivatives (e.g., hydroxypropylmethyl cellulose); proteins and polypeptides, e.g., gelatin, collagen, albumin, fibrin, fibrinogen); polyglycosaminoglycans (e.g. hyaluronic acid, chondroitin sulfate); and mixtures, combinations, and copolymers of any of the foregoing.

Non-limiting examples of suitable synthetic polymers described as being non-biodegradable include: inert polyaryletherketones, including polyetheretherketone ("PEEK"), polyether ketone, polyetherketoneketone, and polyetherketoneetherketoneketone; polyurethanes; polystyrene, and styrene-ethylene/butylene-styrene block copolymers; polyisobutylene copolymers and styrene-isobutylene-styrene block copolymers; polyvinylpyrrolidone; polyvinyl alcohols; copolymers of vinyl monomers; polyvinyl ethers; polyvinyl aromatics; polyethylene oxides; polyesters including polyethylene terephthalate; some polyamides; polyacrylamides; polyethers including polyether sulfone; polyalkylenes including polypropylene, polyethylene; copolymers of ethylene and polypropylene; some polycarbonates, silicone and silicone rubber; siloxane polymers; polytetrafluoroethylene; expanded polytetrafluoroethylene (e-PTFE); nylons and related polyamide copolymers; nylon; fluorinated ethylene propylene; hexafluroropropylene, polymethylmethacrylate (PMMA); 2-hydroxyethyl methacrylate (PHEMA); polyimides; polyethyleneterephthalate; polysulfone, and polysulfides; and mixtures, combinations, and copolymers (including cross-linked copolymers) of any of the foregoing.

The term "ceramic" is used herein for purposes of the specification and claims to mean inorganic non-metallic materials whose formation is due to the action of heat. Suitable ceramic materials include but are not limited to silicon oxides, aluminum oxides, alumina, silica, hydroxyapatites, glasses, quartz, calcium oxides, calcium phosphates, indium tin oxide, polysilanols, phosphorous oxide, and combinations thereof.

The term "effective amount" is used herein, in referring to a composition according to the present invention and for purposes of the specification and claims, to mean an amount sufficient of the composition to promote a beneficial property resulting from the compound, including but not limited to, improved biophysical properties. In the case that the composition also has binding specificity for a substrate, an "effective amount" may also comprise an amount sufficient so as to mediate binding of the composition to the substrate.

The term "individual", as used herein for purposes of the specification and claims, refers to either a human or an animal.

The terms "biological molecule" or "biological substrate" (which may sometimes be used interchangeably herein), as used herein for purposes of the specification and claims, refers to a quality or component pertaining to living systems. As such, a "biological substrate" can comprise an organ, a tissue, a cell, components or structures thereof or associated therewith, or a biological molecule. Thus, a biological substrate can comprise a biological molecule including, but not limited, to a protein (e.g., an antibody, antibody chain, avimer, collagen, keratin or other proteinaceous tissue component or structure, polypeptide, a receptor, a glycoprotein, a lipoprotein, a hormone, a growth factor, a cytokine, a chemical mediator, and the like), a peptide, a lipid, a carbohydrate (e.g., a polysaccharide, starch, monosaccharide), a nucleic acid molecule (e.g., an aptamer, DNA, RNA, hybrid nucleic acid molecule, vectors, chemically modified nucleic acid molecule), an oligomer, a small molecule (e.g., a chemical compound; metabolites, such as sugars, folic acid, uric acid, lactic acid), a drug (e.g., a biological-based drug, hormone, antimicrobial compound, growth factor, signaling molecule, ligand, etc.), a signaling molecule, a ligand, a nucleic acid-protein fusion, fragments thereof, analogs thereof, and a combination thereof. The term "biological substrate" also encompasses substrates that have been isolated from a living system, and substrates that have been recombinantly or synthetically produced based on knowledge of a biological substrate such as found in a living system, and biologically-active analogs thereof. While the origin of the biological molecule or biological substrate is preferably human, it may be originated from any biological source or organism; e.g., any animal, plant, bacteria, virus, yeast, etc. Typically, a biologically-active analog of a biological molecule has a chemical composition having from about 1% to about 25% difference, as compared to the chemical composition of the biological molecule from which the analog was derived. A preferred biological substrate or biological molecule may be used in accordance with the present invention to the exclusion of a biological substrate or biological molecule other than the preferred biological substrate or biological molecule.

The term "time sufficient for binding" generally refers to a temporal duration sufficient for specific binding of a composition to a substrate for which the composition has binding specificity, as known to those skilled in the art. For example, based on the affinity/binding specificity of a substrate-binding peptide used in a composition according to the present invention, generally a time sufficient for binding a composition according to the present invention to a substrate ranges from about 5 minutes to no more than 60 minutes.

The term "compound" is used herein, in reference to a composition of the present invention and for purposes of the specification and claims, to refer to a molecule comprising fatty acid covalently coupled to a substrate-binding peptide, either directly or via a linker. Thus, the peptide is functionalized with one or more molecules of fatty acid, the number may depend on the improved biophysical property which is desired (e.g., see Examples 6-9 herein). In one embodiment, the compound of the invention may be a pharmaceutically acceptable salt or cosmetically acceptable salt of a molecule comprising fatty acid covalently coupled to a substrate-binding peptide, either directly or via a linker. A preferred compound may be used in accordance with the invention to the exclusion of a compound other than the preferred compound.

The term "composition", as used herein for purposes of the specification and claims, refers to a macromolecular network comprised of a plurality of compound according to the invention, wherein non-covalent interactions between fatty acid components of the plurality of compound contribute to association between individual molecules of compound in the composition, resulting in formation of a macromolecular network, and while allowing the substrate-binding peptide components of the plurality of compound to bind to a substrate for which they have binding specificity. As will be described herein in more detail, the molecular network provides the compound with unexpected and beneficial properties, including but not limited to one or more improved biophysical properties. A composition of the invention comprises a macromolecular network represented by general formula (I):

$$(\text{SBP-FA-FA-SBP})_n$$

wherein

SBP comprises a substrate-binding peptide, and more preferably a substrate-binding peptide in a biofunctional composition comprising at least two substrate-binding peptides covalently coupled to each other;

FA comprises fatty acid;

wherein FA of one compound associates with FA of one or more other compounds through non-covalent interactions (as schematically represented by the "—" in formula (I)) in forming a macromolecular network capable of binding to a substrate via the substrate-binding peptide component;

n is an integer equal to or greater than 1; and wherein the composition has improved biophysical properties as compared to the substrate-binding peptide by itself. In one preferred embodiment, FA comprises two or more molecules of fatty acid covalently coupled to each other; or one large fatty acid of greater or equal to 25 carbons in the carboxylic acid chain. The term "macromolecular", when referring to a network of which is comprised a composition of the invention, means that the network is comprised of more than one monomeric, molecular unit; and also refers to a network formed by aggregates of two or more molecules held together by non-covalent interactions. Preferably, the non-covalent interactions are sufficient in molecular association so that the two or more molecules do not readily dissociate. A preferred composition may be used in accordance with the invention to the exclusion of a composition other than the preferred composition.

In addition, the term "composition", as used herein for purposes of the specification and claims, refers to a macromolecular network comprised of a plurality of first and second substrate binding domains that are non-covalently coupled at least in part through one or more hydrophobic or charged interaction tags according to the presently disclosed subject matter, wherein non-covalent interactions between hydrophobic and/or charged interaction tags of the plurality of substrate binding domain comprising molecules contribute to association between individual molecules in the composition resulting in formation of a macromolecular network, and while allowing the substrate-binding domain components of the plurality of molecules to bind to a substrate for which they have binding specificity. In some embodiments, the "compositions" of the presently disclosed subject matter further comprise the target molecules to which the plurality of second substrate binding molecules have binding affinity. When the composition comprising the macromolecular network comprised of a plurality of non-covalently coupled first and second substrate binding domains is contacted with a tissue or a medical device in the presence of the target molecule, the composition is useful for loading the target molecule onto the tissue or medical device.

Fatty acids are known to those skilled in the art as aliphatic monocarboxylic acids having a chain of no less than 5 and no more than 30 carbons. The fatty acid may be branched, unbranched, saturated, unsaturated, even-numbered carbons, odd-numbered carbons, a monoacid, a di-acid. Preferred fatty acids useful in this invention are fatty acid having a chain ranging from 9 carbons to 30 carbons. Also, as described in more detail herein, one or more (and preferably two or more) molecules of fatty acid may be covalently coupled to single molecule of substrate-binding peptide to form a compound of the invention. Illustrative examples of preferred fatty acids useful for producing a compound of the invention include, but are not limited to, decanoic acid, aminoundecanoic acid, lauric acid, myristic acid, palmitic acid, aminohexanoic acid, and stearic acid. A preferred fatty acid may be used in accordance with the invention to the exclusion of a fatty acid other than the preferred fatty acid.

The term "charged interaction tag" is used, for purposes of the specification and claims, to refer to a molecule, compound, or moiety having a net positive or a net negative charge that can non-covalently interact with another charged molecule, compound, or moiety having a net opposite charge through electrostatic interactions. With respect to the presently disclosed subject matter, the charged interaction tags are used to non-covalently couple one substrate binding peptide or polymer to another substrate binding peptide or polymer. Thus, for example, a positively charged interaction tag coupled to a substrate binding peptide couples electrostatically with a negatively charged interaction tag covalently coupled to another substrate binding peptide or couples electrostatically with a negatively charged substrate binding polymer. In another example, a negatively charged interaction tag covalently coupled to a substrate binding peptide couples electrostatically with a positively charged interaction tag covalently coupled to another substrate binding peptide or couples electrostatically with a positively charged substrate binding polymer. In another example, a positively charged interaction tag covalently coupled so as to link a first and a second substrate binding peptide couples electrostatically with a negatively charged interaction tag similarly linking the first and second substrate binding peptides on a separate molecule. In this manner, the two separate molecules, each having a covalently linked first and second substrate binding peptide, are non-covalently coupled through the electrostatic interaction. Through such non-covalent electrostatic interactions, the charged interaction tags of the presently disclosed subject matter contribute to formation of a higher order macromolecular network of a plurality of molecules of first and second substrate binding domains.

There is no particular size or content limitations for the charged interaction tag so long as it has a net positive or a net negative charge and can fulfill its purpose when covalently coupled to a substrate-binding peptide or polymer to electrostatically couple with an oppositely charged tag on another substrate binding peptide or another oppositely charged substrate binding polymer. In addition, the charged interaction tag must allow for the substrate-binding activity of the peptides and polymers to be substantially retained. In some embodiments of the presently disclosed subject matter the charged interaction tags of the presently disclosed subject matter have a molecular weight of less than 10 kDa.

Examples of positively charged interaction tags include, for example, but are not limited to, poly-amino acids including polylysine and polyarginine and combinations and copolymers thereof; and polyamines and polyimines including, for example, polyethylamines, polyethylenimines (PEI), and combinations and copolymers thereof. In one embodiment where the positively charged interaction tag is a polyamino acid, the positively charged interaction tag comprises a net positive charge of about +3 to about +50, from about +3 to about +20, from about +4 to about +17, from about +5 to about +14, from about +6 to about +10, from about +6 to about +9, from about +6 to about +8, and from about +6 to about +7. A positively charged interaction tag that is a polylysine or a polyarginine, or a combination or copolymer thereof, ranges in length from about 3 amino acids to about 50 amino acids, from about 3 amino acids to about 40 amino acids, from about 3 amino acids to about 30 amino acids, from about 3 amino acids to about 20 amino acids, from about 3 amino acids to about 11, 12, 13, 14, 15, 16, 17, 18, or 19 amino acids, from about 4 amino acids to about 10 amino acids, from about 4 amino acids to about 9 amino acids, from about 5 amino acids to about 8 amino acids, and from about 6 amino acids to about 7 amino acids.

Examples of negatively charged interaction tags include, for example, but are not limited to, poly-amino acids including polyglutamic acid and polyaspartic acid and combinations and copolymers thereof; polylactic acid, polyglycolic acid, poly(lactic acid-co-glycolic acid), polystyrene sulfonate (PSS), and poly(styrenesulfonic-maleic acid), and combinations and copolymers thereof. In one embodiment where the negatively charged interaction tag is a polyamino acid, the negatively charged interaction tag comprises a net negative charge of about −3 to about −50, from about −3 to about −20, from about −4 to about −17, from about −5 to about −14, from about −6 to about −10, from about −6 to about −9, from about −6 to about −8, and from about −6 to about −7. A negatively charged interaction tag that is a polyaspartic acid or a polyglutamic acid, or a combination or copolymer thereof, ranges in length from about 3 amino acids to about 50 amino acids, from about 3 amino acids to about 40 amino acids, from about 3 amino acids to about 30 amino acids, from about 3 amino acids to about 20 amino acids, from about 3 amino acids to about 11, 12, 13, 14, 15, 16, 17, 18, or 19 amino acids, from about 4 amino acids to about 10 amino acids, from about 4 amino acids to about 9 amino acids, from about 5 amino acids to about 8 amino acids, and from about 6 amino acids to about 7 amino acids.

The term "hydrophobic interaction tag" is used, for purposes of the specification and claims, to refer to a molecule, compound, or moiety that is hydrophobic in nature and non-covalently interacts with another molecule, compound, or moiety that is hydrophobic in nature. With respect to the presently disclosed subject matter, the hydrophobic interaction tags are used to non-covalently couple one substrate binding peptide or substrate binding polymer domain to other substrate binding peptide or polymer domains through interactions including, but not limited to, all non-electrostatic interactions such as hydrophobic interactions, van der Waals interactions, and pi-stacking interactions.

Thus, for example, a hydrophobic interaction tag covalently coupled to a first substrate binding peptide or polymer can non-covalently couple with another hydrophobic interaction tag covalently coupled to a second substrate binding peptide or polymer. In another example, a hydrophobic interaction tag covalently coupled so as to link a first and a second substrate binding peptide non-covalently couples with a hydrophobic interaction tag covalently coupled to link the first and second substrate binding peptides on a separate molecule. In this manner, the two separate molecules, each having a linked first and second substrate binding peptide are non-covalently coupled together. Through such non-covalent interactions the hydrophobic interaction tags of the presently disclosed subject matter contribute to formation of a higher order macromolecular network of a plurality of first and second substrate binding domains. There is no particular size or content limitations for the hydrophobic interaction tag so long as it is hydrophobic in nature and can fulfill its purpose to non-covalently couple separate substrate binding peptides and/or polymers, and the substrate-binding activity of the peptides/polymers is substantially retained. In some embodiments of the presently disclosed subject matter the hydrophobic interaction tags of the presently disclosed subject matter have a molecular weight of less than 10 kDa.

Examples of hydrophobic interaction tags include, for example, but are not limited to, poly-amino acids (natural and non-natural and D- and L-isomers) including combinations, strings, and copolymers of very hydrophobic amino acids such as valine, leucine, isoleucine, methionine, tryptophan, phenylalanine, biphenylalanine, N-methylisoleucine; N-methylvaline; norvaline; norleucine; and less hydrophobic amino acids such as alanine, and tyrosine. Another example of hydrophobic interaction tags of the presently disclosed subject matter is fatty acids. The fatty acids of the presently disclosed subject matter include saturated and unsaturated fatty acids such as but not limited to butyric acid, caproic acid (or amino hexanoic acid ("Ahx")), caprylic acid, capric acid, undecanoic acid, aminoundecanoic acid (AUD), poly-aminoundecanoic acid, lauric acid, myristic acid, palmitic acid, stearic acid, arachidic acid, behenic acid, lignoceric acid, eicosanoic acid, docosanoic acid, tetracosanoic acid, myristoleic acid, palmitoleic acid, oleic acid, linoleic acid, α-linolenic acid, arachidonic acid, eicosapentaenoic acid, erucic acid, and docosahexaenoic acid. Another example of hydrophobic interaction tags of the presently disclosed subject matter are aromatic groups including pyrene or pi-stacking interactions such as with combinations of tyrosine and tryptophan.

The term "first substrate-binding peptide" is herein used interchangeably with the term "first substrate-binding domain" is used for purposes of the specification and claims, to refer to a peptide having ranging in length from 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more amino acids in length that has binding affinity for the tissue or medical device that is the first substrate of the presently disclosed subject matter.

The term "second substrate-binding peptide" is herein used interchangeably with the term "second substrate-binding domain" and is used for purposes of the specification and claims, to refer to a peptide having ranging in length from 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more amino acids in length that has binding affinity for the tissue or medical device that is the first substrate of the presently disclosed subject matter.

The phrase "first substrate-binding polymer having a net positive charge" is herein used interchangeably with the term "first substrate-binding domain", and is used, for purposes of the specification and claims, to refer to a polymer having a net positive charge that has binding affinity for the tissue or medical device that is the first substrate of the presently disclosed subject matter. With respect to the presently disclosed subject matter, the substrate-binding polymer having a net positive charge includes those polymers that non-covalently couple to the tissue or medical device. There is no particular size or content limitations for the substrate-binding polymer having a net positive charge so long as it fulfills its purpose of electrostatically coupling with the tissue or medical device. In some embodiments of the presently disclosed subject matter, the positively charged substrate-binding polymers of the presently disclosed subject matter have a molecular weight ranging from more than 1 kDa to about 700 kDa, from about 5 kDa to about 700 kDa, from about 5 kDa to about 100 kDa, from about 6 kDa, 7 kDa, 8 kDa, 9 kDa, or 10 kDa to about 50 kDa, from about 10 kDa to about 20 kDa, 30 kDa, or 40 kDa. The substrate-binding polymer having a net positive charge includes but is not limited to polymers such as, for example, poly-amino acids including polylysine and polyarginine and combinations and copolymers thereof; some polyamides including, for example, nylon and silk; polyamines and polyimines including, for example, polyethylamines, branched and linear polyethylenimines (PEI) and mixtures, combinations, and copolymers thereof. The positvely charged substrate-binding polymers of the presently disclosed subject matter have a molecular weight ranging from more than 1 kDa to about 700 kDa, from about 5 kDa to about 700 kDa, from about 5 kDa to about 100 kDa, from about 6 kDa, 7 kDa, 8 kDa, 9 kDa, or 10 kDa to about 50 kDa, from about 10 kDa to about 20 kDa, 30 kDa, or 40 kDa.

The phrase "first substrate-binding polymer having a net negative charge" is used, for purposes of the specification and claims, to refer to a polymer having a net negative charge that has binding affinity for the tissue or medical device that is the first substrate of the presently disclosed subject matter. With respect to the presently disclosed subject matter, the negatively charged substrate binding polymer includes those polymers that non-covalently couple to the tissue or medical device. There is no particular size or content limitations for the substrate-binding polymer having a net negative charge so long as it fulfills its purpose of electrostatically coupling with the tissue or medical device. In some embodiments of the presently disclosed subject matter, the negatively charged substrate-binding polymers of the presently disclosed subject matter have a molecular weight ranging from more than 1 kDa to about 700 kDa, from about 5 kDa to about 700 kDa, from about 5 kDa to about 100 kDa, from about 6 kDa, 7 kDa, 8 kDa, 9 kDa, or 10 kDa to about 50 kDa, from about 10 kDa to about 20 kDa, 30 kDa, or 40 kDa. The negatively charged first substrate-binding polymer includes but is not limited to polymers such as, for example, poly-amino acids including polyglutamic acid, polyaspartic acid and combinations and copolymers thereof, polycarboxylic acids; polylactic acid, polyglycolic acid, poly(lactic acid-co-glycolic acid), polymannuronic acid, polygalacturonic acid, polyglucuronic acid, polyguluronic acid, polystyrenesulfonic acids and combinations and copolymers thereof; polysaccharides, e.g., alginate, starch, chitin, carrageenan (sulfated polysaccharides), heparin, and pectin and their derivatives; cellulose and cellulosic polymers including, for example, carboxy methyl cellulose ("CMC"), hydroxypropylmethyl cellulose, cellulose acetate, cellulose butyrate, and cellophane; polyglycosaminoglycans including, for example, hyaluronic acid, chondroitin sulfate; and mixtures, combinations, and copolymers thereof.

The first substrate-binding peptide or polymer is also referred to herein for purposes of simplicity as the first substrate-binding domain. Similarly, the second substrate-binding peptide is also referred to herein as a substrate-binding domain. Accordingly, all of the first and second substrate-binding peptides and polymers can be referred to herein as substrate-binding domains.

The term "linker" is used, for purposes of the specification and claims, to refer to a compound or moiety that acts as a molecular bridge to couple at least two different molecules (e.g., with respect to the present invention, coupling a fatty acid to a peptide, coupling one substrate binding peptide or polymer to another substrate binding peptide or polymer, coupling a charged interaction tag or a hydrophobic interaction tag to a substrate binding peptide or polymer). Thus, for example, coupling at least one fatty acid to an amino acid of a peptide may involve one portion of the linker binding to the at least one fatty acid, and another portion of the linker binding to a chemical moiety of the amino acid of the peptide to be functionalized with the at least one fatty acid. As apparent to those skilled in the art, and using methods known in the art, two different molecules may be coupled to the linker in a step-wise manner, or may be coupled simultaneously to the linker. There is no particular size or content limitations for the linker so long as it can fulfill its purpose as a molecular bridge, and that the binding specificity of a substrate-binding peptide or a substrate binding-domain in a coating composition is substantially retained.

Linkers are known to those skilled in the art to include, but are not limited to, chemical compounds (e.g., chemical chains, compounds, reagents, and the like). The linkers may include, but are not limited to, homobifunctional linkers and heterobifunctional linkers. Heterobifunctional linkers, well known to those skilled in the art, contain one end having a first reactive functionality (or chemical moiety) to specifically link a first molecule, and an opposite end having a second reactive functionality to specifically link to a second molecule. It will be evident to those skilled in the art that a variety of bifunctional or polyfunctional reagents, both homo- and hetero-functional (such as those described in the catalog of the Pierce Chemical Co., Rockford, Ill.), amino acid linkers (typically, a short peptide of between 3 and 15 amino acids, and often containing amino acids such as glycine, and/or serine), and polymers (e.g., polyethylene glycol) may be employed as a linker with respect to the present invention. In one embodiment, representative peptide linkers comprise multiple reactive sites to be coupled to a binding domain (e.g., polylysines, polyornithines, polycysteines, polyglutamic acid and polyaspartic acid) or comprise substantially inert peptide linkers (e.g., polyglycine, polyserine, polyproline, polyalanine, and other oligopeptides comprising alanyl, serinyl, prolinyl, or glycinyl amino acid residues.

Suitable polymeric linkers are known in the art, and can comprise a synthetic polymer or a natural polymer. Representative synthetic polymers include but are not limited to polyethers (e.g., poly(ethylene glycol) ("PEG")), poly(propylene glycol), poly(butylene glycol), polyesters (e.g., polylactic acid (PLA) and polyglycolic acid (PGA)), polyamines, polyamides (e.g., nylon), polyurethanes, polymethacrylates (e.g., polymethylmethacrylate; PMMA), polyacrylic acids, polystyrenes, polyhexanoic acid, flexible chelators such as EDTA, EGTA, and other synthetic polymers which preferably have a molecular weight of about 20 Daltons to about 1,000 kiloDaltons. Representative natural polymers include but are not limited to hyaluronic acid, alginate, chondroitin sulfate, fibrinogen, fibronectin, albumin, collagen, calmodulin, and other natural polymers which preferably have a molecular weight of about 200 Daltons to about 20,000 kiloDaltons (for constituent monomers). Polymeric linkers can comprise a diblock polymer, a multi-block copolymer, a comb polymer, a star polymer, a dendritic or branched polymer, a hybrid linear-dendritic polymer, a branched chain comprised of lysine, or a random copolymer. A linker can also comprise a mercapto(amido)carboxylic acid, an acrylamidocarboxylic acid, an acrlyamido-amidotriethylene glycolic acid, 7-aminobenzoic acid, and derivatives thereof. In another example, a linker can be the charged or the hydrophobic interaction tag of the presently disclosed subject matter. Linkers may also be generated during the coupling process such a 'trizole nucleus' that is generated as a linker during the copper-catalyzed azide-alkyne cycloaddition (e.g., "click chemistry") or any other methods such as chemoselective ligation chemistry well known in the art.

If desired, a predetermined amount of the plurality of compound in the macromolecular network may be synthesized so as to be susceptible to cleavage (e.g., so as to promote biodegraDation after the macromolecular network has served its intended purpose), e.g., by choice of a particular linker between the fatty acid component and the peptide component of the compound. Cleavable linkers are known in the art that to be cleaved by a number of mechanisms (e.g., by heat, by natural enzymes found in or on the body of an individual, by pH sensitivity). Examples of pH-sensitive materials useful as linkers may include, but are not limited to, cellulose acetate phthalate, cellulose acetate trimellitate, polyvinyl acetate phthalate, hydroxypropyl methylcellulose phthalate, and hydroxypropyl methylcellulose acetate succinate. An example of a linker cleaved by natural enzymes may comprise an amino acid linker comprised of a short chain of (e.g., 3 to 8) amino acids, with a C-terminal amino acid residue comprising lysine or arginine, and cleavage of the linker is via serum carboxypeptiDases (N or R or both) which cleave C-terminal lysine or arginine residues.

Depending on such factors as the molecules to be linked, and the conditions in which the linking is performed, the linker may vary in length and composition for optimizing such properties as preservation of biological function, stability, resistance to certain chemical, enzymatic, and/or temperature parameters, and of sufficient stereo-selectivity or size. For example, where the compound of the invention comprises a fatty acid linked to a substrate-binding peptide, the linker should not significantly interfere with the ability of a compound according to the present invention to sufficiently bind specifically, with appropriate avidity for the purpose, to a substrate for which the substrate-binding peptide has the ability to bind. A preferred linker may be a molecule which may have activities which enhance or complement the effect of a compound or composition of the present invention. A preferred linker may be used in the present invention to the exclusion of a linker other than the preferred linker.

The interaction tags of the presently disclosed subject matter are covalently coupled (or covalently linked) to the substrate binding peptides and polymers of the presently disclosed subject matter. The terms "covalently coupled", "covalently linked", and "linked" are for the purposes of the specification and claims to have the same meaning and are herein used interchangeably. In one embodiment of the presently disclosed subject matter, the covalent coupling between the interaction tag and the substrate binding domain is a direct coupling between a chemical group on the hydrophobic or charged interaction tag to a chemical group on the substrate binding peptide or polymer. In another embodiment, the covalent coupling is an indirect coupling through another group. For example, in some embodiments the charged and hydrophobic interaction tags of the presently disclosed subject matter are linked in a manner including, but not limited to, linked directly, linked through one or more amino acids, linked through a proline amino acid residue, linked through a polymer, linked through a polyethylene glycol ("PEG") polymer, linked through a 10 unit polyethylene glycol ("P10") polymer, linked through a 6 unit polyethylene glycol ("MP") polymer, linked through one or more fatty acid molecules, and linked through one or more aminohexanoic acid molecules.

The terms "binds specifically" or "binding specificity" or "binding affinity" and like terms used herein, are interchangeably used, for the purposes of the specification and claims, to refer to the ability of a peptide and (as a substrate-binding domain is described herein) to have a binding affinity that is greater for one target substrate selected to be bound over another substrate other than the target substrate; e.g., an affinity for a given substrate in a heterogeneous population of other substrates which is greater than, for example, that attributable to non-specific adsorption. For example, a peptide has binding specificity for metal when the peptide demonstrates preferential binding to metal, as compared to binding to another non-biological substrate such as a polymer or a biological substrate (e.g., a cell). Such preferential binding may be dependent upon the presence of a particular conformation, structure, and/or charge on or within the peptide and/or material for which it has binding specificity.

In some embodiments, a peptide that binds specifically to a particular substrate, material or composition binds at least 10%, 20%, 30%, 40%, 50%, 60%, 70%, 80%, 90%, 100%, 200%, 300%, 400%, 500%, or a higher percentage, than the peptide binds to an appropriate control such as, for example, a different substrate, or a protein typically used for such comparisons such as bovine serum albumin. For example, binding specificity can determined by an assay in which quantitated is a signal (e.g., fluorescence, or calorimetric) representing the relative amount of binding between a peptide and a substrate. In a preferred embodiment, a peptide has a binding specificity that is characterized by a relative binding affinity as measured by an EC50 of 10 μM or less, preferably less than 1 μM, and more preferably less than 0.1 μM. The EC50 can be determined using any number of methods known in the art, such as by generating a concentration response curve from a binding assay in which the concentration of the peptide is titered with a known amount of the substrate for which the peptide has binding specificity. In such case, the EC50 represents the concentration of peptide producing 50% of the maximal binding observed for that peptide in the assay.

The term "peptide" is used herein, for the purposes of the specification and claims to refer to chain of contiguous amino acids comprising no less than about 3 amino acids and no more than about 100 amino acid residues in length, and more preferably from about 8 amino acids to about 60 amino acids. The amino acid chain may include naturally occurring amino acids, synthetic amino acids, genetically encoded amino acids, non-genetically encoded amino acids, one or more enantiomers of an amino acid, and combinations thereof; an oligomer of the peptide (as previously described herein); a peptide derivative (including, for example, peptide conjugate, cyclized peptide, polymerized peptide, chemically modified peptide, and a peptide mimetic). As known to those skilled in the art, polypeptide (also known as a "protein") comprises an amino acid chain larger than a peptide. As used herein, the term "peptide" also encompasses a peptide wherein one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), an N-modified bond (—NRCO), and a thiopeptide bond (CS—NH). A peptide or polypeptide (protein) used in accordance with the present invention may be produced by chemical synthesis, recombinant expression, biochemical or enzymatic fragmentation of a larger molecule, chemical cleavage of larger molecule, biological assembly, a combination of the foregoing or, in general, made by any other method in the art, and preferably isolated. A preferred peptide may be used in the present invention to the exclusion of a peptide other than the preferred peptide.

A peptide, used as a component of the compound according to the invention, may also comprise an oligomer (e.g., dimer, multimer) of the same peptide amino acid sequence or comprised of two or more different amino acid sequences. For example, two or more substrate-binding peptides are coupled together (e.g., by one or more of physically, chemically, synthetically, or biologically (e.g., via recombinant expression)) in such a way that each retains its respective function to bind to the respective substrate for which each has binding specificity. Such coupling may include forming a multimeric molecule having two or more peptides having binding specificity the same substrate (e.g., two or more polymer binders), two or more peptides having binding specificity for different substrates (e.g., one or more metal binders, and one or more polymer binders), and a combination thereof. For example, using standard reagents and methods known in the art of peptide chemistry, two peptides may be coupled via a side chain-to-side chain bond (e.g., where each of the peptides has a side chain amine (e.g., such as the epsilon amine of lysine)), a side chain-to-N terminal bond (e.g., coupling the N-terminal amine of one peptide with the side chain amine of the other peptide), a side chain-to-C-terminal bond (e.g., coupling the C-terminal chemical moiety (e.g., carboxyl) of one peptide with the side chain amine of the other peptide), an N-terminal-to-N-terminal bond, an N-terminal to C-terminal bond, a C-terminal to C-terminal bond, or a combination thereof. In synthetic or recombinant expression, two or more peptides can be coupled directly to a peptide by synthesizing or expressing the two or more peptides as a single peptide. The coupling of two or more peptides may also be via a linker to form substrate-binding peptide used in the composition according to the present invention.

The term "isolated" means that a molecule (e.g., compound of the invention) is substantially free of components which have not become part of the integral structure of the molecule itself; e.g., such as substantially free of cellular material or culture medium when produced by recombinant techniques, or substantially free of chemical precursors or other chemicals when chemically synthesized or produced using biochemical, enzymatic, recombinant, or chemical processes.

The term "amino acid" is used herein, for the purposes of the specification and claims to refer to one or more of: an L-form amino acid, D-form amino acid, natural amino acid (genetically encoded amino acid), non-genetically encoded amino acid, and a chemically-modified amino acid (e.g. containing one or more protecting groups, or chemical end group, as will be described herein in more detail). Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; biphenylalanine, desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; ornithine; and 3-(3,4-dihydroxyphenyl)-L-alanine ("DOPA"). Representative chemically modified amino acids include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also, a chemically-modified amino acid, for example, comprises a chemical moiety (an "N-terminal group") added to an amino acid, such as an N-terminal amino acid on a peptide, to block chemical reactivity of that amino terminus. Peptides containing amino acids protected by chemical modification are termed "modified peptides". Such N-terminal groups for protecting the amino terminus of a peptide are well known in the art, and include, but are not limited to, lower alkanoyl groups, acyl groups, sulfonyl groups, and carbamate forming groups. Preferred N-terminal groups may include acetyl, Fmoc, and Boc. A chemical moiety, added to the C-terminal amino acid of a peptide to block chemical reactivity of that carboxy terminus, comprises a C-terminal group. Such C-terminal groups for protecting the carboxy terminus are well known in the art, and include, but are not limited to, an ester or amide group. Such terminal modifications are often useful to reduce susceptibility by proteinase digestion, and to therefore prolong a half-life of amino acids and peptides in the presence of biological fluids where proteases can be present. Optionally, a chemically modified amino acid may be one that is modified to contain one or more chemical moieties (e.g., reactive functionalities such as fluorine, bromine, or iodine) to facilitate linking the peptide to a linker molecule or fatty acid.

The term "carrier medium" is herein used interchangeably with the term "pharmaceutically acceptable solution", when used herein for purposes of the specification and claims, means a medium to which is added compound according to the present invention. In one embodiment, a composition of the invention may be formed by adding compound and the carrier medium together under sufficient conditions to form macromolecular network of which is comprised the composition. As known to those skilled in the art, components included in a carrier medium will often depend on the intended use of the resultant composition. Examples of such a carrier medium include, but are not limited to, a liquid, a pharmaceutically acceptable carrier, a cosmetically acceptable carrier, aqueous solution, aqueous or non-aqueous solvent, suspension, emulsion, gel, paste, formulation, cream, lotion, powder, serum, and a combination thereof. As known to those skilled in the art, a carrier medium may comprise one or substances, including but not limited to, water, buffered water, medical parenteral vehicles, saline, 0.3% glycine, aqueous alcohols, isotonic aqueous buffer; and may further include one or more substances such as alginic acid, water-soluble polymer, glycerol, glycols (e.g., polyethylene glycol), polyols (e.g., glycerin, sorbitol, etc.), oils, salts (such as sodium, potassium, magnesium and ammonium, phosphonates), esters (e.g., carbonate esters, ethyl oleate, ethyl laurate, etc.), fatty acids, vitamins, protein, carbohydrates, polysaccharides, starches, glycoproteins (for enhanced stability), buffering agents (e.g., magnesium hydroxide, aluminum hydroxide, and the like), bulking agents, excipients, wetting agents, and preservatives (including, but not limited to, ascorbic acid, cysteine hydrochloride, sodium bisulfite, ascorbyl palmitate, tocopherol), and/or stabilizers (to increase shelf-life or as necessary and suitable for manufacture and distribution of the composition).

The term "medical device" is used herein, as used herein for purposes of the specification and claims, refers to a structure that is positioned or positionable into or onto an individual's body to prevent, treat, modulate or ameliorate damage or a disorder or disease or condition, repair or restore a function of a damaged tissue; or to provide a new function. In a preferred embodiment in which applied to a medical device is a compound or composition according to the invention, the medical device comprises at least one substrate or surface with which is contacted a compound or composition according to the invention. Representative medical devices include, but are not limited to: hip endoprostheses, artificial joints, jaw or facial implants, dental implants, tendon and ligament replacements, skin replacements, metal replacements and metal screws, metal nails or pins, metal graft devices, polymer-containing grafts, vascular prostheses, heart pacemakers, artificial heart valves, blood filters, closure devices (e.g., for closure of wounds, incisions, or defects in tissues, including but not limited to skin and other organs (heart, stomach, liver, etc.)), sutures, breast implants, penile implants, stents, catheters, shunts, nerve growth guides, leads for battery-powered medical devices, intraocular lenses, wound dressings, tissue sealants, aneurismal coils, prostheses (e.g., cochlear implants, visual prostheses (including, but not limited to, contact lenses, and other visual aid devices), neurostimulators, muscular stimulators, joint prosthesis, a spinal cord implant (e.g., an implant for bridging a gap in a severed spinal cord or nerve, typically used to promote nerve regeneration), dental prosthesis, etc.), ophthalmic devices (glaucoma shunts, ophthalmic inserts, intraocular lenses, overlay lenses, ocular inserts, optical inserts), and nebulizers. Medical devices may be comprised of one or more non-biological substrates, one or more biological substrates, and a combination thereof. A preferred medical device may be used in accordance with the present invention to the exclusion of a medical device other than the preferred medical device.

The phrase "substrate is a tissue or a medical device" is used herein for purposes of the specification and claims to mean a substrate that is a tissue or a medical device as the term "tissue" and the term "medical device" is defined herein. The term "tissue" is herein meant to comprise living animal tissue or a tissue isolated or extracted from a living animal. The term "tissue" comprises a material selected from the group consisting of an animal tissue, an autologous tissue, an allogeneic tissue, a transplanted tissue, an organ tissue, a bone tissue, a skin tissue, a connective tissue, a muscle tissue, a nervous tissue, a polymer, a collagen, and a calcium phosphate based material, and combinations thereof. In addition to the definition of the term "medical device" herein above, the term "medical device" comprises a material selected from the group consisting an allogeneic tissue, a transplanted tissue, a polymer, a silk, a collagen, a synthetic polymer, a polyester, a polyurethane, a nylon, a polylactic acid, a polyglycolic acid, poly(lactic acid-co-glycolic acid), a plastic, a silicone material, a metal, a metal oxide, a non-metal oxide, a ceramic material, a calcium phosphate based material, a carbon-based material, a metallo-carbon composite, and combinations thereof. In some aspects the term "medical device" comprises certain "non-biological substrates" as used herein. For example, the phrase "substrate is a medical device" further includes, but is not limited to, a container, reactor, device, array, medical device, particle (e.g., microparticle, nanoparticle, and the like), and a combination thereof. The phrase "substrate is a medical device" further includes, but is not limited to (a) medical supplies, such as bandages, dressings, sponges, covers, and the like; (b) laboratory equipment, such as bioreactors, fermentors, test tubes, assay plates, arrays, culture containers, and the like; and (c) packaging or product protection (e.g., packaging materials, coverings (such as wraps)), such as applied to perishables such as foods, drugs, and medical devices.

The term "target molecule" is used herein for purposes of the specification and claims to mean the target molecule is selected from the group consisting of a cell, a protein, a polypeptide, a growth factor, a growth differentiation factor (GDF), a platelet derived growth factor (PDGF), a transforming growth factor (TGF), an osteogenic protein, a bone morphogenic protein (BMP), a hormone, a protein hormone, a parathyroid hormone (PTH), a drug, a drug carrier, an antibiotic, a vancomycin antibiotic, a steroid, a dexamethasone, and combinations thereof. In some aspects the term "target molecule" comprises certain "biological substrates" as used herein. For example, a target molecule can comprise a biological molecule including, but not limited, to a protein (e.g., an antibody, antibody chain, avimer, collagen, keratin or other proteinaceous tissue component or structure, polypeptide, a receptor, a glycoprotein, a lipoprotein, a hormone, a growth factor, a cytokine, a chemical mediator, and the like), a peptide, a lipid, a carbohydrate (e.g., a polysaccharide, starch, monosaccharide), a nucleic acid molecule (e.g., an aptamer, DNA, RNA, hybrid nucleic acid molecule, vectors, chemically modified nucleic acid molecule), an oligomer, a small molecule (e.g., a chemical compound; metabolites, such as sugars, folic acid, uric acid, lactic acid), a drug (e.g., a biological-based drug, hormone, antimicrobial compound, growth factor, signaling molecule, ligand, etc.), a signaling molecule, a ligand, a nucleic acid-protein fusion, fragments thereof, analogs thereof, and a combination thereof.

The term “drug delivery vehicle”, when used herein for purposes of the specification and claims, means a carrier for one or more biologically active agents; preferably, the carrier comprising a microparticle, liposome, polymer, carrier structure (e.g., matrix formed of biological substrate or a non-biological substrate or a combination thereof), or combination thereof, and generally in the size range of nanometers to microns.

The terms “covalent coupling”, “covalently coupled” and like terms, refer to a covalent bond being formed between two molecules. Covalent coupling may be achieved by any means known in the art. For example, a first molecule comprises a reactive functionality comprising a chemical group which can covalently bond with a chemical-reactive group (reactive with the chemical group of the first molecule) of a second molecule. Free chemical groups include, but are not limited to, a thiol carboxyl, hydroxyl, amino, amine, sulfo, phosphate, or the like; whereas chemical-reactive groups include, but are not limited to, thiol-reactive group, carboxyl-reactive group, hydroxyl-reactive group, amino-reactive group, amine-reactive group, sulfo-reactive group, or the like.

The terms “pharmaceutically acceptable salt” and “cosmetically acceptable salt”, when used herein for purposes of the specification and claims, is known in the art to mean that the compound or composition according to the invention may also be in the form of a salt. Preferably, the salt form retains one or more beneficial properties of the compound or composition of the invention. Typically, salts are formed with inorganic acids (e.g., phosphoric acid, hydrochloric acid, sulfuric acid, and the like), organic acids (e.g., acetic acid, benzoic acid, propionic acid, maleic acid, glycolic acid, succinic acid, N-acetylcysteine, and the like), and other salts known to those skilled in the art which can be readily adapted for use as a compound or composition according to the invention.

Figure 3:
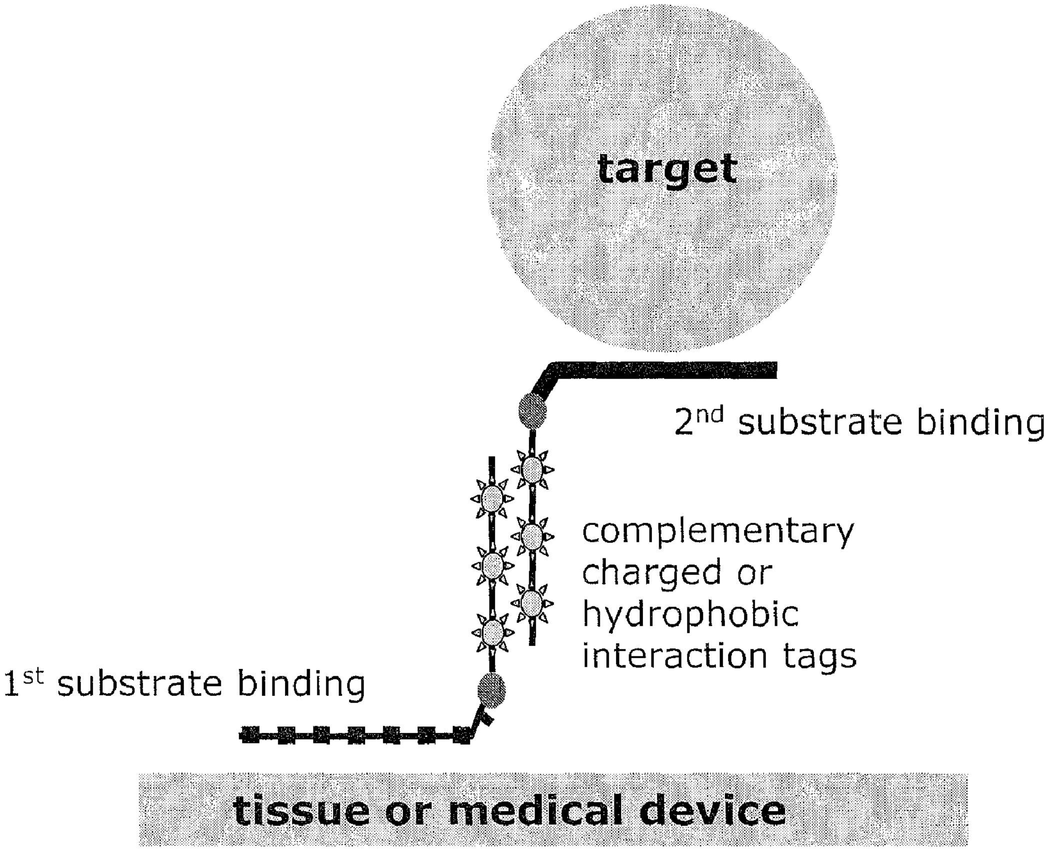
FIG. 3 is a schematic diagram showing a composition of the presently disclosed subject matter where a first substrate-binding domain having a covalently coupled hydrophobic or charged interaction tag is non-covalently bound to a tissue or medical device and it is also non-covalently coupled to the interaction tag on a second substrate-binding domain that is non-covalently bound to a target molecule.

In one embodiment, the presently disclosed subject matter provides compositions comprising a first substrate-binding peptide (or a first substrate-binding polymer having a net positive or a net negative charge) having binding affinity for a tissue or a medical device, a second substrate-binding peptide having binding affinity for a target molecule, wherein the first and second substrate-binding domains are not covalently linked, and the target molecule (see, for example FIG. 3). Each of the first and second substrate-binding peptides/polymers is covalently coupled to at least one interaction tag selected from the group consisting of a hydrophobic interaction tag, a negatively charged interaction tag, and a positively charged interaction tag (see FIG. 3). When the substrate-binding peptide/polymer molecules are combined, the hydrophobic interaction tags interact with each other and the charged interaction tags interact with the oppositely charged interaction tags or the oppositely charged substrate binding polymers, to form a macromolecular network of non-covalently coupled first and second substrate-binding peptides/polymers (see, for example, FIGS. 4A-C (peptides) & 5A-5C (polymer/peptide)). In this manner, the substrate-binding peptide/polymer molecules are useful when combined with the target molecule for coating onto the tissue or medical device to achieve loading of the target molecule onto the tissue or medical device (see, e.g., Examples 17-19). In some embodiments, the first substrate-binding peptide/polymer, the second substrate-binding peptide, and the target molecule are present in a pharmaceutically acceptable solution. In some embodiments, the pharmaceutically acceptable solution is in the form of a gel. In some embodiments, the tissue or medical device is first coated with one or more of the first or second substrate binding peptide/polymer, rather than being coated after the three components are mixed together. The order of coating the tissue or medical device with the composition comprising a first and a second substrate-binding peptide/polymer and a target molecule can be varied.

The first substrate-binding peptide or polymer is also referred to herein for purposes of simplicity as the first substrate-binding domain. Similarly, the second substrate-binding peptide is also referred to herein as a substrate-binding domain. Accordingly, all of the first and second substrate-binding peptides and polymers can be referred to herein as substrate-binding domains. In addition, the substrate binding molecules depicted in FIGS. 4A-4C and 5A-5C are not meant to attempt to describe every possible combination of covalently coupled interaction tag on a substrate binding domain. For example, the first and second substrate binding domains can comprise any combination of one or more hydrophobic and charged interaction tag, as long as the combination allows for a plurality of first and second substrate binding molecules to form a non-covalent coupling with each other according to the rules of hydrophobic tags interacting with each other and charged interaction tags interacting with other oppositely charged interaction tags. One embodiment, for example, that is not depicted in either FIGS. 4A-4C or FIGS. 5A-5C is the embodiment where the charged interaction tags are absent and each of the first and second binding domains comprises a covalently coupled hydrophobic interaction tag.

In some embodiments of the presently disclosed subject matter a composition is provided comprising a plurality of a first substrate-binding peptide comprising 3 to 40 amino acids, wherein the first substrate is a tissue or a medical device and the first substrate-binding peptide has binding affinity for the tissue or the medical device; a plurality of a second substrate-binding peptide comprising of 3 to 40 amino acids, wherein the second substrate is a target molecule and the second substrate-binding peptide has binding affinity for the target molecule, wherein the first and second substrate-binding peptides are not covalently linked; and a plurality of the target molecule; wherein each of the first and second substrate-binding peptides is covalently coupled to at least one interaction tag selected from the group consisting of a hydrophobic interaction tag, a positively charged interaction tag, and a negatively charged interaction tag, wherein the hydrophobic interaction tags interact with each other and the positively charged interaction tags interact with the negatively charged interaction tags to form a macromolecular network comprising the plurality of non-covalently coupled first and second substrate-binding peptides.

In some embodiments, the first substrate tissue or medical device comprises a material selected from the group consisting of an animal tissue, an autologous tissue, an allogeneic tissue, a transplanted tissue, an organ tissue, a bone tissue, a skin tissue, a connective tissue, a muscle tissue, a nervous tissue, a polymer, a silk, a collagen, a synthetic polymer, a polyester, a polyurethane, a nylon, a polylactic acid, a polyglycolic acid, poly(lactic acid-co-glycolic acid), a plastic, a silicone material, a metal, a metal oxide, a non-metal oxide, a ceramic material, a calcium phosphate based material, a carbon-based material, a metallo-carbon composite, and combinations thereof.

In some embodiments, the target molecule is selected from the group consisting of a cell, a protein, a polypeptide, a growth factor, a growth differentiation factor (GDF), a platelet derived growth factor (PDGF), a transforming growth factor (TGF), an osteogenic protein, a bone morphogenic protein (BMP), a hormone, a protein hormone, a parathyroid hormone (PTH), a drug, a drug carrier, an antibiotic, a vancomycin antibiotic, a steroid, a dexamethasone, and combinations thereof.

In some embodiments, the charged interaction tag is selected from the group consisting of polylysine, polyarginine, polyamines, polyimines, polyethylamines, polyethylenimines (PEI), polyaspartic acid, polyglutamic acid, polystyrene sulfonate, poly(styrenesulfonic-maleic acid), and combinations and copolymers thereof.

In some embodiments, the hydrophobic interaction tag is selected from the group consisting of fatty acids, undecanoic acid, poly-undecanoic acid, myristic acid, amino hexanoic acid, capric acid, lauric acid, palmitic acid, stearic acid, aromatic compounds, and combinations and copolymers thereof.

In some embodiments, the first substrate is a metal medical device, the second substrate target molecule is vancomycin, the positively charged interaction tag covalently coupled to the first substrate binding peptide is polyarginine and the negatively charged interaction tag covalently coupled to the second substrate binding peptide is polyglutamic acid or polyaspartic acid, the positively and negatively charged interaction tags are coupled to the substrate binding peptide directly or coupled through a polyethylene glycol, and the hydrophobic interaction tag is absent. In some embodiments, the first substrate binding polymer having a positive charge is polyethyleneimine of various molecular weights.

In some embodiments, the first substrate is a metal medical device, the second substrate target molecule is vancomycin, the positively charged interaction tag covalently coupled to the first substrate binding peptide is polyarginine and the negatively charged interaction tag covalently coupled to the second substrate binding peptide is polyglutamic acid or polyaspartic acid, the positively and negatively charged interaction tags are coupled to the substrate binding peptides directly by a peptide bond or coupled through a polyethylene glycol, the hydrophobic interaction tag is poly-undecanoic acid and is covalently coupled to either the first or the second substrate binding pepdide directly, through a polyethylene glycol, or through an aminohexanoic acid.

In some embodiments, the presently disclosed subject matter provides a composition comprising a plurality of a first substrate-binding polymer having a net negative or a net positive charge, wherein the first substrate is a tissue or medical device and the first substrate-binding polymer has binding affinity for the tissue or medical device; a plurality of a second substrate-binding peptide of 3 to 40 amino acids, wherein the second substrate is a target molecule and the second substrate-binding peptide has binding affinity for the target molecule, wherein the first substrate-binding polymer and the second substrate-binding peptide are not covalently linked; and a plurality of the target molecule, wherein the plurality of second substrate-binding peptides are covalently coupled to at least one net positively or net negatively charged interaction tag, wherein the charge of the interaction tag is opposite to the charge of the first substrate-binding polymer, wherein each of the plurality of first substrate-binding polymers and second substrate-binding peptides is optionally covalently coupled to a hydrophobic interaction tag, wherein the charged interaction tag interacts with the first substrate-binding polymer and the optional hydrophobic interaction tags interact with each other to form a macromolecular network comprising the plurality of non-covalently coupled first substrate-binding polymers and second substrate-binding peptides.

In some embodiments, the first substrate tissue or medical device comprises a material selected from the group consisting of an autologous tissue, an allogeneic tissue, a transplanted tissue, an organ tissue, a bone tissue, a skin tissue, a connective tissue, a muscle tissue, a polymer, a synthetic polymer, a plastic, a metal, a metal oxide, a non-metal oxide, a ceramic material, a calcium phosphate based material, and combinations thereof. In some embodiments, the target molecule is selected from the group consisting of a cell, a protein, a polypeptide, a growth factor, a growth differentiation factor (GDF), a platelet derived growth factor (PDGF), a transforming growth factor (TGF), an osteogenic protein, a bone morphogenic protein (BMP), a hormone, a protein hormone, a parathyroid hormone (PTH), a drug, a drug carrier, an antibiotic, a vancomycin antibiotic, a steroid, a dexamethasone, and combinations thereof.

In some embodiments, the first substrate-binding polymer having a net negative charge is selected from the group consisting of polystyrene sulfonate, polyglutamic acid, polylactic acid, polyglycolic acid, poly(lactic acid-co-glycolic acid), heparin, and combinations and copolymers thereof. In some embodiments, the first substrate-binding polymer having a net positive charge is selected from the group consisting of polyimines, polyamines, polyethylenimines, polyethylamines, and polylysine, and combinations and copolymers thereof. In some embodiments, the charged interaction tag is selected from the group consisting of polylysine, polyarginine, polyamines, polyimines, polyethylamines, polyethylenimines (PEI), polyaspartic acid, polyglutamic acid, polystyrene sulfonate, poly(styrenesulfonic-maleic acid), and combinations and copolymers thereof. In some embodiments, the hydrophobic interaction tag is selected from the group consisting of fatty acids, undecanoic acid, poly-undecanoic acid, myristic acid, amino hexanoic acid, capric acid, lauric acid, palmitic acid, stearic acid, aromatic compounds, and combinations and copolymers thereof.

In some embodiments, the first substrate is a metal medical device, the second substrate target molecule is vancomycin, the first substrate binding polymer having a positive charge is polyethylenimine, the negatively charged interaction tag covalently coupled to the second substrate binding peptide is polyglutamic acid or polyaspartic acid, the charged interaction tag is coupled to the substrate binding peptide directly or coupled through a polyethylene glycol, and the optional hydrophobic interaction tag is absent.

In some embodiments of the presently disclosed subject matter, the compositions of the presently disclosed subject matter comprise a first substrate-binding peptide having binding affinity for a tissue or medical device covalently linked to a second substrate-binding peptide having binding affinity for a target molecule, and the target molecule. Each of the covalently linked first and second substrate-binding peptides is covalently coupled to at least one interaction tag selected from the group consisting of a hydrophobic interaction tag, a positively charged interaction tag, and a negatively charged interaction tag. The covalently linked substrate-binding peptide molecules and the target molecules are combined resulting in the hydrophobic interaction tags interacting with each other and the charged interaction tags interacting with oppositely charged interaction tags (see, for example, FIGS. 6A-6B). In this manner, a macromolecular network is formed comprising the linked substrate-binding domain molecules non-covalently coupled together, and when combined with the target molecule and coated onto a tissue or medical device, the composition loads the target molecule onto the tissue or medical device. (see, e.g., Examples 17-19). In some embodiments, the first and second substrate-binding domains and the target molecule are present in a pharmaceutically acceptable solution. In some embodiments, the pharmaceutically acceptable solution is in the form of a gel. In some embodiments, the tissue or medical device is first coated with one or more of the first or second substrate binding domains, rather than being coated after all the components are mixed together. The order of coating the tissue or medical device with the compositions comprising a first and a second substrate-binding domain and a target molecule can be varied.

Figure 4:
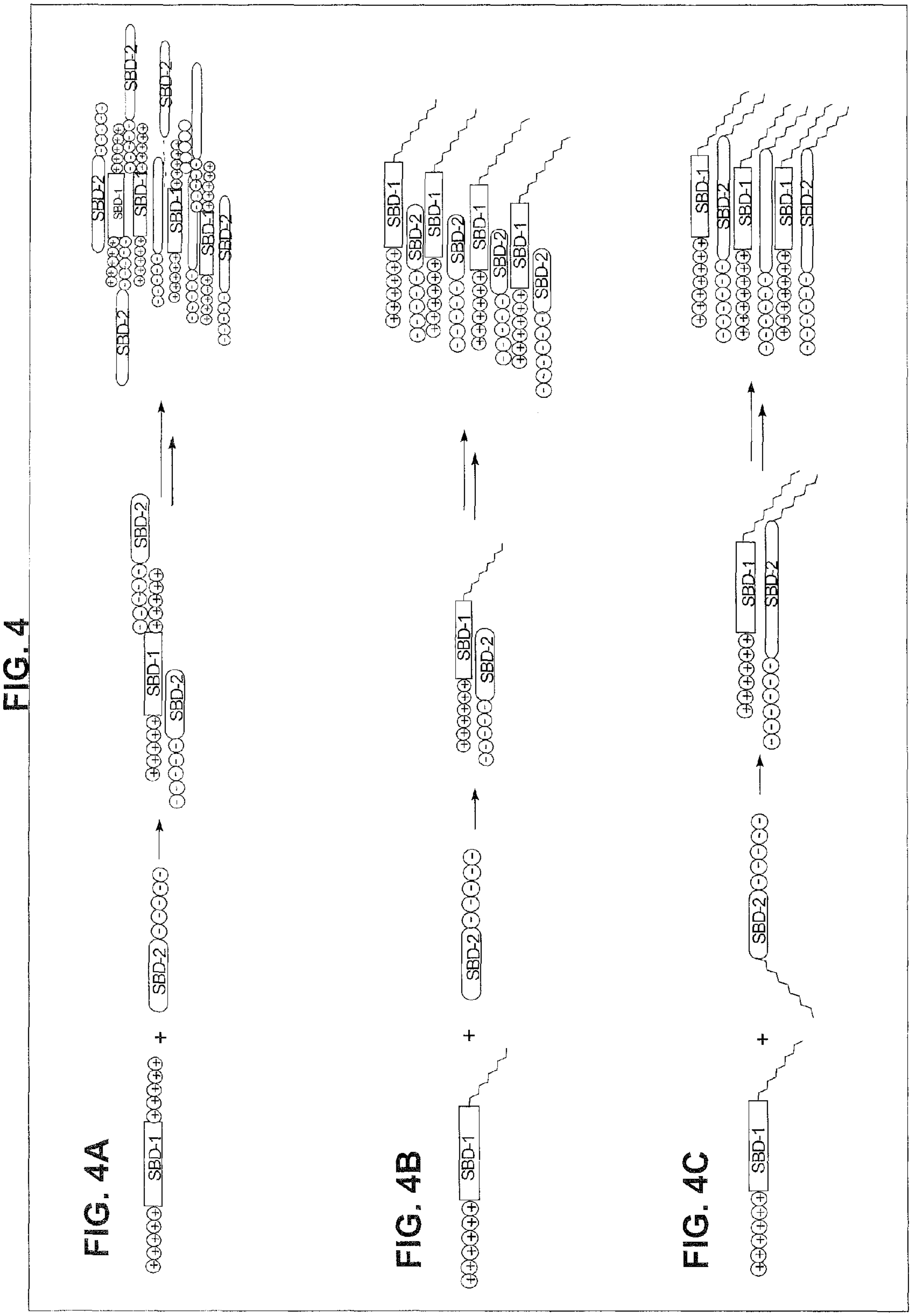
FIGS. 4A-4C are schematic diagrams showing 3 separate compositions of the presently disclosed subject matter.
Figure 5:
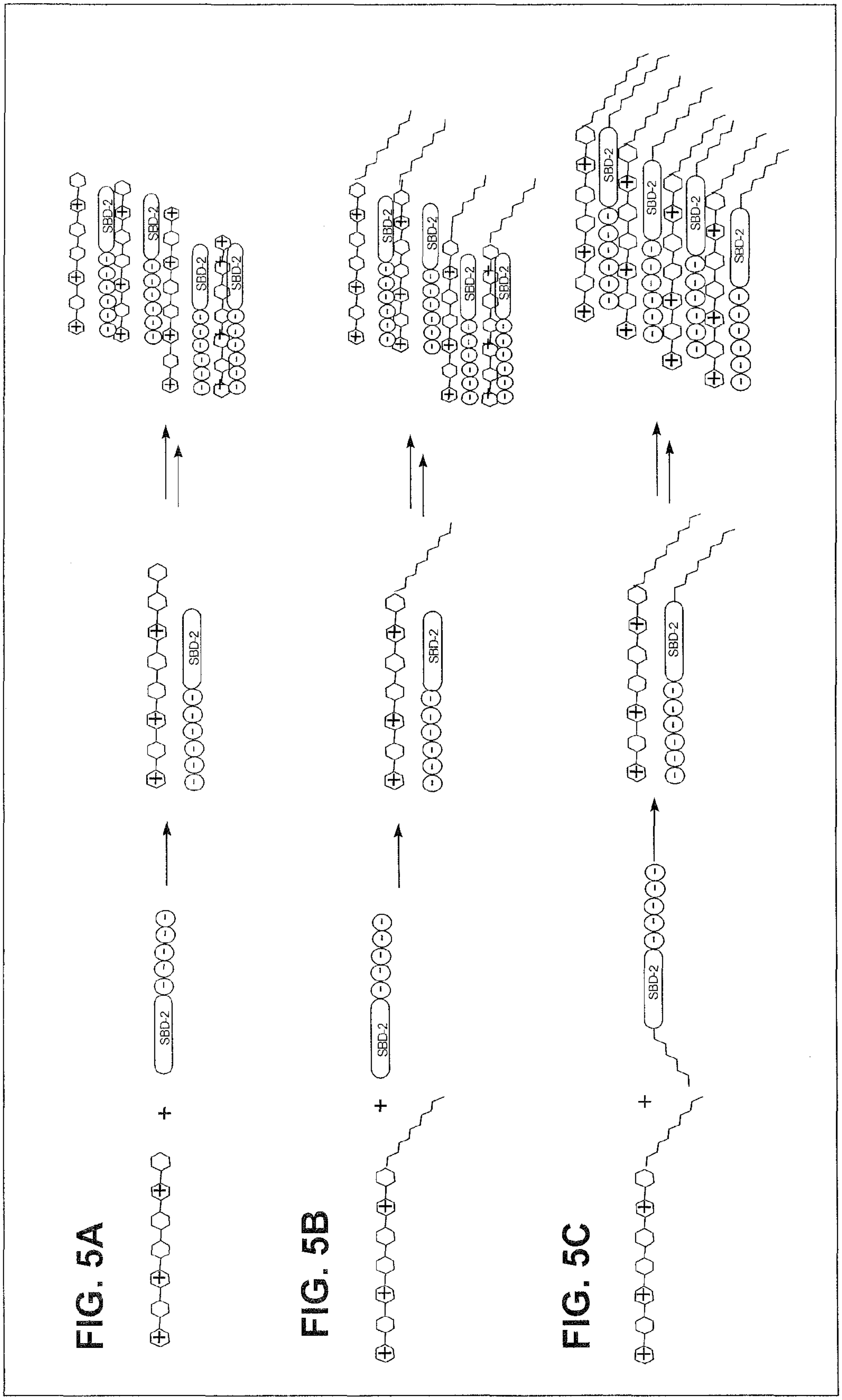
FIGS. 5A-5C are schematic diagrams showing 3 separate compositions of the presently disclosed subject matter.
Figures 6, 6A, 6B:
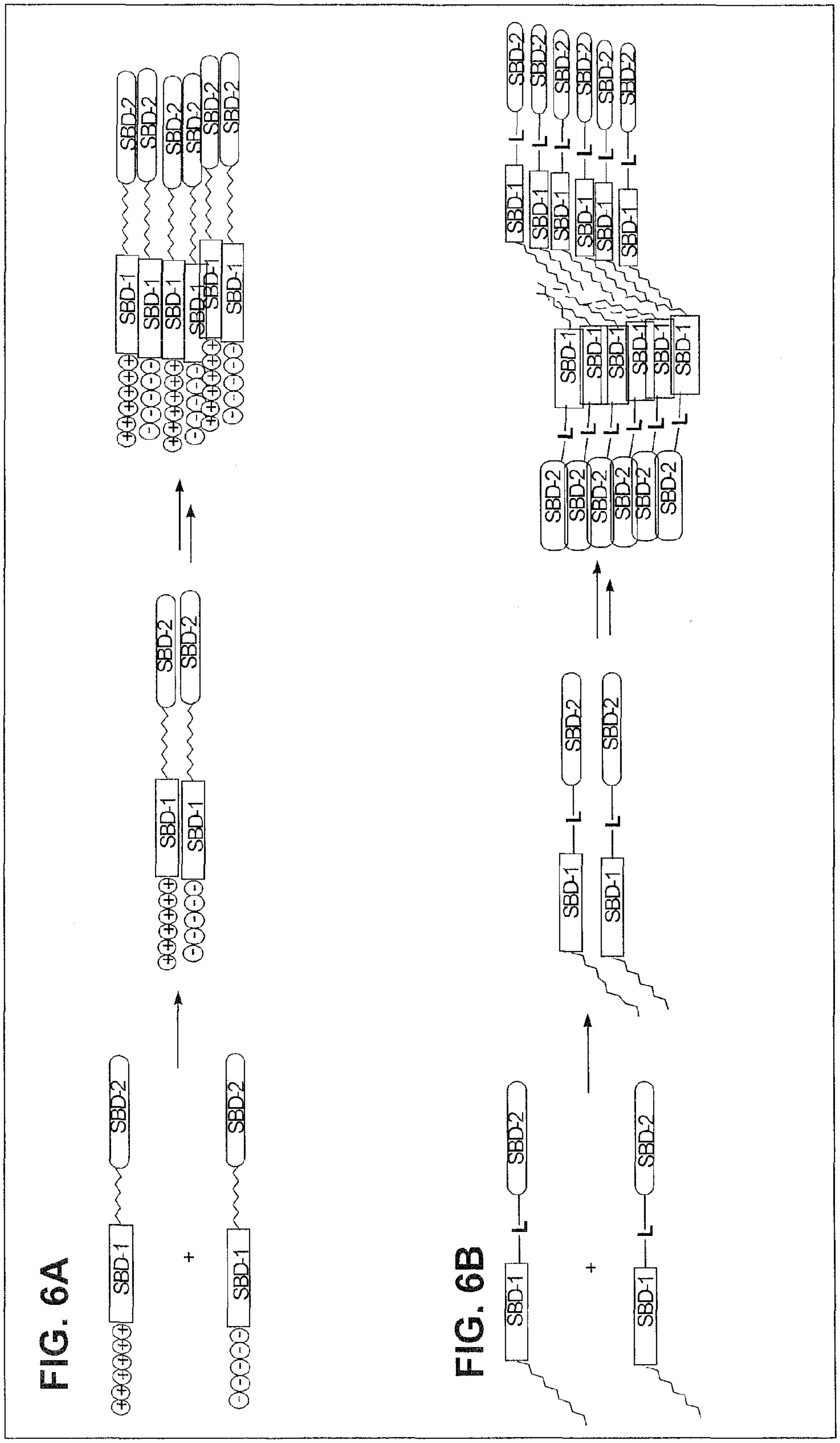
FIGS. 6A-6B are a schematic diagrams showing 3 separate compositions of the presently disclosed subject matter.

The substrate binding molecules depicted in FIGS. 6A-4B are not meant to attempt to describe every possible combination of covalently coupled interaction tag on a molecule comprising a covalently linked first and second substrate binding domain. For example, the molecule comprising the linked substrate binding domains can comprise any combination of one or more hydrophobic and charged interaction tag, as long as the combination allows for a plurality of molecules comprising the linked first and second substrate binding domains to form a non-covalent coupling with each other according to the rules of hydrophobic tags interacting with each other and charged interaction tags interacting with other oppositely charged interaction tags. One embodiment, for example, that is not depicted in FIGS. 6A-6C is the embodiment where each molecule comprising the linked first and second binding domains has both a charged and a hydrophobic interaction tag.

In some embodiments, the presently disclosed subject matter provides a composition comprising a plurality of a first substrate-binding peptide comprising 3 to 40 amino acids, wherein the first substrate is a tissue or medical device and the first substrate-binding peptide has binding affinity for the tissue or medical device; a plurality of a second substrate-binding peptide comprising 3 to 40 amino acids, wherein the second substrate is a target molecule and the second substrate-binding peptide has binding affinity for the target molecule, wherein the first and second substrate-binding peptides are covalently linked; and a plurality of the target molecule, wherein the plurality of covalently linked first and second substrate-binding peptides are covalently coupled to at least one interaction tag selected from the group consisting of a hydrophobic interaction tag, a positively charged interaction tag, and a negatively charged interaction tag, wherein the hydrophobic interaction tags interact with each other and the positively charged interaction tags interact with the negatively charged interaction tags to form a macromolecular network comprising the plurality of non-covalently coupled substrate-binding peptides.

In some embodiments, the first substrate tissue or medical device comprises a material selected from the group consisting of an animal tissue, an autologous tissue, an allogeneic tissue, a transplanted tissue, an organ tissue, a bone tissue, a skin tissue, a connective tissue, a muscle tissue, a nervous tissue, a polymer, a silk, a collagen, a synthetic polymer, a polyester, a polyurethane, a nylon, a polylactic acid, a polyglycolic acid, poly(lactic acid-co-glycolic acid), a plastic, a silicone material, a metal, a metal oxide, a non-metal oxide, a ceramic material, a calcium phosphate based material, a carbon-based material, a metallo-carbon composite, and combinations thereof.

In some embodiments, the target molecule is selected from the group consisting of a cell, a protein, a polypeptide, a growth factor, a growth differentiation factor (GDF), a platelet derived growth factor (PDGF), a transforming growth factor (TGF), an osteogenic protein, a bone morphogenic protein (BMP), a hormone, a protein hormone, a parathyroid hormone (PTH), a drug, a drug carrier, an antibiotic, a vancomycin antibiotic, a steroid, a dexamethasone, and combinations thereof.

In some embodiments, the charged interaction tag is selected from the group consisting of polylysine, polyarginine, polyamines, polyimines, polyethylamines, polyethylenimines (PEI), polyaspartic acid, polyglutamic acid, polystyrene sulfonate, poly(styrenesulfonic-maleic acid), and combinations and copolymers thereof. In some embodiments, the hydrophobic interaction tag is selected from the group consisting of fatty acids, undecanoic acid, poly-undecanoic acid, myristic acid, amino hexanoic acid, capric acid, lauric acid, palmitic acid, stearic acid, aromatic compounds, and combinations and copolymers thereof.

In some embodiments, the first and second substrate-binding peptides are covalently linked by a peptide bond. In some embodiments, the first and second substrate-binding domains are covalently linked through any one of the hydrophobic interaction tag, the charged interaction tag, amino acids, polymers, synthetic polymers, polyethers, poly(ethylene glycol) ("PEG"), a 10 unit polyethylene glycol ("P10"), and a 6 unit polyethylene glycol ("MP").

In some embodiments, the first substrate is a metal medical device, the second substrate target molecule is vancomycin, the first and second substrate binding peptides are covalently linked through a polyethylene glycol, the hydrophobic interaction tag is poly-undecanoic acid, the hydrophobic interaction tag is covalently coupled to the first substrate binding peptide either directly, through a polyethylene glycol, or through an aminohexanoic acid, and the charged interaction tag is absent.

In some embodiments, the first substrate is a metal medical device, the second substrate target molecule is vancomycin, the first and second substrate binding peptides are covalently linked through a polyethylene glycol, the positively charged interaction tag is covalently coupled to a portion of the plurality of second substrate binding peptide, the negatively charged interaction tag is covalently coupled to a portion of the second substrate binding peptide, and the hydrophobic interaction tag is absent.

In some embodiments, the first substrate medical device is a synthetic polymer, the second substrate target molecule is a growth factor, the hydrophobic interaction tag is poly-undecanoic acid, the first and second substrate binding peptides are covalently linked through the poly-undecanoic acid hydrophobic interaction tag, and the charged interaction tag is absent.

In some embodiments, the first substrate medical device is a synthetic polymer, the second substrate target molecule is a growth factor, the first and second substrate binding peptides are covalently linked through a polyethylene glycol, the hydrophobic interaction tag is poly-undecanoic acid, the poly-undecanoic acid is covalently coupled to the second substrate binding peptides, and the charged interaction tag is absent.

In another embodiment, the compositions used in the presently disclosed subject matter comprise a first substrate-binding peptide having binding affinity for a tissue or medical device covalently linked to a second substrate-binding peptide having binding affinity for a target molecule, another additional second substrate-binding peptide, and the target molecule vancomycin. Each of the covalently linked first and second substrate-binding peptide comprising molecules and the second substrate binding peptide molecules are covalently coupled to at least one interaction tag selected from the group consisting of a hydrophobic interaction tag, a positively charged interaction tag, and a negatively charged interaction tag. The covalently linked substrate-binding peptide molecules, the additional second substrate-binding domain comprising molecule, and the target molecules are combined resulting in the hydrophobic interaction tags interacting with each other and the charged interaction tags interacting with oppositely charged interaction tags. (see, for example, FIG. 7). In this manner, a macromolecular network is formed comprising the substrate-binding domain molecules non-covalently coupled together, and when combined with the target molecule and coated onto a tissue or medical device, the composition loads the target molecule onto the tissue or medical device. (see, e.g., FIG. 7 & Example 17). In some embodiments, the linked first and second substrate-binding domains, the additional second substrate binding domain, and the target molecule are present in a pharmaceutically acceptable solution. In some embodiments, the pharmaceutically acceptable solution is in the form of a gel. In some embodiments, the tissue or medical device is first coated with one or more of the linked first and second substrate binding domain comprising molecules, the additional second substrate binding domain comprising molecules, and the target molecules, rather than being coated after all the components are mixed together. The order of coating the tissue or medical device with the compositions comprising the substrate-binding domains and the target molecules can be varied.

Figure 7:
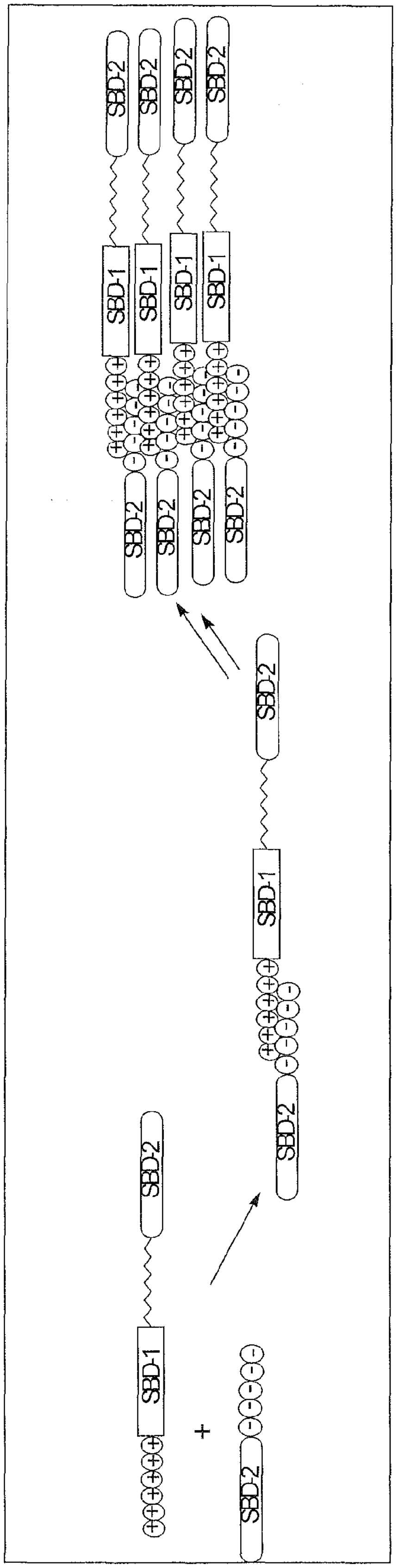
FIG. 7 is a schematic diagram showing a composition of the presently disclosed subject matter.

The substrate binding molecules depicted in FIG. 7 are not meant to be an attempt to describe every possible combination of covalently coupled interaction tag on the molecules comprising a covalently linked first and second substrate binding domains and the additional second substrate comprising domains. For example, the hydrophobic interaction tag covalently coupled to the molecule comprising the linked substrate binding domains can be coupled at a terminus rather than coupled so as to link the two substrate-binding domains as depicted. The molecule comprising the additional second substrate binding domain can also further comprise a hydrophobic interaction tag. In another example, both molecules can comprise hydrophobic interaction tags with the charged interaction tags being absent. Any combination of hydrophobic and/or charged interaction tags is acceptable, as long as the combination allows for a plurality of molecules comprising the linked first and second substrate binding domains and the additional second substrate binding domains to form a non-covalent coupling with each other according to the rules of hydrophobic tags interacting with each other and charged interaction tags interacting with other oppositely charged interaction tags.

In another embodiment, the presently disclosed subject matter provides a composition comprising a composition comprising, a plurality of first molecules comprising a first substrate-binding peptide comprising 3 to 40 amino acids, wherein the first substrate is a tissue or medical device and the first substrate-binding peptide has binding affinity for the tissue or medical device; and a second substrate-binding peptide comprising 3 to 40 amino acids, wherein the second substrate is a target molecule and the second substrate-binding peptide has binding affinity for the target molecule, wherein the first and second substrate-binding peptides are covalently linked; and a plurality of second molecules comprising the second substrate-binding peptide, wherein the second substrate binding peptide is not covalently linked to the first substrate binding peptide; and a plurality of the target molecule, wherein each of the plurality of first and second molecules are covalently coupled to at least one interaction tag selected from the group consisting of a hydrophobic interaction tag, a positively charged interaction tag, and a negatively charged interaction tag, wherein the hydrophobic interaction tags interact with each other and the positively charged interaction tags interact with the negatively charged interaction tags to form a macromolecular network comprising the plurality of non-covalently coupled first and second molecules.

In some embodiments, the first substrate tissue or medical device comprises a material selected from the group consisting of an animal tissue, an autologous tissue, an allogeneic tissue, a transplanted tissue, an organ tissue, a bone tissue, a skin tissue, a connective tissue, a muscle tissue, a nervous tissue, a polymer, a silk, a collagen, a synthetic polymer, a polyester, a polyurethane, a nylon, a polylactic acid, a polyglycolic acid, poly(lactic acid-co-glycolic acid), a plastic, a silicone material, a metal, a metal oxide, a non-metal oxide, a ceramic material, a calcium phosphate based material, a carbon-based material, a metallo-carbon composite, and combinations thereof.

In some embodiments, the target molecule is selected from the group consisting of a cell, a protein, a polypeptide, a growth factor, a growth differentiation factor (GDF), a platelet derived growth factor (PDGF), a transforming growth factor (TGF), an osteogenic protein, a bone morphogenic protein (BMP), a hormone, a protein hormone, a parathyroid hormone (PTH), a drug, a drug carrier, an antibiotic, a vancomycin antibiotic, a steroid, a dexamethasone, and combinations thereof.

In some embodiments, the charged interaction tag is selected from the group consisting of polylysine, polyarginine, polyamines, polyimines, polyethylamines, polyethylenimines (PEI), polyaspartic acid, polyglutamic acid, polystyrene sulfonate, poly(styrenesulfonic-maleic acid), and combinations and copolymers thereof. In some embodiments, the hydrophobic interaction tag is selected from the group consisting of fatty acids, undecanoic acid, poly-undecanoic acid, myristic acid, amino hexanoic acid, capric acid, lauric acid, palmitic acid, stearic acid, aromatic compounds, and combinations and copolymers thereof.

In some embodiments, the first and second substrate-binding peptides are covalently linked through a peptide bond. The composition of claim 5, wherein the first and second substrate-binding domains are covalently linked by any one of the hydrophobic interaction tag, the charged interaction tag, amino acids, polymers, synthetic polymers, polyethers, poly(ethylene glycol) ("PEG"), a 10 unit polyethylene glycol ("P10"), and a 6 unit polyethylene glycol ("MP").

In some embodiments, the first substrate is a metal medical device, the second substrate target molecule is vancomycin, the first and second substrate-binding peptides are covalently linked through the poly-undecanoic acid hydrophobic interaction tag, and each of the first and the second molecules comprise a covalently coupled charged interaction tag wherein the charged interaction tag on the first molecules is oppositely charged to the charged interaction tag on the second molecules.

In some embodiments, the first substrate is a metal medical device, the second substrate target molecule is vancomycin, the hydrophobic interaction tag is poly-undecanoic acid and is covalently coupled to the first molecules, and each of the first and the second molecules comprise a covalently coupled charged interaction tag, wherein the charged interaction tag on the first molecules is oppositely charged to the charged interaction tag on the second molecules. Also provided in the presently disclosed subject matter are methods for applying the compositions of presently disclosed subject matter to a substrate that is tissue or a medical device, the methods comprising contacting the composition with the substrate so that the composition binds the substrate, such as in forming a coating on the substrate which has one or more improved biophysical properties. Also provided in the presently disclosed subject matter are medical devices coated with the compositions of the presently disclosed subject matter, wherein at least a portion of the medical device is coated with the composition.

Example 1

While substrate-binding peptides can be identified using any one of several methods known to those skilled in the art, Illustrated in this example are various methods for utilizing phage display technology to produce a substrate-binding peptide having binding specificity for substrate, such substrate-binding peptide useful as a component in producing a compound according to the present invention.

Phage Screening and Selections.

Phage display technology is well-known in the art, and can be used to identify additional peptides for use as binding domains in the compositions according to the present invention. In general, using phage display, a library of diverse peptides can be presented to a target substrate, and peptides that specifically bind to the substrate can be selected for use as binding domains. Multiple serial rounds of selection, called "panning," may be used. As is known in the art, any one of a variety of libraries and panning methods can be employed to identify a binding domain that is useful in a composition according to the present invention. Panning methods can include, for example, solution phase screening, solid phase screening, or cell-based screening. Once a candidate binding domain is identified, directed or random mutagenesis of the sequence may be used to optimize the binding properties (including one or more of specificity and avidity) of the binding domain.

For example, a variety of different phage display libraries were screened for peptides that bind to a selected target substrate (e.g., a substrate selected to find a binding domain useful in the present invention). The substrate was either bound to or placed in (depending on the selected substrate) a container (e.g., wells of a 96 well microtiter plate, or a microfuge tube). Nonspecific binding sites on the surfaces of the container were blocked with a buffer containing bovine serum albumin ("BSA"; e.g., in a range of from 1% to 10%). The containers were then washed 5 times with a buffer containing buffered saline with Tween™ 20 ("buffer-T"). Each library was diluted in buffer-T and added at a concentration of $10^{10}$ pfu/ml in a total volume of 100 µl. After incubation (in a range of from 1 to 3 hours) at room temperature with shaking at 50 rpm, unbound phage were removed by multiple washes with buffer-T. Bound phage were used to infect *E. coli* cells in growth media. The cell and phage-containing media was cultured by incubation overnight at 37° C. in a shaker at 200 rpm. Phage-containing supernatant was harvested from the culture after centrifuging the culture. Second and third rounds of selection were performed in a similar manner to that of the first round of selection, using the amplified phage from the previous round as input. To detect phage that specifically bind to the selected substrate, enzyme-linked immunosorbent (ELISA-type) assays were performed using an anti-phage antibody conjugated to a detector molecule, followed by the detection and quantitation of the amount of detector molecule bound in the assay. The DNA sequences encoding peptides from the phage that specifically bind to the selected substrate were then determined; i.e., the sequence encoding the peptide is located as an insert in the phage genome, and can be sequenced to yield the corresponding amino acid sequence displayed on the phage surface.

Example 2

As summarized previously herein, the compound useful in making a composition of the invention is comprised of fatty acid covalently coupled to substrate-binding peptide. The composition may comprise substrate-binding peptide of a single type (e.g., "type" defined by the substrate for which the substrate-binding peptide has binding specificity), or may comprise more than one type of substrate-binding peptide. Further, as illustrated and described in more detail in Examples 4 & 5 herein, the peptide component of the compound may comprise a peptide comprised of a single binding specificity (see, e.g., Example 4); or may comprise two or more binding domains, with each binding domain comprised of a substrate-binding peptide, and with the two or more binding domains covalently coupled (directly or via a linker) (see, e.g., Example 5).

In one example, the substrate, for which a substrate comprising a material comprising a surface of a device, and more preferably a medical device; wherein the material is selected from the group consisting of a metal, a polymer, a non-metal oxide, and a ceramic. As a specific illustrative example for developing substrate-binding peptides using the methods outlined in Example 1, and to develop substrate-binding peptides having binding specificity for polymer, various polymers were used as a substrate for performing phage selection using several different libraries of phage. Table 1 illustrates exemplary substrate-binding peptides, which may be used in the compounds and compositions according to the present invention, having binding specificity for a polymer, and comprise: SEQ ID NOs:1-22 that have binding specificity for polystyrene; SEQ ID NO:23 that has binding specificity for polyurethane; SEQ ID NOs: 24-37 that have binding specificity for polyglycolic acid; SEQ ID NOs: 38-43 that have binding specificity for polycarbonate; SEQ ID NOs: 44-52 that have binding specificity for nylon; and SEQ ID NOs: 53 and 54 that have binding specificity for teflon. Such peptides may be used as substrate-binding peptides having binding specificity for non-biological substrate comprising a polymer to which they having binding specificity.

TABLE 1

| SEQ ID NO: | Amino acid sequence (single letter code) |
|---|---|
| | Binding specificity for polystyrene |
| 1 | FLSFVFPASAWGG |
| 2 | FYMPFGPTWWQHV |
| 3 | LFSWFLPTDNYPV |
| 4 | FMDIWSPWHLLGT |
| 5 | FSSLFFPHWPAQL |
| 6 | SCAMAQWFCDRAEPHHVIS |

TABLE 1-continued

| SEQ ID NO: | Amino acid sequence (single letter code) |
|---|---|
| 7 | SCNMSHLTGVSLCDSLATS |
| 8 | SCVYSFIDGSGCNSHSLGS |
| 9 | SCSGFHLLCESRSMQRELS |
| 10 | SCGILCSAFPFNNHQVGAS |
| 11 | SCCSMFFKNVSYVGASNPS |
| 12 | SCPIWKYCDDYSRSGSIFS |
| 13 | SCLFNSMKCLVLILCFVS |
| 14 | SCYVNGHNSVWVVVFWGVS |
| 15 | SCDFVCNVLFNVNHGSNMS |
| 16 | SCLNKFFVLMSVGLRSYTS |
| 17 | SCCNHNSTSVKDVQFPTLS |
| 18 | FFPSSWYSHLGVL |
| 19 | FFGFDVYDMSNAL |
| 20 | LSFSDFYFSEGSE |
| 21 | FSYSVSYAHPEGL |
| 22 | LPHLIQYRVLLVS |
| | Binding specificity for polyurethane |
| 23 | SCYVNGHNSVWVVVFWGVS |
| | Binding specificity of polyglycolic acid |
| 24 | SCNSFMFINGSFKETGGCS |
| 25 | SCFGNLGNLIYTCDRLMPS |
| 26 | SCSFFMPWCNFLNGEMAVS |
| 27 | SCFGNVFCVYNQFAAGLFS |
| 28 | SCCFINSNFSVMNHSLFKS |
| 29 | SCDYFSFLECFSNGWSGAS |
| 30 | SCWMGLFECPDAWLHDWDS |
| 31 | SCFWYSWLCSASSSDALIS |
| 32 | SCFGNFLSFGFNCESALGS |
| 33 | SCLYCHLNNQFLSWVSGNS |
| 34 | SCFGFSDCLSWFVQPSTAS |
| 35 | SCNHLGFFSSFCDRLVENS |
| 36 | SCGYFCSFYNYLDIGTASS |
| 37 | SCNSSSYSWYCWFGGSSPS |
| | Binding specificity for polycarbonate |
| 38 | FGHGWLNTLNLGW |
| 39 | FSPFSANLWYDMF |
| 40 | VFVPFGNWLSTSV |
| 41 | FWNVNYNPWGWNY |

TABLE 1-continued

| SEQ ID NO: | Amino acid sequence (single letter code) |
|---|---|
| 42 | FYWDRLNVGWGLL |
| 43 | LYSTMYPGMSWLV |
| | Binding specificity for nylon |
| 44 | SCFYQNVISSSFAGNPWEC |
| 45 | SCNMLLNSLPLPSEDWSAC |
| 46 | SCPFTHSLALNTDRASPGC |
| 47 | SCFESDFPNVRHHVLKQSC |
| 48 | SCVFDSKHFSPTHSPHDVC |
| 49 | SCGDHMTDKNMPNSGISGC |
| 50 | SCDFFNRHGYNSGCEHSVC |
| 51 | SCGDHMTDKNMPNSGISGC |
| 52 | SCYYNGLVVHHSNSGHKDC |
| | Binding specificity for Teflon |
| 53 | CWSRFRLFMLFCMFYLVS |
| 54 | CIKYPFLYCCLLSLFLFS |

As a specific illustrative example for developing substrate-binding peptides using the methods outlined in Example 1, and to develop substrate-binding peptides having binding specificity for metal, metal (e.g., titanium or stainless steel) was used as a substrate for performing phage selection using several different libraries of phage. Titanium beads and stainless steel beads of approximately 5/32-inch diameter were individually prepared for selections by sequentially washing the beads with 70% ethanol, 40% nitric acid, distilled water, 70% ethanol and, finally, acetone, to remove any surface contaminants. After drying, one metal bead was placed per well of a 96-well polypropylene plate. Non-specific binding sites on the metal beads and the surface of the polypropylene plate were blocked with 1% bovine serum albumin (BSA) in phosphate-buffered saline (PBS). The plate was incubated for 1 hour at room temperature with shaking at 50 rpm. The wells were then washed 5 times with 300 μL of buffer-T.

Each library was diluted in buffer-T and added at a concentration of $10^{10}$ pfu/mL in a total volume of 100 μL. After 3 hours of incubation at room temperature and shaking at 50 rpm, unbound phage were removed by 5 washes of buffer-T. The phage were added directly to *E. coli* DH5αF' cells in 2×YT media, and the phage-infected cells were transferred to a fresh tube containing 2×YT media and incubated overnight at 37° C. in a shaker incubator. Phage supernatant was harvested by centrifugation at 8500×g for 10 minutes. Second and third rounds of selection were performed in a similar manner to the first round, using the amplified phage from the previous round as input. Each round of selection was monitored for enrichment of metal binding peptides using ELISA-like assays performed using an anti-M13 phage antibody conjugated to horseradish-peroxidase, followed by the addition of chromogenic agent ABTS (2,2'-azino-bis(3-ethylbenzthiazoline-6-sulphonic acid), and determining a read-out at 405 nm. Libraries that showed enrichment of phage displaying metal binding peptides were plated on a lawn of *E. coli* cells, and individual plaques were picked and tested for binding to metals (e.g., titanium, stainless steel, etc.). Relative binding strengths of the phage can also be determined by testing serial dilutions of the phage for binding to a metal substrate in an ELISA. For example, serial dilutions of the display-selected clones were exposed to titanium or steel in an ELISA. The higher dilutions represent more stringent assays for affinity; therefore, phage that yield a signal at higher dilutions represent peptides with higher relative affinity for the particular target metal. Primers against the phage vector sequence that flank the insertion site were used to determine the DNA sequence encoding the peptide for the phage in each group. The sequence encoding the peptide insert was translated to yield the corresponding amino acid sequence displayed on the phage surface. Similar procedures were used to develop surface-binding peptides that have binding specificity for polymers.

The DNA sequences encoding peptides isolated on either polymer substrates or metal substrates were determined. While typically such phage amino acids adjoining the peptide displayed had no significant contribution to the binding specificity of the peptide, the peptides useful in the present invention may also comprise, in their amino acid sequence, such phage amino acids adjoining the peptide at the N-terminus and at the C-terminus (e.g., denoted as ss and sr in Table 2).

Binding Specificity Characterizations

Relative binding strengths (affinities) of the substrate-binding peptides to a substrate, also used as a measure of binding specificity, were determined by testing serial dilutions of the substrate-binding peptides for binding to a target substrate (e.g., comprising either metal or polymer, depending on the substrate-binding peptide's binding specificity being characterized). Plotting the absorbance observed across the concentration range for each peptide sequence yielded a binding curve of the peptides to its target substrate from which can be determined an EC50 (e.g., the concentration of peptide that gives 50% of the maximum signal in the binding curve is used as an estimate of the affinity of the peptide for the target). Preferred for use in a compound or composition according to the present invention are substrate-binding peptides that bind to the selected substrate with binding specificity, preferably with an EC50 of less than or equal to about 1 μM, and more preferably, in the nanomolar range (e.g., <0.1 μM). A typical binding assay for titanium (note, a different substrate may be substituted for titanium in the assay, depending on the binding specificity of the substrate-binding peptide) may be performed according to the following procedure.

Briefly, 5/32-inch diameter Grade 200 titanium beads were washed by sonication in acetone for 15 minutes, and the beads were allowed to dry. One bead was added to each well of a 96-well polypropylene plate. Two hundred fifty (250) μL of 1% BSA in PBS was added to each well of the plate. The surface of the wells and the beads were blocked by incubation for 1 hour at 20° C. with shaking at 500 rpm. The plate was washed three times with 250 μL of buffer-T per well. A 1:3 dilution series of each of the peptides was prepared using PBS as a diluent, starting at a peptide concentration of 20 μM, and going down to 0.0001 μM. A 200 μL sample of each dilution was added to wells of the plate. The plate was incubated for 1 hour at 20° C. with shaking at 500 rpm. The beads were washed three times with 250 μL of buffer-T per well. Two hundred (200) μL of streptavidin-alkaline phosphatase ("streptavidin AP") reagent, at a dilution of 1:2000 in buffer +1% BSA, was added to each well. The plate was incubated for 30 minutes at room temperature. The beads were washed three times with 250 μL of buffer-T per well. Two hundred (200) μL of color development reagent (PNPP, p-nitrophenol phosphate) was added to each well. After color had developed (10 minutes), the samples were transferred to a clear 96-well plate and the absorbance at 405 nm determined. A binding curve was generated by plotting the absorbance at 405 nm against the peptide concentration (μM). Table 2 illustrates exemplary substrate-binding peptides, which may be used in producing a compound or composition according to the present invention, having binding specificity for a metal (including a metal alloy, a metal oxide, or a non-metal oxide), and comprising: SEQ ID NOs:55-82 that specifically bind to titanium; and SEQ ID NOs: 83-102 that specifically bind to stainless steel.

TABLE 2

| SEQ ID NO: | Amino acid sequence (single letter code) |
|---|---|
| | Binding specificity for titanium |
| 55 | SCFWFLRWSLFIVLFTCCS |
| 56 | SCESVDCFADSRMAKVSMS |
| 57 | SCVGFFCITGSDVASVNSS |
| 58 | SCSDCLKSVDFIPSSLASS |
| 59 | SCAFDCPSSVARSPGEWSS |
| 60 | SCVDVMHADSPGPDGLNS |
| 61 | SCSSFEVSEMFTCAVSSYS |
| 62 | SCGLNFPLCSFVDFAQDAS |
| 63 | SCMLFSSVFDCGMLISDLS |
| 64 | SCVDYVMHADSPGPDGLNS |
| 65 | SCSENFMFNMYGTGVCTES |
| 66 | HKHPVTPRFFVVE |
| 67 | CNCYVTPNLLKHKCYKIC |
| 68 | CSHNHHKLTAKHQVAHKC |
| 69 | CDQNDIFYTSKKSHKSHC |
| 70 | SSDVYLVSHKHHLTRHNS |
| 71 | SDKCHKHWYCYESKYGGS |
| 72 | SDKSHKHWYSYESKYGGS |
| 73 | HHKLKHQMLHLNGG |
| 74 | GHHHKKDQLPQLGG |
| 75 | ssHKHPVTPRFFVVEsr |
| 76 | ssCNCYVTPNLLKHKCYKICsr |
| 77 | ssCSHNHHKLTAKHQVAHKCsr |
| 78 | ssCDQNDIFYTSKKSHKSHCsr |
| 79 | ssSSDVYLVSHKHHLTRHNSsr |
| 80 | ssSDKCHKHWYCYESKYGGSsr |
| 81 | HHKLKHQMLHLNGG |
| 82 | GHHHKKDQLPQLGG |

TABLE 2-continued

| SEQ ID NO: | Amino acid sequence (single letter code) |
|---|---|
| | Binding specificity for steel |
| 83 | CFVLNCHLVLDRP |
| 84 | SCFGNFLSFGFNCEYALGS |
| 85 | DGFFILYKNPDVL |
| 86 | NHQNQTN |
| 87 | ATHMVGS |
| 88 | GINPNFI |
| 89 | TAISGHF |
| 90 | LYGTPEYAVQPLR |
| 91 | CFLTQDYCVLAGK |
| 92 | VLHLDSYGPSVPL |
| 93 | VVDSTGYLRPVST |
| 94 | VLQNATNVAPFVT |
| 95 | WWSSMPYVGDYTS |
| 96 | SSYFNLGLVKHNHVRHHDS |
| 97 | CHDHSNKYLKSWKHQQNC |
| 98 | SCKHDSEFIKKHVHAVKKC |
| 99 | SCHHLKHNTHKESKMHHEC |
| 100 | VNKMNRLWEPL |
| 101 | SSHRTNHKKNNPKKKNKTR |
| 102 | NHTISKNHKKKNKNSNKTR |

While these exemplary peptide sequences are disclosed herein, one skilled in the art will appreciate that the deletions, additions or substitutions of these peptides may be made using methods known in the art, provided the resultant amino acid sequence retains substantially the binding properties as the exemplary peptide disclosed herein. For example, based on the amino acid sequences of substrate-binding peptides illustrated by SEQ ID NOs:75-82 in Table 2, shown in Table 3 is a series of synthetic, second-generation peptides which were synthesized, some of which had improved binding specificities as compared to the binding specificity of the peptide from which it was derived.

TABLE 3

| SEQ ID NO: | Amino acid sequence |
|---|---|
| 103 | SKKHGGKKHGSSGK |
| 104 | SKHKGGKHKGSSGK |
| 105 | SHKHGGHKHGGHKHGSSGK |
| 106 | SKHKGGHKHGSSGK |
| 107 | SHKHGGKHKGSSGK |
| 108 | SKHKGGGGKHKGSSGK |
| 109 | SHKHGGGGHKHGSSGK |

TABLE 3-continued

| SEQ ID NO: | Amino acid sequence |
|---|---|
| 110 | SHKHGGHKHGSSGK |
| 111 | SHHKGGHHKGSSGK |
| 112 | SKHKGGKHKGGKHKGSSGK |

Several oligomers (also referred to as "multimers") of different substrate-binding peptides were synthesized. Briefly, the oligomers were built on a lysine MAP core and comprised of two and four peptide modules, respectively, of a substrate-binding peptide. In an illustrative example, this core matrix was used to generate a peptide dimer and peptide tetramer using, in each branch, a monomeric peptide consisting essentially of the amino acid sequence of SEQ ID NO:112. The oligomers were synthesized sequentially using solid phase chemistry on a peptide synthesizer. The synthesis was carried out at a 0.05 mmol scale which ensures maximum coupling yields during synthesis. The biotin reporter moiety was placed at the C-terminus of the molecule, and was appended by a short linker containing glycine and serine residues to the lysine core. Standard Fmoc/t-Bu chemistry was employed using AA/HBTU/HOBt/NMM (1:1:1:2) as the coupling reagents (AA is amino acid; HOBt is O-Pfp ester/1-hydroxy-benzotriazole; HBTU is N-[1H-benzotriazol-1-yl)(dimethylamino) methylene]-N-methylmethanaminium hexafluorophosphate N-oxide; NMM is N-methylmorpholine). Amino acids were used in 5-10 fold excess in the synthesis cycles, and all residues were doubly, triply or even quadruply coupled depending upon the complexity of residues coupled. The coupling reactions were monitored by Kaiser ninhydrin test. The Fmoc deprotection reactions was carried out using 20% piperidine in dimethyl-formamide. Peptide cleavage from the resin was accomplished using trifluoracetic acid (TFA: $H_2O$:Triisopropylsilane=95: 2.5: 2.5) at room temperature for 4 hours. The crude product was precipitated in cold ether. The pellet obtained after centrifugation was washed thrice with cold ether and lyophilized to give a white solid as crude desired product. The crude products were analyzed by analytical high performance liquid chromatography (HPLC) on a C-18 column using mobile eluants (A=$H_2O$/TFA (0.1% TFA) and B=Acetonitrile/TFA (0.1% TFA). The polymers were also further analyzed by mass spectrometry for before subjecting each to final purification by HPLC. The fractions containing the desired product were pooled and lyophilized to obtain a fluffy white powder (>98% purity).

Example 3

Substrate-binding peptides, which bind to a biological substrate, can be used to produce a compound according to the invention. Thus, a fatty acid may be covalently coupled to a substrate-binding peptide having binding specificity for a biological substrate, whether it is a substrate-binding peptide by itself, or forms part of a biofunctional composition comprised of two or more substrate-binding peptides, wherein two or more substrate-binding peptides are covalently coupled together to form the biofunctional composition. For example, the biological substrate may comprise a biological molecule. In an illustrative example, wherein the biological molecule is a protein, and may further comprise a growth factor, disclosed is a substrate-binding peptide having binding specificity for BMP. For example, disclosed in commonly owned U.S. patent application US 20060051396 are families of peptides having binding specificity for BMP; one example being a peptide comprising the consensus amino acid sequence of GGALGFPLKGEVVEGWA (SEQ ID NO:113). In another example, wherein the biological substrate comprises a tissue, disclosed in commonly owned U.S. application 60/914341 are bone-trophic peptides; one example being a peptide comprising the amino acid sequence of FDIDWSGMRSWWG (SEQ ID NO:114). In another embodiment, wherein the biological substrate comprises a tissue, disclosed in published US applications US20030152976, US20050249682, and PCT application WO2006/094093 are skin-binding peptides, with one example of a peptide given as LSPSRMK (SEQ ID NO:115). In a further embodiment, wherein the biological substrate comprises a tissue, disclosed in commonly owned US60/972,277 are families of hair-binding peptides, with one example as a peptide comprising an amino acid sequence of SRKSSQKNPHHPKPPKKPTAR (SEQ ID NO:116). In another embodiment, wherein the biological substrate comprises a cell (preferably, cells of a cell type), a peptide having a sequence of ALPSTSSQMPQL (SEQ ID NO:117) has been described as binding to stem cells; and a peptide comprising the amino acid sequence of SSSCQHVSLLRPSAALGPDNCSR (SEQ ID NO:118) has binding specificity for human adipose-derived stem cells and endothelial cells (disclosed in commonly owned U.S. application Ser. No. 11/649,950).

In another embodiment, the substrate (either biological or non-biological, as the case may be) comprises a therapeutic drug. For example, it has been reported that by use of phage display to screen for peptides that bind to paclitaxel (trade name Taxol®), identified was a peptide having the amino acid sequence of HTPHPDASIQGV (SEQ ID NO: 119). In another embodiment where the substrate comprises a therapeutic drug, the therapeutic drug may comprise an antimicrobial. For example, vancomycin and vancomycin analogs bind to bacterial cell wall peptides ending with D-Ala-D-Ala (two D-alanine residues). A peptide that mimics bacterial cell wall peptide binding to vancomycin, and therefore binds to vancomycin and its analogs, comprises an amino acid sequence of Lys-Ala-Ala (L-Lys-D-Ala-D-Ala). In another embodiment, the biological substrate comprises a hormone. Thus, a substrate-binding peptide may having binding specificity for a hormone. For example, peptides having a core amino acid sequence of VMNV (SEQ ID NO: 120) have been described as binding to human growth hormone. In another embodiment, the biological molecule comprises a nucleic acid molecule, and more preferably, a nucleic acid molecule encoding a protein. For example, peptide having the amino acid sequence of AEDG (SEQ ID NO: 121) complexes with duplex DNA comprising [poly (dA-dT): poly(dA-dT)].

Example 4

Using the methods of the present invention described herein, a compound according to the present invention may be formed by covalently coupling one or more molecules of fatty acid to a substrate-binding peptide. In this example, illustrated are compounds formed by covalently coupling fatty acid to substrate-binding peptides having binding specificity for a non-biological substrate. Shown in Table 4 are illustrative compounds of the invention, synthesized by the methods described herein. The compounds are listed as a linear sequence, with "AUD" representing aminoundecanoic acid, "MYR" representing myristic acid; "PALM" representing palmitic acid; "LAU" representing lauric acid; "K" is single letter designation for lysine; "Y" is single letter designation for tyrosine; "R" is single letter designation for arginine; brackets "[ ]" around a fatty acid indicate the fatty acid is branched on a lysine; and "Ac" means a modified N-terminal amino acid which has been acetylated. A peptide comprising an amino acid sequence of SEQ ID NO:101, and having binding specificity for metal, was synthesized to further include a linker at the C-terminal end to be biotinylated to facilitate detection during functional studies. Such peptide is represented by the amino acid sequence SSHRTNHKKNNPKKKNKTRGSSGK (SEQ ID NO:122).

TABLE 4

| Compound Ref. # | Compound linear sequence |
|---|---|
| 122 | AUD-AUD-AUD-AUD-SEQ ID NO: 122 |
| 123 | AUD-AUD-K-AUD-AUD-AUD-AUD-SEQ ID NO: 122 |
| 124 | AUD-AUD-AUD-AUD-AUD-AUD-SEQ ID NO: 122-RRRRRRR |
| 125 | MYR-SEQ ID NO: 122 |
| 126 | LAU-SEQ ID NO: 122 |
| 127 | MYR-linker-SEQ ID NO: 122 |
| 128 | $[MYR]_2$-K-linker-SEQ ID NO: 122 |
| 129 | PALM-PALM-PALM-linker-SEQ ID NO: 122 |
| 130 | AUD-AUD-AUD-AUD-AUD-AUD-SEQ ID NO: 122 |
| 131 | AUD-AUD-AUD-AUD-AUD-AUD-AUD-AUD-SEQ ID NO: 122 |
| 132 | Ac-Y-AUD-AUD-AUD-AUD-AUD-AUD-SEQ ID NO: 122 |

The following acronyms are used in the description of methods for making compounds of the invention (see, e.g., Examples 4 & 5).

Mtt is 4-methyltrityl; TATU is 2-(7-Aza-1H-Benzotriazole-1-yl)-1,1,3,3-tetramethyluronium tetrafluoroborate; DIEA is diisopropylethylamine; NMP is 1-Methyl-2-pyrrolidone; DCM is dichloromethane; DMF is dimethylformamide; TFA is trifluoracetic acid; TIS is triisopropylsilane; TBTU is O-(Benzotriazol-1-yl)-N,N,N',N'-tetramethyluronium tetrafluoroborate; HOBt is O-Pfp ester/1-hydroxybenzotriazole; NMM is N-methylmorpholine; RP-HPLC is reverse phase high performance liquid chromatography; Fmoc is 9-fluorenylmethoxycarbonyl; tBU is t-butyl; mini-PEG is Fmoc-8-Amino-3,6-Dioxaoctanoic Acid; MALDI-TOF is matrix-assisted laser desorption ionization-time of flight mass spectrometry; Reagent A is water/TFA (0.1% TFA); Reagent B is Acetonotrile/TFA (0.1% TFA); Fmoc-PAL-PEG resin is [5-(4-Fmoc-aminomethyl-3,5-dimethoxyphenoxy) valeric acid]-polyethylene glycol-polystryrene resin.

Compound 125 and compound 126 were synthesized by coupling 150 mg of a 'universal' SSHRTNHKKNNPKKKNKTRGSSGK(Mtt)-resin (the amino acid sequence being that of SEQ ID NO:122) with 1 mmol of myristic and lauric acid, respectively, using TATU/2 mmol DIEA in NMP for 2 hours. Following coupling, the resin was washed with NMP (3 times) and DCM (5 times) and dried under vacuum overnight. The dried resin was subjected to cleavage using TFA cocktail (3 mL) comprised of 2.5% (v/v) each of water and TIS in TFA. After cleavage for 1.5 hours, the reaction was filtered into 25 mL of cold ether. The pellet obtained was separated by centrifugation, and then washed with chilled ether (3×). The crude product was air-dried and purified by RP-HPLC using the following conditions: Column: C-18 (250×21.2 mm). Flow: 10 mL/min. Gradient: 0-20% Reagent B in 1 minute; 20-60% Reagent B in 30 minutes. The fractions containing the desired product were pooled and lyophilized to obtain a fluffy white powder (>95% purity). Compound 125 was purified (HPLC retention time of 15.32 minutes (0 to 60% Reagent B in 30 minutes @ 0.075 mL/min at 220 nm)); and characterized by MALDI-TOF (observed mass=2929.2; expected mass=2929.39). Compound 126 was purified (HPLC retention time of 12.63 min (0 to 60% Reagent B in 30 minutes @ 0.075 mL/min at 220nm)), and characterized by MALDI-TOF (observed mass=2901; expected mass=2901.34).

Compounds 127, 128 and 129 were synthesized using standard Fmoc/tBu chemistry. Foc-Lys(Biotin) was introduced at the C-terminus by coupling to Fmoc-PAL-PEG-PS resin. Linear synthesis was performed to synthesize the peptide component of the compound (SSHRTNHKKNNPKKKNK-TRGSSGK; SEQ ID NO:122). Amino acids were used in 5 fold excess in the synthesis cycles, and all residues were doubly or triply coupled. The coupling reactions were monitored by Kaiser ninhydrin test or chloranil test. Fmoc deprotection reactions were carried out using 20% piperidine in DMF. A mini-PEG linker was introduced between the peptide and fatty acid moieties, in covalently coupling fatty acid to peptide. Myristic acid was pre-activated with HOBt, and double coupled to the resin using the TBTU/HOBt/NMM method. For compound 128 synthesis, Fmoc-Lys(Fmoc)-OH was coupled to mini-PEG linker. The two terminal Fmoc groups were removed, followed by coupling with 10 equivalents of myristic acid using the TBTU method. For compound 129 synthesis, 5 fold excess of palmitoyl-Cys((RS)-2,3-di (palmitoyloxy)-propyl)-OH was double coupled to mini-PEG-peptide resin using TBTU activation.

Following synthesis, the resin containing the compound was cleaved using TFA cocktail (2.5% water; 2.5% TIS; 95% TFA) for 4 hours. The cleavage reaction mixture was filtered into cold ether. The pellet obtained was further washed thrice with cold ether, and dried under vacuum. The crude products were purified using RP-HPLC (column: C-4, 250×21.2 mm; Flow: 10 mL/minute Gradient: 0-20% Reagent B in 1 minute; 20-80% Reagent B in 30 minutes. Compound 127 was purified (HPLC retention time of 14.63 minutes (30 to 60% B in 30 minutes @ 1 mL/min at 220nm)) and characterized by MALDI-TOF (observed mass=3300; expected mass=3300.86). Compound 128 was purified (HPLC retention time of 24.25 minutes (40 to 65% Reagent B in 30 minutes @ 1 mL/min at 220 nm)), and characterized by MALDI-TOF (observed mass=3638.5; expected mass=3639.32). Compound 129 was characterized by MALDI-TOF (observed mass=3981.8; expected mass=3982.96).

Compounds 122-124, and 130-132 were synthesized using similar methods and reagents as described herein for compounds 125-129.

Example 5

Using the methods of the present invention described herein, a compound according to the present invention may be formed by covalently coupling one or more molecules of fatty acid to a substrate-binding peptide comprising a biofunctional composition. In this example, illustrated are compounds formed by covalently coupling fatty acid to a biofunctional composition comprising a substrate-binding peptide having binding specificity for a non-biological substrate, and a substrate-binding peptide having binding specificity for a biological substrate, with the two respective substrate binding peptides being covalently coupled to each other. Also illustrated is a compound comprised of fatty acid coupled to a biofunctional composition comprised of a first substrate-binding peptide having binding specificity for a non-biological substrate, and a second substrate-binding peptide having binding specificity for a non-biological substrate, with the two respective substrate-binding peptides being covalently coupled to each other. It is apparent to one skilled in the art, that additional embodiments of the 2 substrate-binding peptides of a biofuinctional composition can include, but is not limited to, each being substrate-binding peptide having binding specificity for a biological substrate.

Shown in Table 5 are illustrative compounds of the invention, synthesized by the methods described herein. The compounds are listed as a linear sequence, with same abbreviations used in Example 4, as well as "Ahx" representing fatty acid comprising aminohexanoic acid; and "NH2" means a modified C-terminal amino acid which has been amidated. A first and second representative substrate-binding peptide having binding specificity for a non-biological substrate (comprising metal), and further including a linker at the C-terminal end to be biotinylated to facilitate detection during functional studies, are represented by the amino acid sequence of SEQ ID NO:122 and HKKNNPKKKNKTRGSSK (SEQ ID NO:123) (a shortened version of SEQ ID NO:122). A third and fourth representative substrate-binding peptide having binding specificity for a non-biological substrate (comprising vancomycin and related analogs) are represented by the amino acid sequence of SSSCLIDMYGVCHNFD-GAYDSSRG (SEQ ID NO:124), SSCLIDIYGVCHNFDAY (SEQ ID NO:125) (shortened version of SEQ ID NO:124), and SSCLIDIYGKCHNPLR (SEQ ID NO:126) (shortened version of SEQ ID NO:124). A representative substrate-binding peptide having binding activity for a biological substrate (a known antimicrobial peptide binding to a bacterial surface component) is represented by the amino acid sequence of KWKLFKKIGAVLKVLK (SEQ ID NO:127).

TABLE 5

| Compound Ref. # | Compound linear sequence |
|---|---|
| 133 | MYR-Ahx-SEQ ID NO: 124-linker-SEQ ID NO: 122 |
| 134 | AUD-AUD-AUD-AUD-SEQ ID NO: 124-linker-SEQ ID NO: 122 |
| 135 | MYR-Ahx-SEQ ID NO: 125-linker-SEQ ID NO: 123 |
| 136 | $[MYR\text{-}Ahx]_2$-K-SEQ ID NO: 125-linker-SEQ ID NO: 123 |
| 137 | MYR-Ahx-SEQ ID NO: 127-linker-SEQ ID NO: 122 |
| 138 | SEQ ID NO: 126-AUD-AUD-AUD-AUD-AUD-AUD-SEQ ID NO: 122-NH2 |
| 139 | SEQ ID NO: 126-AUD-AUD-AUD-AUD-AUD-SEQ ID NO: 122-NH2 |

Standard Fmoc/t-Bu chemistry using AA/TBTU/HOBt/NMM (1:1:1:2) as the coupling reagents was employed to synthesize compound 133. The base resin, Fmoc-PAL-PEG-PS (~0.20 mmol/g) was used for synthesis of an amino acid sequence comprising SEQ ID NO:122, followed by two mini-PEG linkers, followed by an amino acid sequence comprising SEQ ID NO:124. Amino acids were used in 5 fold excess in the synthesis cycles and all residues were doubly or triply coupled. The coupling reactions were monitored by Kaiser ninhydrin test or chloranil test. In order to suppress peptide aggregation, pseudoproline dipeptides Fmoc-Ser-Ser(PsiMe, Me pro)-OH were employed, and were double coupled in 5 fold excess. Fmoc-Lys(Biotin)-OH and Fmoc-Mini-PEG-$CO_2H$ were double coupled manually using the above coupling conditions. Fmoc deprotection reactions were carried out using 20% piperidine in DMF with 0.1 M HOBt. Amino-hexanoic acid (Ahx) was introduced at the N-terminus of the resin-bound peptide followed by double coupling of myristic acid using TBTU activation method.

The compound was cleaved from the resin using Reagent K (TFA: EDT:$H_2O$:phenol:thioanisole=82.5:2.5:5:5:5) at room temperature for 4 hours. The crude products were precipitated in cold ether. The pellet obtained after centrifugation was washed thrice with cold ether, and lyophilized to give white solid as crude peptide. The crude linear peptides were cyclized using 3% DMSO in 10 mM PBS (pH 7.4) buffer for 48 hours (peptide concentration~0.065-0.075 mM) The crude cyclic peptide was purified on an RP-HPLC column (C18; 250×21.2 mm) using mobile eluants (A=$H_2O$/TFA (0.1% TFA) and B=Acetonitrile/TFA (0.1% TFA) using a gradient of 15% B to 55% B in 50 min at 10 mL/min @ 220 nm. The fractions containing the desired product were pooled and lyophilized to obtain a fluffy white powder (>95% purity) in 10% overall yield. Compound 133 was purified (HPLC retention time of 13.61 minutes (25 to 65% B in 30 min @ 1 mL/min at 220 nm), and characterized by MALDI-TOF (observed mass=6131; expected mass=6122.7).

Compounds 134-139 were synthesized using similar methods and reagents as described herein for compounds 133.

Example 6

In this example, illustrated are unexpected beneficial properties of the composition of the invention, including but not limited to, one or more improved biophysical properties. Such one or more unexpected beneficial properties of a composition of the invention may comprise an increase in stability. An increase in stability may comprise any one or more of resistance to chemical denaturation, resistance to proteolytic degradation, improved retention to a substrate (e.g., resistance to being competed off a substrate to which it is bound, such as by proteins or other biomolecules found in body tissues). Thus, to ascertain a beneficial property of a composition of the invention, it is compared to the properties of a component of the composition-namely, a substrate-binding peptide by itself (e.g., without fatty acid covalently coupled thereto). An assay was developed that, from our direct comparisons (see, e.g., discussion of FIG. 2 below, and Example 7 herein), mimicked the effect of incubation of substrate-binding peptide with human plasma on stability of binding of a substrate-binding peptide to its substrate. The assay utilized incubations in the presence of 10% bovine serum album (BSA) with 10 mM guanidinium chloride. The high BSA concentration mimics the elevated albumin content of human plasma, and the guanidinium chloride is used to compete with any charged interactions involved in binding of the substrate-binding peptide to its substrate.

In this assay, two immunoassay plates were prepared for a "side-by-side" comparison of binding of a test sample (substrate-binding peptide or composition of the invention) to its substrate with or without the presence of 10% BSA with 10 mM guanidinium chloride. The wells of each 96-well polypropylene plate were incubated with 350 µl BSA 1% in PBS for 30 minutes at 20° C. with 500 rpm shaking. To each well was added one acetone-cleaned 3/32" 316LVM stainless steel bead, followed by addition of dilutions in PBS of the test sample in a range of concentrations starting from 10 µM. Final volume in each well was 200 µl. The plates were incubated for 1 hour at 20° C. with 500 rpm shaking to allow for the binding to occur. The beads were washed 3 times with 250 µl PBS using a plate washer. At this point the method differed in further steps to complete depending on whether the assay was in the presence of 10% BSA with 10 mM guanidinium chloride or without the presence of 10% BSA with 10 mM guanidinium chloride.

In the immunoassay for detecting binding without the presence of 10% BSA with 10 mM guanidinium chloride, added to each well was 200 µl of streptavidin AP (AP is alkaline phosphatase) at 1/200 in TBS+1% BSA. The plate was then incubated at room temperature for 20 minutes with 500 rpm shaking. The wells were then washed 3 times with 250 µl of a buffer containing Tween® using a plate washer. The beads were transferred to a clean polypropylene plate, and the added to each well was 200 µl of pNPP (p-Nitrophenyl Phosphate) substrate. When color has developed, each well was read at OD405 nm in endpoint mode using a plate reader. In the comparator assay for detecting the effect of 10% BSA with 10 mM guanidinium chloride, to each well was added 350 µl of 10% BSA with 10 mM guanidinium chloride. The plate was then incubated for 18 hours at 37° C. with 250 rpm shaking. The wells were washed three times with 250 µl PBS using a plate washer. Added to each well was 200 µl of streptavidin AP at 1/200 dilution in buffer+1% BSA. The plate was then incubated at room temperature for 20 minutes with 500 rpm shaking. The wells were washed three times with 250 µl buffer containing Tween® using a plate washer. The beads were transferred to a clean polypropylene plate, and added to the wells was 200 µl of pNPP. When color has developed, the wells were read at OD405 nm in endpoint mode using a plate reader. From these two assays, a concentration of peptide or composition was chosen as a comparison point, and calculated was the percent of peptide or composition remaining bound to its substrate (in this case, a metal surface) after an 18 hour incubation in the 10% BSA+10 mM guanidinium chloride ("% retention", see FIGS. 1 & 2).

With respect to this example and as shown FIG. 1, some additional test samples were included in the comparison assay. Included was a substrate-binding peptide by itself (having the amino acid sequence of SEQ ID NO:122). Also, in the development of the invention, molecules which are know to self assemble (e.g., PEG, hydrophobic amino acids, and the amino acid sequence RADARADA (SEQ ID NO:128)) were each covalently coupled to substrate-binding peptide. For example, using the methods described herein and methods known in the art, Fmoc-NH-$(PEG)_{27}$-$CO_2H$ was covalently coupled to a peptide having the amino acid sequence of SEQ ID NO:122 (compound 119, FIG. 1), amino acid sequence YWAWAYAW (SEQ ID NO:129) was covalently coupled to a peptide having the amino acid sequence of SEQ ID NO:122 (compound 120, FIG. 1). As shown in FIG. 1, and as compared to the substrate-binding peptide alone (FIG. 1, "SEQ ID NO: 122") in this assay, surprisingly the aforementioned molecules that are known to promote self assembly failed to promote retention of binding of the substrate-binding peptide component to its substrate (see, e.g., compounds 119 & 120 in FIG. 1). Generally speaking, even using a compound having one or two molecules of fatty acid attached (e.g., less than 25 carbons in total) had little effect in promoting retention. However, unexpectedly, a composition of the invention comprising compound having more than 2 fatty acids covalently coupled to substrate-binding peptide significantly improved retention of binding of substrate-binding peptide component to its substrate (see, e.g., compositions 122, 123, 129-132 in FIG. 1), and in some cases approaching retention of 100% of the substrate binding peptide to its substrate. Significant retention of binding, as compared to the substrate-peptide control, is a measure of an improvement of or promotion in stability.

This is surprising and unexpected for the following reasons. First, as shown in FIG. 1 and discussed above, molecules which are known in the art to promote self-assembly failed to promote stability of a substrate-binding peptide. Secondly, not only must the molecules of fatty acid (which are covalently coupled to substrate-binding peptide) be able to associate with each other in forming the macromolecular network, but the fatty acid must also be able to self-associate without negatively affecting the binding of the substrate-binding peptide to its substrate. Additionally, the self-association in forming the macromolecular network formation must also present a conformation that promotes or increases stability of the substrate-binding peptide. Thus, these and other results show that in vitro and in vivo stability of a substrate-binding peptide can be unexpectedly improved or increased by covalently coupling two or more fatty acid molecules to the substrate-binding peptide in forming a compound which is then mixed with a carrier medium to form a composition of the invention comprising a macromolecular network.

Figure 2:
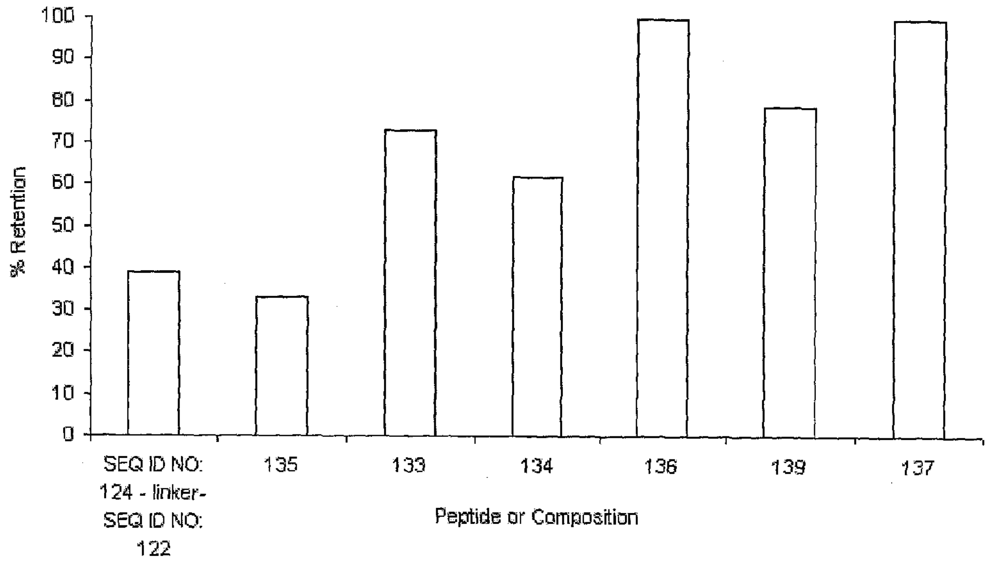
FIG. 2 is a bar graph measuring the retention of substrate-binding peptide by itself (e.g., SEQ ID NO:124-linker-SEQ ID NO:122) or compositions comprising molecular network of the invention (e.g., compositions 133, 134, 136, 137, 139; see Example 6 herein) to a substrate in assay conditions which mimic the presence of human plasma.

As shown in FIG. 2, and as compared to the substrate-binding peptide alone (biofunctional composition; FIG. 2, "SEQ ID NO:124-linker-SEQ ID NO:122"), generally speaking relative to a biofunctional composition as a substrate-binding peptide, a composition formed of compound having one or more molecules of fatty acid attached to substrate-binding peptide can increase or promote stability of the substrate-binding peptide component to its substrate (see, e.g., compositions 133, 134, 136,137 & 139 in FIG. 2), and in some cases approaching retention of 100% of the substrate binding peptide to its substrate. This is surprising and unexpected for the same and similar reasons discussed above in reference to FIG. 1. As shown in FIG. 2, it is noted that in this assay assessing stability, composition 133 promotes stability as measured by about 75% retention of the substrate-binding peptide to it substrate. Using a radiolabeled compound 133 and measuring exposure for periods ranging from 18 hours to 10 days in human plasma in assaying amount of compound 133 retained to a substrate for which the substrate-binding peptide component has binding specificity, demonstrated is stability comprising between about 80% to about 100% retention of compound 133 at the highest concentrations of compound 133 tested.

Example 7

This example further illustrates the ability of a composition according to the invention to promote stability of a substrate-binding peptide to a substrate. In this example, an in vitro model for in vivo stability on a medical device comprising a stent was performed. The stent flow model included a "circulatory system" comprising a peristaltic pump and clear silicone tubing into which is placed a stent (8 mm, stainless steel) coated with a composition according to the invention. Coating of the stents was accomplished by incubating the stents with radiolabelled composition 132 (specific activity 2,400 cpm/pmole at 20 μM in PBS) for 1 hour at 20° C., followed by extensive washing with buffer. In one variation of the stent flow model, human plasma was circulated through the circulatory system at a flow rate of 5 ml/min for 7 days at 37° C. In another variation of the stent flow model, 10% BSA+10 mM guanidinium chloride was circulated through the circulatory system at a flow rate of 5 ml/min for 18 hours at 37° C. After circulation in the respective variations of the stent flow model, the coated stents were then counted for radioactivity. To serve as an assay "control", some coated stents were not placed in the stent flow model, but rather counted for radioactive counts to provide a reference from which percent retention could be calculated for those coated stents included in the stent flow model. In both variations of the stent flow model (exposure to human plasma or 10% BSA+10 mM guanidinium chloride), over 90% of the composition remained bound to the coated stents.

Example 8

In this example, included is another illustration of a composition of the invention having improved beneficial properties (including, but not limited to, one or more improved biophysical properties), as compared to a substrate-binding peptide by itself. The unexpected benefit illustrated in this example relates to loading capacity for a biomolecule of which a substrate-binding peptide has binding specificity. As described in Example 5, an illustrative biofunctional composition ("SEQ ID NO:124-linker-SEQ ID NO:122") comprises a substrate-binding peptide having binding specificity for vancomycin ("SEQ ID NO:124") linked to a substrate-binding peptide having binding specificity for metal ("SEQ ID NO:122"). In this illustration, compared at equal concentrations was the ability of the biofunctional composition to bind vancomycin and the ability of composition 133 to bind vancomycin.

A substrate comprising a metal (as represented by stainless steel bead) was placed into wells of a 96 well plate. To each well was added a test sample comprising either the biofunctional composition alone, or composition 133 according to the invention, at concentrations ranging from about 0.1 μM to about 2 μM (in PBS, in a total volume of 150 μl). The plate was incubated for 30 minutes, and then the wells and beads were washed three times with buffer. Added to each well was 150 μl of a stock solution of BODIPY-FL vancomycin, a commercially available, green-fluorescent analog of vancomycin having antibiotic activity comparable to vancomycin. The plates were incubated for 30 minutes, and then the wells and beads were washed three times with buffer. By adding 200 μl of 10 mM HCl per well, any BODIPY-FL vancomycin specifically bound to the composition or the control is eluted from the metal bead. The fluorescent signal from BODIPY-FL vancomycin was then measured by detecting emission of light of wavelength 530 nm following excitation with light of wavelength 490 nm, and plotted against the concentrations of the test sample to generate a binding curve. At a concentration of 1 μM, the fluorescent intensity for the biofunctional composition by itself was quantified as about 12,000 counts per second (cps), whereas at the same concentration, the fluorescent intensity for composition 133 was quantified as about 22,000 cps. Thus, unexpectedly, a composition of the invention resulted in almost 2 fold increase in the loading capacity of a biomolecule (in this case, vancomycin) by the biofunctional composition, as compared to the biofunctional composition itself (not in the form of a composition of the invention).

Example 9

This example further illustrates the beneficial properties of a composition according to the invention to promote stability of a substrate-binding peptide to a substrate, as well as to increase loading of a biomolecule for which a substrate-binding peptide has binding specificity. In this assay, titanium pins were used as a model for tibia pins. Briefly, sterile pins were first coated with biofunctional composition ("SEQ ID NO:124-linker-SEQ ID NO:122") comprising a substrate-binding peptide having binding specificity for vancomycin ("SEQ ID NO:124") linked to a substrate-binding peptide having binding specificity for metal ("SEQ ID NO:122"), or a composition of the invention formed from compound comprising the biofunctional composition covalently coupled to fatty acid. The respective coatings also include vancomycin bound thereto. The coated pins were then placed in a silicone tube containing liquid bacterial growth medium and inoculated with bacteria. After incubation, the pins were removed, and then the liquid growth medium was serially diluted. The serial dilutions were inoculated onto bacterial culture plates, the plates were incubated, and counted on the plates were bacterial colonies.

In this assay, test samples (biofunctional composition (Table 6, "BC") or compositions 133, 134, 135, 136 139) each were used to coat a pin by incubating the test sample (in a range of from about 0.8 mM to about 1 mM) with 2.5 μl of a 10 mM vancomycin solution and PBS to a final volume of 250 μl in a microtube (3 pins per tube) for 60 minutes at room temperature with occasional agitation. In a piece of silicone tubing (1.5 mm inner diameter, 50 mm long), added is tryptic soy broth +0.2% glucose, the coated pin, and $10^3$ colony forming units (cfu) of *Staphylococcus aureus* strain MZ100 in either a 20 μl inoculum, 40 μl inoculum, or 60 μl inoculum. The tubing is clamped closed, and the tubing is incubated for 37° C. for 3 hours. After 3 hours, serial dilutions (1:10, 1:100, 1:1000) were made of the culture media from each tubing, and 10 μl of the undiluted culture medium and of each dilution were spotted onto the bacterial culture plate. The bacterial culture plate was incubated overnight at 37° C., and then the cfus were counted. The results, a composite of different assay runs, are shown in Table 6 ("—" means no cfus; "many" means too many cfus to count, as they converge into one spot; "NT" means not tested).

TABLE 6

| cfu undiluted | cfu 1:10 | cfu 1:100 | cfu 1:1000 | Test Sample | Volume (μl) |
|---|---|---|---|---|---|
| 12+ | 4 | — | — | BC | 20 |
| — | — | — | — | 134 | 20 |
| — | — | — | — | 135 | 20 |
| — | — | — | — | 133 | 20 |
| 2 | 1 | — | — | 136 | 20 |
| — | — | — | — | 139 | 20 |
| many | 16 | 7 | — | BC | 40 |
| many | 6 | 1 | — | 134 | 40 |
| 1 | 1 | — | — | 135 | 40 |
| many | 10 | — | — | 133 | 40 |
| many | 15 | — | — | 136 | 40 |
| 13 | — | — | — | 139 | 40 |
| many | 24 | 7 | — | BC | 60 |
| many | 17 | 5 | — | 134 | 60 |
| 60 | 1 | 1 | — | 135 | 60 |
| NT | NT | NT | NT | 133 | 60 |
| NT | NT | NT | NT | 136 | 60 |
| NT | NT | NT | NT | 139 | 60 |

From the tibia pin assay results shown in Table 6, compositions 135 and 139 clearly show improved beneficial properties over the biofunctional composition alone. The benefit illustrated by this example may be attributable to both (a) an increase in stability of the substrate-binding peptide, having binding specificity for metal, to its metal substrate; and (b) increased loading capacity of the substrate-binding peptide, having binding specificity for vancomycin, to vancomycin.

Example 10

In this example, illustrated is an embodiment relating to formation of a composition according to the invention. Basically, to form a composition of the invention, compound of the invention is mixed with a carrier medium. For example, compound of the invention may be reconstituted with a pharmaceutically-acceptable carrier, as known to those skilled in the art. Typically, a preferred carrier medium is an aqueous solution which is contacted and mixed with the compound of the invention to form a composition according to the invention.

Formation of a composition of the invention, and evidence of macromolecular network formation, may be monitored or quantified by any means known in the art. In this example, macromolecular formation was detected using a standard assay for determining critical micelle concentration ("CMC"). In this assay, a solution containing the composition of the invention (in a range of concentrations in pH 7 phosphate buffered saline ("PBS")) was mixed with a solution of methyl orange (0.04 mM in PBS), and the absorbance of the mixture was measured at 484 nm ($A_{484}$). CMC is the concentration at which a sharp decrease in absorbance at $A_{484}$ is observed, a change in the optical properties of methyl orange when trapped in a hydrophobic phase, such as caused by self-association as a macromolecular network (Table 7, "CMC"). Also included in this assay were an assay control peptide having an amino acid sequence of SEQ ID NO:122 (Table 7, "Control"), and compound 119 (a PEGylated peptide, the peptide having an amino acid sequence of SEQ ID NO:122, as described in more detail in Example 6 herein). As shown by the results illustrated in Table 7, only compounds of the invention demonstrated a CMC of less than 1 μM, an indicator of macromolecular network formation at such concentrations.

TABLE 7

| Compound Ref. # | CMC (μM) |
|---|---|
| Control | >>10 |
| 119 | >>10 |
| 122 | 0.123 |
| 123 | 0.04 |
| 125 | 0.123 |
| 126 | 0.37 |
| 127 | 0.123 |
| 128 | 0.123 |
| 129 | 0.123 |
| 130 | 0.041 |
| 131 | 0.37 |
| 132 | 0.123 |

Example 11

In this example, illustrated is a method of applying a composition of the invention to a substrate, the method comprising contacting the composition with the substrate under conditions suitable so that the composition binds to the substrate. In one example, wherein the substrate is a medical device, a composition of the invention is applied to the medical device as a coating before positioning the medical device in situ. In another example, a composition according to the invention is applied to a medical device in situ. For example, if the medical device is exposed through an open site in the body (e.g., such as in surgery), or is positioned at a site openly accessible outside the body (e.g., a dental implant accessible through an open mouth), a physician may spray or otherwise apply the composition to the medical device in situ. In another example wherein the medical device is not readily accessible by applications such as a spray coating, a composition according to the invention may be administered by injection at the site of the medical device such that the composition comes in contact with the medical device so as to bind to the medical device.

To facilitate formation of the composition and application of the composition (e.g., by spray, soaking, or injection) to a substrate, the composition comprises a pharmaceutically acceptable carrier. Conventional processes known in the art may be used to apply a composition according to the present invention to one or more surfaces of a substrate to be coated (in contacting the composition with the one or more surfaces in forming a coating thereon). Depending on the nature of the substrate to which the composition is to be applied, such processes are known to include, but are not limited to, soaking, mixing, dipping, brushing, spraying, and vapor deposition. For example, a solution or suspension comprising the composition may be applied through the spray nozzle of a spraying device, creating droplets that coat the surface of the substrate to be coated. The coated substrate is allowed to dry. If desired, the coated substrate may be further processed prior to use (e.g., washed in a solution (e.g., water or isotonic buffer) to remove excess composition not specifically bound to the substrate; if for in vivo use, by sterilizing using any one or methods known in the art for sterilization). Alternatively, the composition and the substrate may each be separately sterilized prior to the process of combining them, and then performed under sterile conditions is the applying of the composition to one or more surfaces of the substrate.

In another process for applying the composition to one or more surfaces of a substrate to be coated, a surface of the substrate to be coated is dipped into a liquid (e.g., solution or suspension, aqueous or solvent) containing the composition according to the invention in an amount effective to coat the surface of the substrate. For example, the surface is dipped or immersed into a bath containing the composition. Suitable conditions for applying the composition as a coating composition include allowing the surface to be coated to remain in contact with the carrier medium containing the composition for a suitable period of time (e.g., ranging from about 5 minutes to about 5 hours; more preferably, ranging from 5 minutes to 60 minutes), at a suitable temperature (e.g., ranging from 10° C. to about 50° C.; more preferably, ranging from room temperature to 37° C.). If desired, the coated substrate may be further processed, as necessary for use (e.g., one or more of drying, washing, sterilization, and the like). These illustrative processes for applying a composition to a substrate are not exclusive, as other coating and stabilization methods may be employed (as one of skill in the art will be able to select the compositions and methods used to fit the needs of the particular surface material of which a substrate is comprised, substrate, or purpose).

Additionally, in a method according to the present invention, a coat on a substrate surface comprising the composition may be stabilized, for example, by air drying. However, these treatments are not exclusive, and other coating and stabilization methods may be employed. Suitable coating and stabilization methods are known in the art. For example, the at least one surface of the substrate to be coated with the composition of the present invention may be pre-treated prior to the coating step so as to enhance one or more of the binding of the composition to the surface, and the consistency and uniformity of the coating.

Example 12

Chemistry for Coupling Interaction Tags to Substrate Binding Domains

One or more hydrophobic interaction tags comprising fatty acid residues can be covalently coupled to the substrate binding peptides of the presently disclosed subject matter according to the procedures described herein above, for example, at Example 5. The hydrophobic interaction tags can be coupled at one or both the N-terminus or C-terminus. Similarly, one or more charged interaction tags comprising amino acid residues can be covalently coupled at one or both the N-terminus or C-terminus of the substrate binding peptides of the presently disclosed subject matter.

Briefly, a method for coupling either a hydrophobic interaction tag or a charged interaction tag is as follows. For example, a single aminoundecanoic acid (AUD) or a polymer of 2-10 AUDs (poly-aminoundecanoic acid ("polyAUD)") or a single amino acid or a poly-amino acid of the appropriate length is first assembled separately as a building block using standard solid phase methods. The appropriately protected fatty acid hydrophobic tags (e.g., Fmoc-polyAUD, Fmoc-Myristic acid, etc.) and the appropriately protected charged amino acid interaction tags (e.g., Fmoc-polyLys(Boc)-OH, Fmoc-polyArg(Mtr)-OH, Fmoc-polyAsp(OtBu)-OH, Fmoc-polyGlu(OtBu)-OH, etc.) are coupled sequentially using the standard Fmoc/t-Bu chemistry using AA/HBTU/HOBt/NMM (1:1:1:2) as the coupling reagents (AA is amino acid; HOBt is O-Pfp ester/1-hydroxybenzotriazole; HBTU is N-[1H-benzotriazol-1-yl)(dimethylamino) methylene]-N-methylmethanaminium hexafluorophosphate N-oxide; NMM is N-methylmorpholine). The amino acids and fatty acids are used in 5-10 fold excess in the synthesis cycles, and all residues are doubly, triply or even quadruply coupled depending upon the complexity of residues coupled. The coupling reactions are monitored by Kaiser ninhydrin test. The Fmoc deprotection reactions are carried out using 20% piperidine in dimethyl-formamide. Peptide cleavage from the resin is accomplished using Reagent K (TFA (trifluoroacetic acid): EDT (1,2-ethanedithiol):$H_2O$:phenol:thioanisole=82.5:2.5:5:5:5) at room temperature for 4 hours. The crude product is precipitated in cold ether. The pellet obtained after centrifugation is washed with cold ether and lyophilized to give a white solid as crude desired product. The crude products are analyzed by analytical high performance liquid chromatography (HPLC) on a C-18 column using mobile eluants (A=$H_2O$/TFA (0.1% TFA) and B=Acetonitrile/TFA (0.1% TFA). The peptides are also further analyzed by mass spectrometry before subjecting each to final purification by preparative HPLC. The fractions containing the desired product are pooled and lyophilized to obtain a fluffy white powder.

One or more hydrophobic interaction tags comprising fatty acid residues can be covalently coupled to the substrate binding polymers of the presently disclosed subject matter. For example, a single aminoundecanoic acid (AUD) or a polymer of 2-10 AUDs (poly-aminoundecanoic acid; ("polyAUD)") of the appropriate length is first assembled separately as a building block using standard solid phase methods. The polyAUD is deprotected and purified by HPLC. The free acid is activated using carbodiimide chemistry. The polyethylenimine (PEI) polymer is dissolved in appropriate buffer having pH between 7 and 9 (0.1 M sodium phosphate, pH 7.5).

Amine containing buffers like TRIS are avoided. The activated polyAUD acid is dissolved in an acetonitrile-buffer mix and added to the PEI solution in at least 5-10 molar excess with stirring. The reaction is allowed to proceed for a few hours at room temperature until completion. The PEI polymer-AUD conjugate is purified by gel filtration of dialysis.

Example 13

Substrate Binding Peptides Having Binding Affinity for Target Molecule Vancomycin This Example describes the generation of substrate binding peptides having binding affinity a target molecule vancomycin according to the methods for utilizing phage display technology outlined previously in Example 1. More specifically, the following subject matter for discovering substrate binding peptides having binding affinity for the target molecule, vancomycin, and generation of the vancomycin binding peptides is taken from PCT International Patent Application Publication No. WO/2009/055313, which is herein incorporated by reference in its entirety.

As an illustrative example of methods used in development of this presently disclosed subject matter, an aliquot of biotinylated vancomycin (100 pmoles) in buffer-T (200 µl, 0.05 M Tris-buffered saline, with TWEEN-20 at a final concentration of 0.05%) was dispensed in a series of microfuge tubes. Added per tube was 25 µl of a mixture of phage libraries to be screened (e.g., at a concentration of $10^{10}$ pfu/ml each), and the mixture was incubated at room temperature for 2 hours. To the mixture was added streptavidin-labeled metal beads which had been blocked with 1% bovine serum albumin (BSA) in buffer-T, and the bead-containing mixture was gently mixed for 2 hours at room temperature. The tubes were then washed 3 times with 1 ml of buffer-T+0.5 mM biotin, using magnetism to pull down the metal beads each time. The supernatant was removed, and phage was eluted from the metal beads by competition with vancomycin. In the elution process, added to each tube containing the beads was 20 µl of 0.1 mM vancomycin, and the bead-containing mixture was incubated at room temperature for 20 minutes. The phage-containing supernatant was then transferred to cultures of *E. coli* cells susceptible to phage infection, and incubated overnight at 37° C. in a shaker incubator. Phage supernatant was harvested by centrifugation of culture medium at 8500×g for 10 minutes. Second and third rounds of selection were performed in a similar manner to the first round, using the amplified phage from the previous round as input.

For determining phage binding, an ELISA (enzyme-linked immunoassay) was performed as follows. Wells of a microtiter plate were coated with streptavidin by incubating 50 µl of a 10 µg/ml solution per well for 16 hours and at 4° C. Non-specific binding sites on the well surfaces of the microtiter plate were blocked with 250 µl 1% BSA in 0.1 M $NaHCO_3$. The plate was incubated for at least 2 hours at room temperature. After washing the wells 3 times with buffer-T, to each well was added biotinylated vancomycin (0.1 µM) in 100 µl buffer-T and incubated for 30 minutes at room temperature. Biotin (0.1 µM) in 100 µl buffer-T was then added to each well, to block any available streptavidin sites. The plate was incubated for 30 minutes at room temperature, followed by 5 washes with buffer-T. To each well was added 175 µl of buffer-T and 25 µl of the phage solution being tested, followed by incubation at room temperature for 2 hours. Following several washes with buffer-T, added was anti-M13 phage antibody conjugated to horseradish-peroxidase, followed by incubation, and washing. Added was chromogenic agent ABTS (2,2'-azino-bis(3-ethylbenzthiazoline-6-sulphonic acid), and determined was a read-out at 405 nm at 15 minutes. The resultant absorbance value for each well correlates to the amount of phage bound to vancomycin.

Primers against the phage vector sequence that flank the insertion site were used to determine the DNA sequence encoding the peptide for the phage in each group. The sequence encoding the peptide insert was translated to yield the corresponding amino acid sequence displayed on the phage surface. The amino acid sequences, encoding peptides isolated using vancomycin as the representative glycopeptide antibiotic, were determined and are shown in Table 8. While phage amino acids adjoining the peptides typically did not provide a significant contribution to the binding affinity of the peptide, the peptides according to the presently disclosed subject matter can comprise, in their amino acid sequence, phage amino acids adjoining the peptide at the N-terminus (SS) and at the C-terminus (SR). The peptide sequence shown in SLIDMYGVCHNFDGAYDS (SEQ ID NO: 130) represents site directed mutagenesis of the first cysteine residue of CLIDMYGVCHNFDGAYDS (SEQ ID NO: 131) to a serine residue.

The phage-derived sequences were further evaluated as synthetic peptides. Peptides according to the presently disclosed subject matter can be synthesized using any method known to those skilled in the art including, but not limited to, solid phase synthesis, solution phase synthesis, linear synthesis, recombinantly, and a combination thereof. In this example, peptides were synthesized using standard solid-phase peptide synthesis techniques on a peptide synthesizer using standard Fmoc chemistry. After all residues were coupled, simultaneous cleavage and side chain deprotection was achieved by treatment with a trifluoroacetic acid (TFA) cocktail. Crude peptide was precipitated with cold diethyl ether and purified by high performance liquid chromatography (HPLC) using a linear gradient of water/acetonitrile containing 0.1% TFA. Homogeneity of the synthetic peptides was evaluated by analytical reverse phase-HPLC, and the identity of the peptides was confirmed with mass spectrometry.

A typical binding assay for glycopeptide antibiotic was performed according to the following procedure. Briefly, synthetic peptides comprising an amino acid sequence to be characterized for binding were biotinylated to facilitate immobilization on streptavidin-coated 96-well plates. The microtiter plates were coated with streptavidin by adding 50 µl of a 10 µg/ml streptavidin solution in 0.1 M $NaHCO_3$, and incubating the plates for at least 3 hours. The plate wells were blocked by adding 150 µl of a 1% BSA solution in 0.1 $NaHCO_3$ with incubation for at least 2 hours, and the plates were stored at 4° C. until needed. Before use, the streptavidin plates were washed extensively in buffer-T. Added per well was peptide (100 µl 0.1 µM peptide in buffer-T), and then incubated for 30 minutes at room temperature with shaking. 200 µl of 0.5 mM biotin in buffer-T was added to block the remaining streptavidin sites, and plates were incubated for 15 minutes at room temperature. Plates were then washed with buffer-T to remove the excess biotin and peptide. Serial dilutions of biotinylated glycopeptide antibiotic in buffer-T were added (100 µl) to each well, representing a range of concentrations between 100 pM and 100 µM. Plates were incubated for 30 minutes at room temperature with shaking prior to washing several times with buffer-T. Glycopeptide antibiotic was then detected by adding 100 µl of a diluted streptavidin-alkaline phosphatase conjugate to each well and incubated at room temperature for 30 minutes. Excess conjugate was removed by repeated washes with buffer-T, and the amount of alkaline phosphatase remaining in the well was detected using a pNPP (para-nitrophenylphosphate) colorimetric enzymatic assay. The relative amount of glycopeptide antibiotic captured by the peptides was determined by measuring the absorbance at 405 nm of the colored product of the alkaline phosphatase reaction. The EC50 was determined for each peptide relative to the binding affinity for the glycopeptide antibiotic used in the assay, as shown in Table 8 (with vancomycin as a representative glycopeptide antibiotic).

TABLE 8

| Peptide sequences isolated by phage selections using vancomycin | | |
|---|---|---|
| SEQ ID NO: | Amino acid sequence | EC50 (μM) for vancomycin binding |
| 131 | **C**LIDMYGV**C**HNFDGAYDS | 0.10 |
| 132 | **C**LFDIFGV**C**HSFDGAYDS | 0.06 |
| 133 | P**C**ELIDMFGNDH**C**P | 0.82 |
| 134 | S**C**DMLF**C**ENFSGSGNNWFS | 10 |
| 130 | **S**LIDMYGV**C**HNFDGAYDS | 10 |

To identify additional peptides capable of binding vancomycin, a scanning degenerate codon mutagenesis study was performed using (SEQ ID NO: 131). To rapidly test variants of the isolated vancomycin binding peptide, a bacterial expression system was designed. Under this system, a peptide sequence was placed under the transcriptional control of a T7 promoter. The peptide was expressed with an N-terminal OmpA signal peptide, targeting it for secretion. An HA-tag was engineered downstream of the peptide sequence for antibody-mediated detection, a rhinovirus protease cleavage site was engineered for peptide liberation, and the DNA sequence encoding alkaline phosphatase was engineered for p-NPP colorimetric detection. Using this expression system, a scanning mutagenesis study was performed in which new peptide sequences were generated using mutagenic oligonucleotide primers and tested for vancomycin binding. The C-terminal His6 tag enabled the high-throughput peptide purification on $Ni^{2+}$ columns or beads (Qiagen; Cat#30600). After PCR mutagenesis and cloning of a sequence into the vector, competent cells were transformed and cultured overnight on 2×YT-KAN-BCIP(40 ug/ml) plates at 37° C. Transformed colonies were grown in 2×YT-KAN broth overnight. Peptide-AP fusion-containing supernatants were harvested and tested for binding to vancomycin. Briefly, the variant peptides were tested for vancomycin binding as follows. A streptavidin coated microtiter plate was coated with biotinylated vancomycin. The concentrations of the alkaline-phosphatase linked variant peptides were normalized to equal levels based on the alkaline-phosphatase activity as determined in a kinetic assay with the alkaline-phosphatase specific chromogenic substrate p-nitrophenyl phosphate (p-NPP). A streptavidin coated microtiter plate was coated with biotinylated vancomycin. Normalized amounts of alkaline-phosphatase linked peptides were allowed to bind to the immobilized vancomycin and detected by addition of the alkaline-phosphatase specific chromogenic substrate p-NPP. The results of the mutagenesis study are shown in Table 9.

TABLE 9

| Scanning degenerate codon mutagenesis (SEQ ID NO: 131) Substitution | | | |
|---|---|---|---|
| Position | Acceptable | Unacceptable | Reduced Binding |
| C1 | C | A E G P S V | |
| L2 | L M | C G P Q T | D K S W |
| I3 | I M | A G P S | L |
| D4 | D | E H S Y A | |
| M5 | M I | F H K R W V | |
| Y6 | Y | A D E G K N S V | |
| G7 | G | A R S V | L E |
| V8 | V R K Q | C P | G S W D |
| C9 | C | D E G W | R |
| H10 | H | A E G K L M N P R T | |
| N11 | N D M S | C | G E |
| F12 | F E H K L P Q R S Y | | |
| D13 | D L T V | C | A Y |
| G14 | G R | | S A F K T V W Y |
| A15 | A G | C | P S |
| Y16 | Y M W G | | C L Y |
| D17 | D I L P | | |

From an alignment of the amino acid sequence of the peptides identified by phage selections using vancomycin as the illustrative glycopeptide antibiotic in Table 8, a consensus glycopeptide antibiotic binding domain sequence was constructed representing all of SEQ ID NOs: 131-134 and taking into account the results of the mutagenesis study with SEQ ID NO: 131. The consensus glycopeptide antibiotic binding domain SEQ ID NO: 135 is as follows: $CXaa_{0-3}$DMFG$Xaa_{0-3}$C, (SEQ ID NO: 135), wherein Xaa represents any amino acid, the 2 cysteine residues are disulfide bonded, and the length between the 2 cysteine residues can range from 4 to 10 amino acids.

Similarly, from an alignment of the amino acid sequence of the peptides identified by phage selections using vancomycin as the illustrative glycopeptide antibiotic in Table 8, a consensus glycopeptide antibiotic binding domain sequence was constructed representing all of SEQ ID NOs: 131-134 and taking into account the results of the mutagenesis study with SEQ ID NO: 131. The consensus glycopeptide antibiotic binding domain SEQ ID NO: 136 is as follows: $Xaa_1Xaa_2X_1X_2X_3$ $X_4X_5X_6X_7Xaa_3X_8X_9$, (SEQ ID NO: 136), wherein the sequence comprises at least 2 cysteine residues; wherein Xaa is any amino acid unless stated otherwise; wherein either $Xaa_1$ or $Xaa_2$ is C and $Xaa_2$ can be absent if $Xaa_1$ is C; wherein $X_1$ is L, M, I, V or A; wherein $X_2$ is I, M or F; wherein $X_3$ is D; wherein $X_4$ is M or I; wherein $X_5$ is F or Y; wherein $X_6$ is G; wherein $X_7$ is any amino acid except C or P; wherein if $X_8$ or $X_9$ is C, $Xaa_3$ is any amino acid except C and can be absent; wherein $X_8$ is C or H unless $Xaa_3$ or $X_9$ is C and then $X_8$ is not C; and wherein $X_9$ is H or C unless $Xaa_3$ or $X_8$ is C and then $X_9$ is not C.

In another embodiment, a consensus glycopeptide antibiotic binding domain sequence was constructed (SEQ ID NO: 137) representing all of SEQ ID NOs: 130-134 and taking into account the results of the mutagenesis study with SEQ ID NO: 131 shown in Table 9. The consensus glycopeptide antibiotic binding domain is as follows: $Xaa_1Xaa_2X_1X_2X_3X_4X_5X_6X_7Xaa_3X_8X_9$, (SEQ ID NO: 137) wherein the sequence comprises at least 2 cysteine residues; wherein Xaa is any amino acid unless stated otherwise; wherein either $Xaa_1$ or $Xaa_2$ is C and $Xaa_2$ can be absent if $Xaa_1$ is C; wherein $X_1$ is not C, G, P, Q or T; wherein $X_2$ is not A, G, P or S; wherein $X_3$ is D or C; wherein $X_4$ is M or I; wherein $X_5$ is F or Y; wherein $X_6$ is not A, R, S or V; wherein $X_7$ is any amino acid except C or P; wherein if $X_8$ or $X_9$ is C, $Xaa_3$ is any amino acid except C and can be absent; wherein $X_8$ is C or H unless $Xaa_3$ or $X_9$ is C and then $X_8$ is not C; and wherein $X_9$ is H or C unless $Xaa_3$ or $X_8$ is C and then $X_9$ is not C.

Thus, a peptide binding domain sequence motif is provided having binding affinity for glycopeptide antibiotic. A peptide according to the glycopeptide antibiotic binding domain of SEQ ID NOs: 135-137 can further comprise modifications according to the presently disclosed subject matter including, for example, one or more of a terminal modification, and a modification to facilitate linking of the peptide. Thus, such a peptide can have an amino acid sequence selected from the group consisting of SEQ ID NOs: 131-137. Preferably, the peptide according to the presently disclosed subject matter has a binding affinity for glycopeptide antibiotic of EC50 less than 1 μM.

Example 14

Substrate Binding Peptides Having Binding Affinity for a Metal Medical Device This Example describes substrate binding peptides having binding affinity for a metal substrate medical device discovered according to the methods for utilizing phage display technology outlined herein previously in Example 1. More specifically, the following subject matter describing substrate-binding peptides having binding affinity for a substrate that is a medical device is taken from PCT International Patent Application Publication No. WO2007/081942, which is herein incorporated by reference in its entirety.

Illustrative substrate binding peptides having binding affinity for a metal substrate medical device according to the presently disclosed subject matter were described in Patent Application Publication No. WO2007/081942 and conform to the following sequence motif: $X_1$—H—X—X—$X_2$—$X_2$—$X_2$—K—$X_1$—$X_1$—X—K—$X_1$—$X_1$—N—K (SEQ ID NO:138); where X is any amino acid; $X_1$ is K, N, or S, but preferably either K or N; and $X_2$ is K, N, or H. The illustrative peptides are further covalently coupled to one or both a hydrophobic interaction tag and a charged interaction tag according to the methods detailed herein at Example 12.

Similarly, a shortened version of the peptide sequence motif for metal binding shown above (SEQ ID NO:138) is described herein above at Example 5 and comprises a 4 amino acid linker sequence at the C-terminal end: HKKNNPKKKNKTRGSSK (SEQ ID NO:123). SEQ ID NO:123 is also disclosed herein at Example 5 comprising the covalently coupled hydrophobic tags of the presently disclosed subject matter. Peptides useful for binding metal substrates according to the presently disclosed methods conform to the following consensus sequence: $X_1$—$X_1$—K—$X_2$—$X_2$—X—K—$X_2$—$X_2$—N—K (SEQ ID NO:139), where X is any amino acid; $X_1$ is K, N, or H, and $X_2$ is K, N, or S, but preferably either K or N. Peptides conforming to the above sequence motifs can also be covalently coupled to one or both a hydrophobic interaction tag and a charged interaction tag according to the methods detailed in herein at Example 12.

Example 15

Substrate Binding Peptides Having Binding Affinity for a Target Molecule Cell This Example describes substrate binding peptides having binding affinity for a substrate target molecule that is a cell discovered according to the methods for utilizing phage display technology outlined herein previously in Example 1. More specifically, the following subject matter describing substrate-binding peptides having binding affinity for a target molecule that is a cell is taken from PCT International Patent Application Publication No. WO/2007/081943, which is herein incorporated by reference in its entirety.

Illustrative substrate binding peptides according to the presently disclosed subject matter having binding affinity for a target molecule that is a cell were described in Patent Application Publication No. WO2007/081943 and conform to the following sequence motif: C—$X_1$—X—X—X—$X_2$—X—$X_3$—P—X—X—X—$X_2$—X—P—$X_4$—$X_1$—C (SEQ ID NO:140); where X is any amino acid; $X_1$ is Asn or Gln; $X_2$ is Leu or lie; $X_3$ is a positively charged amino acid comprising Lys, Arg, or His; and $X_4$ is a negatively charged amino acid comprising Glu or Asp. The illustrative peptides are further covalently coupled to one or both a hydrophobic interaction tag and a charged interaction tag according to the methods detailed herein at Example 12.

Example 16

Substrate Binding Peptides Having Binding Affinity for Target Molecule Bone Morphogenic Proteins This Example describes substrate binding peptides having binding affinity for bone morphogenic proteins (BMPs) discovered according to the methods for utilizing phage display technology outlined herein previously in Example 1. More specifically, the following subject matter describing substrate-binding peptides having binding affinity for a BMP target molecule is taken from PCT International Patent Application Publication No. WO2006/098744A2, which is herein incorporated by reference in its entirety.

Illustrative substrate binding peptides having binding affinity for a BMP target molecule according to the presently disclosed subject matter were described in Patent Application Publication No. WO2006/098744A2 and matter fall into 2 different "sequence clusters". Each sequence cluster contains a common sequence motif. For the first sequence cluster of BMP-binding peptides, the common motif is designated as "Motif 1" and is as follows: Aromatic-X—X-Phe-X-"Small"-Leu (Aromatic=Trp, Phe, or Tyr; X=any amino acid; "Small"=Ser, Thr, Ala, or Gly; (SEQ ID NO:141). The second sequence cluster motif "Motif 2" comprises the sequence (Leu or Val)-X-Phe-Pro-Leu-(Lys or Arg)-Gly (SEQ ID NOs: 142). The illustrative substrate binding peptides were shown to bind BMP-2 with an affinity ranging from about 10-100 nM. The illustrative peptides are further covalently coupled to one or both a hydrophobic interaction tag and a charged interaction tag according to the methods detailed herein at Example 12.

Example 17

First and Second Substrate Binding Peptides Localizing Growth Factors to a Suture Medical Device This Example describes substrate binding peptides having binding affinity for growth factors discovered according to the methods for utilizing phage display technology outlined herein previously in Example 1. More specifically, the following subject matter describing substrate-binding peptides having binding affinity for a growth factor target molecule is taken from PCT International Patent Application Publication No. WO2009/032943, which is herein incorporated by reference in its entirety.

Illustrative substrate binding peptides having binding affinity for a GDF growth factor target molecule according to the presently disclosed subject matter were described in Patent Application Publication No. WO2009/032943 and are shown in Table 10. The compounds are listed as a linear sequence, with "AUD" representing aminoundecanoic acid, "MYR" representing myristic acid; "Ahx" represents a fatty acid comprising aminohexanoic acid; "B" represents biotin; and "NH2" means a modified C-terminal amino acid that has been amidated. The illustrative peptides in Table x comprising a hydrophobic interaction tag can be further covalently coupled to one or both an additional hydrophobic interaction tag and a charged interaction tag according to the methods detailed in herein at Example 12. Those peptides in Table 10 that do not comprise an interaction tag can also be covalently coupled to one or both a hydrophobic interaction tag and a charged interaction tag according to the methods detailed in herein at Example 12.

TABLE 10

| SEQ ID NO: | Peptide linear sequence |
|---|---|
| 143 | ssGGVGGWALFETLRGKEVsr-(AUD)$_6$-YFRAFRKFVKPFKRAFK-GSSGK-B-NH2 |
| 144 | YFRAFRKFVKPFKRAFK-(AUD)$_6$-ssGGVGGWALFETLRGKEVsr-GSSGK-B-NH2 |
| 145 | (AUD)$_4$-ssGGVGGWALFETLRGKEVsr-(MP)$_2$-YFRAFRKFVKPFKRAFK-GSSGK-B-NH2 |
| 146 | MYR-Ahx-ssGGVGGWALFETLRGKEVsr-(MP)$_2$-YFRAFRKFVKPFKRAFK-GSSGK-B-NH2 |
| 147 | YFRAFRKFVKPFKRAFK-(MP)$_2$-ssGGVGGWALFETLRGKEVsr-GSSGK-B-NH2 |
| 148 | ssGGVGGWALFETLRGKEVsr-(MP)$_2$-YFRAFRKFVKPFKRAFK-GSSGK-B-NH2 |
| 149 | ssGGVGGWALFETLRGKEVsr-P10-YFRAFRKFVKPFKRAFK-GSSGK-B-NH2 |
| 150 | SWWGFWNGSAAPVWSR-GSSG-ssGGVGGWALFETLRGKEVsr-GSSGK-B-NH2 |
| 151 | ssGGVGGWALFETLRGKEVsr-GSSG-SWWGFWNGSAAPVWSR-GSSGK-B-NH2 |
| 152 | ssGGVGGWALFETLRGKEVsr-(MP)$_2$-SWWGFWNGSAAPVWSR-GSSGK-B-NH2 |
| 153 | ssGGVGGWALFETLRGKEVsr-P10-SWWGFWNGSAAPVWSR-GSSGK-B-NH2 |
| 154 | ssGGVGGWALFETLRGKEVsr-(AUD)$_6$-SWWGFWNGSAAPVWSR-GSSGK-B-NH2 |
| 155 | ssGGVGGWALFETLRGKEVsr-GSSG-YFRAFRKFVKPFKRAFK-GSSGK-B-NH2 |

The following procedure was performed to test the ability of the exemplary peptides having binding affinity for a suture medical device coupled to a peptide having binding affinity for fibrous connective tissue-inducing growth factor to capture GDF-7 on the sutures. The peptide compositions described in Table 10 were tested as follows. ETHIBOND EXCEL 1 sutures (ETHICON) were cut into 0.5 cm length pieces with razor blade and placed in the wells of a 96-well polypropylene plate. The plate was blocked with 1% BSA/TBS (high salt) for 1 hr at RT by shaking. One μM peptide solutions were prepared in TBST high salt and the peptide solution was added at 100 μl/well/suture. Plates were incubated 30 min at RT shaking. The plates were washed manually with 4×250 μl of TBST high salt. GDF-7 (R&D SYSTEMS) solutions were prepared at a concentration of 50 nM in TBST high salt and added at serial 1:4 dilutions to the sutures in the 96-well plate at a concentration range of 0.01 nM-50 nM. The plate was incubated 1 hr at RT shaking. The plate was washed manually with 4×250 μl of TBST high salt. Detection of GDF-7 was performed using an anti-GDF-7 antibody-secondary antibody-AP conjugate with detection using a pNPP calorimetric enzymatic assay. A relative EC50 value for GDF-7 capture by the peptide compositions was determined and range from 1-20 nM for peptides SEQ ID NOs:143-146 having a covalently coupled hydrophobic tag and the remaining peptides (SEQ ID NOs:147-155) having a relative EC50 value of greater than 20 nm to greater than 100 nM.

Example 18

First and Second Substrate Binding Peptides Localizing Vancomycin to a Metal Medical Device In this example, methods are illustrated for coating a metal substrate with a composition of the presently disclosed subject matter wherein the target molecule being localized to the metal substrate is the antibiotic, vancomycin. In one embodiment, the compositions used in this experiment comprise a first substrate-binding peptide having binding affinity for a metal bead representing the medical device or a first substrate-binding polymer having a positive charge having binding affinity for a metal bead representing the medical device, a second substrate-binding peptide having binding affinity for the target molecule vancomycin, wherein the first and second substrate-binding peptide/polymer are not covalently linked, and the target molecule vancomycin. The molecules are combined and coated onto the metal bead as described herein below and the first and second substrate binding peptides are shown in Table 11 below. The first substrate binding polymer having a positive charge is polyethyleneimine of various molecular weights and is also shown in Table 11. The combinations of the first and second substrate binding peptides/polymers used in the experiment and the amount of vancomycin loaded onto the metal bead is shown in Table 12. Each of the metal substrate-binding peptides is covalently coupled to at least one interaction tag selected from the group consisting of a hydrophobic interaction tag, a positively charged interaction tag, and a negatively charged interaction tag. The hydrophobic interaction tags interact with each other and the charged interaction tags interact with oppositely charged interaction tags and/or the positively charged polymer. In this manner a macromolecular network is formed comprising a plurality of non-covalently coupled first and second substrate-binding peptides/polymers to load the vancomycin onto the metal bead.

In another embodiment, the compositions used in this experiment comprise a first substrate-binding peptide having binding affinity for a metal bead representing the medical device covalently linked to a second substrate-binding peptide having binding affinity for the target molecule vancomycin, and the target molecule vancomycin. The molecules are combined and coated onto the metal bead as described herein below. The first and second covalently linked substrate binding peptides are shown in Table 11 below. The first and second substrate binding peptides used in the experiment and the resulting amount of vancomycin loaded onto the metal bead is shown in Table 12. Each of the covalently linked first and second substrate-binding peptides is covalently coupled to at least one interaction tag selected from the group consisting of a hydrophobic interaction tag, a positively charged interaction tag, and a negatively charged interaction tag. The hydrophobic interaction tags interact with each other and the charged interaction tags interact with oppositely charged interaction tags. In this manner a macromolecular network is formed comprising a plurality of non-covalently coupled substrate-binding peptides to load the vancomycin onto the metal bead.

In another embodiment, the compositions used in this experiment comprise a first substrate-binding peptide having binding affinity for a metal bead representing the medical device covalently linked to a second substrate-binding peptide having binding affinity for the target molecule vancomycin, another second substrate-binding peptide, and the target molecule vancomycin. The molecules are combined and coated onto the metal bead as described herein below. The first and second covalently linked substrate binding peptides and the second substrate binding peptides are shown in Table 11 below. The combinations of the covalently linked first and second substrate binding peptides with the second substrate binding peptide used in the experiment and the resulting amount of vancomycin loaded onto the metal bead is shown in Table 12 below. Each of the covalently linked first and second substrate-binding peptides and the second substrate binding peptides are covalently coupled to at least one interaction tag selected from the group consisting of a hydrophobic interaction tag, a positively charged interaction tag, and a negatively charged interaction tag. The hydrophobic interaction tags interact with each other and the charged interaction tags interact with oppositely charged interaction tags. In this manner a macromolecular network is formed comprising a plurality of non-covalently coupled substrate-binding peptides to load the vancomycin onto the metal bead.

TABLE 11

| SEQ ID NO: | Sequence |
|---|---|
| 156 | RRRRRRR-PSSHRTNHKKNNPKKKNKTRGP-RRRRRRR-K(biotin) |
| 157 | RRRRRRR-PSSHRTNHKKNNPKKKNKTRGP-(AUD)6-K(Biotin) |
| 158 | (Aud)6-PSSHRTNHKKNNPKKKNKTRGP-RRRRRRR-K(biotin) |
| 159 | (AUD)6-SSHRTNHKKNNPKKKNKTRGSSG-RRRRRRR-K(biotin) |
| 160 | RRRRRRR-miniPeg-SSCLIDIYGVCHNFDAY-miniPeg-miniPeg-HKKNNPKKKNKTRGSS-K(Biotin) |
| 161 | RRRRRRR-miniPeg-SSCLIDIYGVCHNFDAY-(AUD)5-HKKNNPKKKNKTRGSS-K(Biotin) |
| 162 | SSCLIDIYGVCHNFDAY-miniPeg-miniPeg-HKKNNPKKKN KTRG-miniPeg-RRRRRRR-K(Biotin) |
| 163 | SSSCLIDMYGVCHNFDGAYDSSRG-miniPeg-miniPeg-SSHRTNHKKNNPKKKNKTRGSSGK |
| 164 | MA-Ahx-SSCLIDIYGVCHN FDAY-miniPeg-miniPeg-HKKNNPKKKNKTRGSSK(Biotin) |
| 165 | MA-AHx-SSCLIDIYGVCHN FDAY-miniPeg-miniPeg-YFRAFRKFVKPFKRAFKGSSK(Biotin) |
| 166 | Pyrene-butyric-SSCLIDIYGVCHNFDAY-miniPeg-miniPeg-HKKNNPKKKNKTRGSS-K(Biotin) |
| 167 | SSCLIDIYGVCHNFDAY-MiniPeg-DDDDDD |
| 168 | EEEEEE-MP-SSCLIDIYGVCHNFDAY-amide |
| 169 | EEEEEE-miniPeg-SSCLIDIYGVCHNFDAY-miniPeg-EEE EEE |
| 170 | DDDDDD-MP-K-dA-dA-acid |
| 171 | EEEEEEE-PSSCLIDIYGVCHNFDGAYDSSRGP-EEEEEEE |
| 172 | SSCLIDIYGVCHNFDAY-miniPeg-DEDEDE |

TABLE 11-continued

| SEQ ID NO: | Sequence |
|---|---|
| 173 | SSCLIDIYGVCHNFDAY-miniPeg-miniPeg-HKKNNPKKKNKTRG-miniPeg-RRRRRRR-K(Biotin) |
| 174 | (AUD)6-SSHRTNHKKNNPKKKNKTR-GSSG-K(RRRRRRR-biotin) |
| | polyethyleneimine, MW = 800,000 (PEI (800K)) |
| | polyethyleneimine, MW = 70,000 (PEI (70K)) |
| | polyethyleneimine, MW = 25,000 (PEI (25K)) |
| | polyethyleneimine, MW = 10,000 (PEI (10K)) |

TABLE 12

| Vancomycin Load (pmol/cm2) | Metal Substrate Binding Sequence SEQ ID NO: | Vancomycin Binding Sequence SEQ ID NO: |
|---|---|---|
| Controls | | |
| <10 | none | none |
| <10 | 156 | none |
| Substrate Binding Peptides with Charged Interaction Tags | | |
| 8,591 | 156 | 167 |
| 11,000 | 156 | 168 |
| 10,050 | 156 | 169 |
| 32,035 | 156 | 170 |
| 2,252 | 156 | 171 |
| 1,079 | 156 | 172 |
| Substrate Binding Peptides with Charged Interaction Tags & Hydrophobic Interaction Tags | | |
| 18,898 | 158 | 168 |
| 8,820 | 157 | 167 |
| 9,663 | 157 | 168 |
| 12,690 | 159 | 167 |
| 2,501 | 174 | 167 |
| 1st and 2nd Substrate Binding Peptides Linked + 2nd Substrate Binding Peptide & Charged Interaction Tag | | |
| 5,628 | 160 | 167 |
| 417 | 161 | 167 |
| 455 | 173 | 167 |
| 881 | 162 | 167 |
| Positively Charged Polymer + 2nd Substrate Binding Peptide & Charged Interaction Tag | | |
| 5,764 | PEI (800K) | 167 |
| 4,760 | PEI (70K) | 167 |
| 6,058 | PEI (25K) | 167 |
| 7,073 | PEI (10K) | 167 |
| 1st and 2nd Substrate Binding Peptides Linked +/− Hydrophobic Interaction Tags | | |
| 54 | 163 | |
| 278 | 164 | |
| 1,700 | 165 | |
| 173 | 166 | |

The experimental procedure used for the embodiments described above was as follows. A cleaned and passivated titanium bead was added to the wells of a 96-well polypropylene plate. 200 ul of the appropriate peptide or polymer (poly(ethyleneimine), MW ranging from 10,000-700,000, 30% aqueous solution=30 mM (POLYSCIENCES #17,938)) and vancomycin mixture was added to each bead set (triplicates). The first substrate binding peptide and second substrate binding peptide were added at concentrations ranging from 50-200 uM and the vancomycin was added at concentrations ranging from 200-600 uM. All three components were mixed and then applied to the metal bead. The first substrate binding polymer was added at a concentration ranging from 10-200 uM to second substrate binding peptide was added at a concentration ranging from 50-1000 uM and the vancomycin added at a concentration ranging from 200-1500 uM. All three components were mixed and then applied to the metal bead. The molecule with the first substrate binding peptide covalently linked to second substrate binding peptide was added at a concentration ranging from 50-200 uM and the vancomycin added at a concentration ranging from 200-600 uM. The molecule with the first substrate binding peptide covalently linked to second substrate binding peptide was added at a concentration ranging from 50-200 uM and the second substrate binding peptide was added at a concentration ranging from 50-200 uM and the vancomycin was added at a concentration ranging from 200-600 uM. The mixtures were applied to the metal beads and incubated for 30 mins at 20° C. with 700 rpm shaking. The beads were washed three times with 350ul PBS. Beads were analyzed as follows: 200 ul of 100 mM HCl was added to each bead and incubated for 30 mins at 20° C. with 1,000 rpm shaking. The eluate from each bead was analyzed by HPLC using Phenomenex Luna 3 um column, 50×4.60 mm. Output was compared to a standard curve for vancomycin to determine the amount of vancomycin retained onto the metal bead.

To access the ability of the coated beads to bind, retain and release a quantity of vancomycin sufficient to kill bacteria, beads were coated as described above. Coated beads were transferred to the wells of a polypropylene 96-well plate. 150 ul of human plasma was added to each well and incubated at 37° C. with 250 rpm shaking. Plasma was removed after 1 hr and assayed for antibiotic activity. To measure inhibition of bacterial growth, 100 ul of the sample was added to 100 ul of TSB medium and inoculated with 10 ul of *S. aureus* (OD600 of 0.1, diluted 14 fold in TSB). The plate was sealed with an aluminum cover and incubated for 18 h at 37° C. with 250 rpm shaking. Positive and negative controls (minus bacteria/minus antibiotic; (plus bacteria/minus antibiotic; plus bacteria/plus antibiotic) were prepared and run in parallel. 100 ul of the solution in each well was transferred to Costar 9017 polystyrene plate and the absorbance read at 600 nm. The level of vancomycin loading on the beads is shown in Table 12. The coatings in Table x that delivered >100 pmol/cm2 showed inhibition of *S. aureus* growth.

Example 19

In vivo Prevention of Bacterial Colonization of a Coated Titanium Implant

This Example describes the delivery of vancomycin from a titanium implant coated with a composition of the presently disclosed subject matter that prevents implant colonization by *Staphylococcus aureus* in vivo. The goal of this experiment was to assess the ability of the self-assembling peptides SEQ ID NO: 158/SEQ ID NO:168 to deliver vancomycin from the surface of a titanium implant and prevent implant colonization in an infected tibia of a rat. Peptides SEQ ID NO: 158, SEQ ID NO: 168 and vancomycin were mixed at a final concentration of 100 uM, 100 uM and 600 uM, respectively in phosphate buffered saline (PBS). 12 mm×0.8 mm titanium pins were cleaned by sonication in a succession of solutions, water, acetone, 10% Contrad, water, 10% Citrisurf, water for 15-30 min each. After cleaning, the titanium was passivated by treatment with 20% nitric acid for 30 min followed by multiple washes with distilled water. Pins were dried and stored under nitrogen. 15 pins were placed into microfuge tubes and coated with the peptide/vancomycin mixture for 20 min at room temperature.

*Staphylococcus aureus* was grown overnight at 37 C on a Blood Agar plate. Colonies were picked from the plate and resuspended in Trypticase Soy Broth (TSB) at an optical density (OD) of 0.2 which represents $2\times10^6$ CFU per 10 uL. *S. aureus* was then diluted to $10^4$ CFU per 10 uL in saline. Rats were anaesthetized with isoflurane and their left hind leg was shaved, depilated, and disinfected. Skin and fascia at the proximal tibial metaphysis was incised and a hole bored into the top of the tibia to access the medullary cavity at the proximal metaphysis. After reaming out the medullary cavity, $10^4$ CFU in 10 uL of *S. aureus* was added followed by the insertion of either a treated or untreated titanium pin. The incision was sutured and the rats allowed to recover. After 48 hr, the rats were euthanized and the titanium pins removed from the tibia. Pins were sonicated to remove *S. aureus* that had colonized the pins and the sonicates were plated onto TSA plates. After overnight incubation at 37 C, the number of colonies on the plates were counted and used to determine the number of bacteria that had colonized the titanium implants. The animal protocol was repeated to give a total of 24 treated and 24 untreated samples. The results are shown in table 13.

TABLE 13

*S. aureus* colonization of titanium implants in infected rat tibia

| Untreated | | Treated | |
|---|---|---|---|
| Animal # | CFU on Pin | Animal # | CFU on Pin |
| 1 | 46000 | 3 | 0 |
| 2 | 0 | 5 | 0 |
| 4 | 0 | 6 | 0 |
| 7 | 4600 | 8 | 0 |
| 11 | 225000 | 9 | 0 |
| 12 | 0 | 10 | 0 |
| 13 | 6200 | 15 | 0 |
| 14 | 17500 | 16 | 0 |
| 19 | 350 | 17 | 0 |
| 20 | 1950 | 18 | 0 |
| 21 | 1200 | 22 | 0 |
| 24 | 20000 | 23 | 0 |
| 25 | 8050 | 26 | 0 |
| 30 | 1200 | 27 | 0 |
| 33 | 34500 | 28 | 0 |
| 35 | 0 | 29 | 0 |
| 36 | 0 | 31 | 0 |
| 37 | 0 | 32 | 0 |
| 38 | 1250 | 34 | 0 |
| 40 | 11000 | 39 | 0 |
| 42 | 37500 | 41 | 0 |
| 44 | 0 | 43 | 0 |
| 45 | 300 | 46 | 0 |
| 47 | 150 | 48 | 0 |

Analysis of the colonization of the titanium pins showed 71% of the untreated pins were colonized with *S. aureus* while none of the pins treated with the peptide/vancomycin mixture were colonized.

Example 20

Crosslinking of the Compositions of the Presently Disclosed Subject Matter

This Example describes how an additional crosslinking step can be applied to achieve covalent crosslinks between the substrate binding peptides comprised in the macromolecular network of the presently disclosed subject matte. The following surface binding peptides (SBD-1 and SBD-2) were synthesized for crosslinking strategy for implementation after non-covalent coupling of the surface binding peptides as described herein above. A first surface binding peptide is synthesized using standard peptide chemistry described previously and an additional cysteine residue is incorporated at the N-terminus (e.g., Cys-RRRRRRR-P-SSHRTNHKKN-NPKKKNKTRG-P-RRRRRRR-K (Biotin)-amide; (SEQ ID NO: 175)). The peptide is purified by HPLC under reduced conditions. A second surface binding peptide, for example,: Maleoyl-propionic acid-SSCLIDIYGVCHNFDAY-DDDDDD-amide (SEQ ID NO: 176) is synthesized using standard peptide chemistry and the cyclization and purification is carried out using Acetonitrile/TFA (0.1% TFA) method. A 3-Maleimidopropionic acid N-hydroxysuccinimide ester (Obiter Research, LLC) (MPA) group is coupled at the N-terminus of the peptide sequence of SEQ ID NO: X in DMF using excess TEA as base. The MPA-peptide conjugate is purified by HPLC and the lyophilized solid is stored at −20 C. Care is taken to avoid hydrolysis of the MPA group. A crosslink is formed between the first (SBD-1) and second (SBD-2) substrate binding peptides as follows. Dissolve SBD-1 and SBD-2 peptide (5 fold excess) is dissolved in PBS buffer—Adjust pH to 7.5. The cysteine sulfhydryls in SBD-1 undergo covalent addition across the maleimide group to form a thioether bridge. This cross-linking reaction can be facilitated due to the association of the peptides by virtue of self assembly. The covalent complex formation is confirmed by LC-MS.

Example 21

Substrate Binding Peptides having Binding Affinity for Demineralized Bone Matrix This Example describes substrate binding peptides having binding affinity for a substrate tissue that is bone discovered according to the methods for utilizing phage display technology outlined herein previously in Example 1. More specifically, the following subject matter describing substrate-binding peptides having binding affinity for a substrate tissue that is bone taken from PCT International Patent Application Publication No. WO/2008/134329A1, which is herein incorporated by reference in its entirety.

Illustrative substrate binding peptides according to the presently disclosed subject matter having binding affinity for a substrate tissue that is bone were described in PCT International Patent Application Publication No. WO/2008/134329A1 and conform to the following sequence motif 1: ZZXZZXXXXXXXZ (SEQ ID NO:177) and sequence motif 2: ZXXZZZXXXXXX (SEQ ID NO:178); wherein Z is F (phenylalanine), W (tryptophan), or Y (tyrosine); and X is any amino acid. The peptides were shown to have binding affinity for bone, including demineralized bone matrix, demineralized cortical bone, and cancellous bone. The illustrative peptides are further covalently coupled to one or both a hydrophobic interaction tag and a charged interaction tag according to the methods detailed herein at Example 12.

The foregoing description of the specific embodiments of the present invention has been described in detail for purposes of illustration. In view of the descriptions and illustrations, others skilled in the art can, by applying, current knowledge, readily modify and/or adapt the present invention for various applications without departing from the basic concept of the present invention; and thus, such modifications and/or adaptations are intended to be within the meaning and scope of the appended claims.

What is claimed is:

1. A composition comprising:

(a) a plurality of first molecules comprising:

(i) a first substrate-binding peptide comprising 6 to 40 amino acids and comprising an amino acid sequence selected from the group consisting of SEQ ID NOs: 55-112, 122-123, and 138-139, wherein the first substrate is a titanium or steel medical device and the first substrate-binding peptide has binding affinity for the medical device; and (ii) a second substrate-binding peptide comprising 6 to 40 amino acids, wherein the second substrate is a vancomycin antibiotic and the second substrate-binding peptide comprises an amino acid sequence selected from the group consisting of SEQ ID NOs: 124-126 and 131-137, and has binding affinity for the vancomycin antibiotic, wherein the first and second substrate-binding peptides are covalently linked; and (b) a plurality of second molecules comprising:

the second substrate-binding peptide, wherein the second substrate-binding peptide is not covalently linked to the first substrate-binding peptide; and (c) a plurality of the target molecule, vancomycin, wherein each of the plurality of first and second molecules are covalently coupled to at least one interaction tag selected from the group consisting of a positively charged interaction tag and a negatively charged interaction tag, wherein the positively charged interaction tags interact with the negatively charged interaction tags to form a macromolecular network comprising the plurality of non-covalently coupled first and second molecules.

2. The composition of claim 1, wherein the plurality of first molecules, the plurality of second molecules, and the target molecule are present in a pharmaceutically acceptable solution.

3. The composition of claim 2, wherein the pharmaceutically acceptable solution is in the form of a gel.

4. The composition of claim 1, wherein the charged interaction tag is selected from the group consisting of polylysine, polyarginine, polyamines, polyimines, polyethylamines, polyethylenimines (PEI), polyaspartic acid, polyglutamic acid, polystyrene sulfonate, poly(styrenesulfonic-maleic acid), and combinations and copolymers thereof.

5. The composition of claim 1, wherein the first and second substrate-binding peptides are covalently linked by any one of the charged interaction tag, amino acids, polymers, synthetic polymers, polyethers, poly(ethylene glycol) ("PEG"), a 10 unit polyethylene glycol ("P10"), and a 6 unit polyethylene glycol ("MP").

6. A method for coating a titanium or steel medical device, the method comprising contacting a composition with the metal-medical device, the composition comprising:

(a) a plurality of first molecules comprising:

(i) a first substrate-binding peptide comprising 6 to 40 amino acids and comprising an amino acid sequence selected from the group consisting of SEQ ID NOs: 55-112, 122-123, and 138-139, wherein the first substrate is the titanium or steel medical device and the first substrate-binding peptide has binding affinity for the medical device; and (ii) a second substrate-binding peptide comprising 6 to 40 amino acids, wherein the second substrate is a vancomycin antibiotic and the second substrate-binding peptide comprises an amino acid sequence selected from the group consisting of SEQ ID NOs: 124-126 and 131-137, and has binding affinity for the target molecule, wherein the first and second substrate-binding peptides are covalently linked; and (b) a plurality of second molecules comprising:

(i) the second substrate-binding peptide, wherein the second substrate-binding peptide is not covalently linked to the first substrate-binding peptide; and (c) a plurality of the target molecule, vancomycin, wherein each of the plurality of first and second molecules are covalently coupled to at least one interaction tag selected from the group consisting of a positively charged interaction tag and a negatively charged interaction tag, wherein the positively charged interaction tags interact with the negatively charged interaction tags to form a macromolecular network comprising the plurality of non-covalently coupled first and second molecules.

7. The method of claim 6, wherein the charged interaction tag is selected from the group consisting of polylysine, polyarginine, polyamines, polyimines, polyethylamines, polyethylenimines (PEI), polyaspartic acid, polyglutamic acid, polystyrene sulfonate, poly(styrenesulfonic-maleic acid), and combinations and copolymers thereof.

8. The method of claim 6, wherein the first and second substrate-binding peptides are covalently linked by any one of the charged interaction tag, amino acids, polymers, synthetic polymers, polyethers, poly(ethylene glycol) ("PEG"), a 10 unit polyethylene glycol ("P10"), and a 6 unit polyethylene glycol ("MP").

* * * * *

SEQUENCE LISTING

<160> NUMBER OF SEQ ID NOS: 178

<210> SEQ ID NO 1
<211> LENGTH: 13
<212> TYPE: PRT
<213> ORGANISM: Artificial
<220> FEATURE:
<223> OTHER INFORMATION: synthesized

<400> SEQUENCE: 1

Phe Leu Ser Phe Val Phe Pro Ala Ser Ala Trp Gly Gly
1 5 10

<210> SEQ ID NO 2
<211> LENGTH: 13
<212> TYPE: PRT
<213> ORGANISM: Artificial
<220> FEATURE:
<223> OTHER INFORMATION: Synthesized

<400> SEQUENCE: 2

Phe Tyr Met Pro Phe Gly Pro Thr Trp Trp Gln His Val
1 5 10

<210> SEQ ID NO 3
<211> LENGTH: 13
<212> TYPE: PRT
<213> ORGANISM: Artificial
<220> FEATURE:
<223> OTHER INFORMATION: Synthesized

<400> SEQUENCE: 3

Leu Phe Ser Trp Phe Leu Pro Thr Asp Asn Tyr Pro Val
1 5 10

<210> SEQ ID NO 4
<211> LENGTH: 13
<212> TYPE: PRT
<213> ORGANISM: Artificial
<220> FEATURE:
<223> OTHER INFORMATION: Synthesized

<400> SEQUENCE: 4

Phe Met Asp Ile Trp Ser Pro Trp His Leu Leu Gly Thr
1 5 10

<210> SEQ ID NO 5
<211> LENGTH: 13
<212> TYPE: PRT
<213> ORGANISM: Artificial
<220> FEATURE:
<223> OTHER INFORMATION: Synthesized

<400> SEQUENCE: 5

Phe Ser Ser Leu Phe Phe Pro His Trp Pro Ala Gln Leu
1 5 10

<210> SEQ ID NO 6
<211> LENGTH: 19
<212> TYPE: PRT
<213> ORGANISM: Artificial
<220> FEATURE:
<223> OTHER INFORMATION: Synthesized

<400> SEQUENCE: 6

Ser Cys Ala Met Ala Gln Trp Phe Cys Asp Arg Ala Glu Pro His His 1 5 10 15

Val Ile Ser

<210> SEQ ID NO 7
<211> LENGTH: 19
<212> TYPE: PRT
<213> ORGANISM: Artificial
<220> FEATURE:
<223> OTHER INFORMATION: Artificial

<400> SEQUENCE: 7

Ser Cys Asn Met Ser His Leu Thr Gly Val Ser Leu Cys Asp Ser Leu
1 5 10 15

Ala Thr Ser

<210> SEQ ID NO 8
<211> LENGTH: 19
<212> TYPE: PRT
<213> ORGANISM: Artificial
<220> FEATURE:
<223> OTHER INFORMATION: synthesized

<400> SEQUENCE: 8

Ser Cys Val Tyr Ser Phe Ile Asp Gly Ser Gly Cys Asn Ser His Ser
1 5 10 15

Leu Gly Ser

<210> SEQ ID NO 9
<211> LENGTH: 19
<212> TYPE: PRT
<213> ORGANISM: Artificial
<220> FEATURE:
<223> OTHER INFORMATION: synthesized

<400> SEQUENCE: 9

Ser Cys Ser Gly Phe His Leu Leu Cys Glu Ser Arg Ser Met Gln Arg
1 5 10 15

Glu Leu Ser

<210> SEQ ID NO 10
<211> LENGTH: 19
<212> TYPE: PRT
<213> ORGANISM: Artificial
<220> FEATURE:
<223> OTHER INFORMATION: synthesized

<400> SEQUENCE: 10

Ser Cys Gly Ile Leu Cys Ser Ala Phe Pro Phe Asn Asn His Gln Val
1 5 10 15

Gly Ala Ser

<210> SEQ ID NO 11
<211> LENGTH: 19
<212> TYPE: PRT
<213> ORGANISM: Artificial
<220> FEATURE:
<223> OTHER INFORMATION: synthesized

<400> SEQUENCE: 11

Ser Cys Cys Ser Met Phe Phe Lys Asn Val Ser Tyr Val Gly Ala Ser
1 5 10 15

Asn Pro Ser

<210> SEQ ID NO 12
<211> LENGTH: 19
<212> TYPE: PRT
<213> ORGANISM: Artificial
<220> FEATURE:
<223> OTHER INFORMATION: synthesized

<400> SEQUENCE: 12

Ser Cys Pro Ile Trp Lys Tyr Cys Asp Asp Tyr Ser Arg Ser Gly Ser
1 5 10 15

Ile Phe Ser

<210> SEQ ID NO 13
<211> LENGTH: 18
<212> TYPE: PRT
<213> ORGANISM: Artificial
<220> FEATURE:
<223> OTHER INFORMATION: synthesized

<400> SEQUENCE: 13

Ser Cys Leu Phe Asn Ser Met Lys Cys Leu Val Leu Ile Leu Cys Phe
1 5 10 15

Val Ser

<210> SEQ ID NO 14
<211> LENGTH: 19
<212> TYPE: PRT
<213> ORGANISM: Artificial
<220> FEATURE:
<223> OTHER INFORMATION: synthesized

<400> SEQUENCE: 14

Ser Cys Tyr Val Asn Gly His Asn Ser Val Trp Val Val Val Phe Trp
1 5 10 15

Gly Val Ser

<210> SEQ ID NO 15
<211> LENGTH: 19
<212> TYPE: PRT
<213> ORGANISM: Artificial
<220> FEATURE:
<223> OTHER INFORMATION: synthesized

<400> SEQUENCE: 15

Ser Cys Asp Phe Val Cys Asn Val Leu Phe Asn Val Asn His Gly Ser
1 5 10 15

Asn Met Ser

<210> SEQ ID NO 16
<211> LENGTH: 19
<212> TYPE: PRT
<213> ORGANISM: Artificial
<220> FEATURE:
<223> OTHER INFORMATION: synthesized

<400> SEQUENCE: 16

Ser Cys Leu Asn Lys Phe Phe Val Leu Met Ser Val Gly Leu Arg Ser
1 5 10 15

Tyr Thr Ser

<210> SEQ ID NO 17
<211> LENGTH: 19
<212> TYPE: PRT
<213> ORGANISM: Artificial
<220> FEATURE:

<223> OTHER INFORMATION: synthesized

<400> SEQUENCE: 17

Ser Cys Cys Asn His Asn Ser Thr Ser Val Lys Asp Val Gln Phe Pro
1 5 10 15

Thr Leu Ser

<210> SEQ ID NO 18
<211> LENGTH: 13
<212> TYPE: PRT
<213> ORGANISM: Artificial
<220> FEATURE:
<223> OTHER INFORMATION: synthesized

<400> SEQUENCE: 18

Phe Phe Pro Ser Ser Trp Tyr Ser His Leu Gly Val Leu
1 5 10

<210> SEQ ID NO 19
<211> LENGTH: 13
<212> TYPE: PRT
<213> ORGANISM: Artificial
<220> FEATURE:
<223> OTHER INFORMATION: synthesized

<400> SEQUENCE: 19

Phe Phe Gly Phe Asp Val Tyr Asp Met Ser Asn Ala Leu
1 5 10

<210> SEQ ID NO 20
<211> LENGTH: 13
<212> TYPE: PRT
<213> ORGANISM: Artificial
<220> FEATURE:
<223> OTHER INFORMATION: synthesized

<400> SEQUENCE: 20

Leu Ser Phe Ser Asp Phe Tyr Phe Ser Glu Gly Ser Glu
1 5 10

<210> SEQ ID NO 21
<211> LENGTH: 13
<212> TYPE: PRT
<213> ORGANISM: Artificial
<220> FEATURE:
<223> OTHER INFORMATION: synthesized

<400> SEQUENCE: 21

Phe Ser Tyr Ser Val Ser Tyr Ala His Pro Glu Gly Leu
1 5 10

<210> SEQ ID NO 22
<211> LENGTH: 13
<212> TYPE: PRT
<213> ORGANISM: Artificial
<220> FEATURE:
<223> OTHER INFORMATION: synthesized

<400> SEQUENCE: 22

Leu Pro His Leu Ile Gln Tyr Arg Val Leu Leu Val Ser
1 5 10

<210> SEQ ID NO 23
<211> LENGTH: 19
<212> TYPE: PRT
<213> ORGANISM: Artificial
<220> FEATURE:

<223> OTHER INFORMATION: synthesized

<400> SEQUENCE: 23

Ser Cys Tyr Val Asn Gly His Asn Ser Val Trp Val Val Val Phe Trp
1 5 10 15

Gly Val Ser

<210> SEQ ID NO 24
<211> LENGTH: 19
<212> TYPE: PRT
<213> ORGANISM: Artificial
<220> FEATURE:
<223> OTHER INFORMATION: synthesized

<400> SEQUENCE: 24

Ser Cys Asn Ser Phe Met Phe Ile Asn Gly Ser Phe Lys Glu Thr Gly
1 5 10 15

Gly Cys Ser

<210> SEQ ID NO 25
<211> LENGTH: 19
<212> TYPE: PRT
<213> ORGANISM: Artificial
<220> FEATURE:
<223> OTHER INFORMATION: synthesized

<400> SEQUENCE: 25

Ser Cys Phe Gly Asn Leu Gly Asn Leu Ile Tyr Thr Cys Asp Arg Leu
1 5 10 15

Met Pro Ser

<210> SEQ ID NO 26
<211> LENGTH: 19
<212> TYPE: PRT
<213> ORGANISM: Artificial
<220> FEATURE:
<223> OTHER INFORMATION: synthesized

<400> SEQUENCE: 26

Ser Cys Ser Phe Phe Met Pro Trp Cys Asn Phe Leu Asn Gly Glu Met
1 5 10 15

Ala Val Ser

<210> SEQ ID NO 27
<211> LENGTH: 19
<212> TYPE: PRT
<213> ORGANISM: Artificial
<220> FEATURE:
<223> OTHER INFORMATION: synthesized

<400> SEQUENCE: 27

Ser Cys Phe Gly Asn Val Phe Cys Val Tyr Asn Gln Phe Ala Ala Gly
1 5 10 15

Leu Phe Ser

<210> SEQ ID NO 28
<211> LENGTH: 19
<212> TYPE: PRT
<213> ORGANISM: Artificial
<220> FEATURE:
<223> OTHER INFORMATION: synthesized

<400> SEQUENCE: 28

Ser Cys Cys Phe Ile Asn Ser Asn Phe Ser Val Met Asn His Ser Leu 1 5 10 15

Phe Lys Ser

<210> SEQ ID NO 29
<211> LENGTH: 19
<212> TYPE: PRT
<213> ORGANISM: Artificial
<220> FEATURE:
<223> OTHER INFORMATION: synthesized

<400> SEQUENCE: 29

Ser Cys Asp Tyr Phe Ser Phe Leu Glu Cys Phe Ser Asn Gly Trp Ser
1 5 10 15

Gly Ala Ser

<210> SEQ ID NO 30
<211> LENGTH: 19
<212> TYPE: PRT
<213> ORGANISM: Artificial
<220> FEATURE:
<223> OTHER INFORMATION: synthesized

<400> SEQUENCE: 30

Ser Cys Trp Met Gly Leu Phe Glu Cys Pro Asp Ala Trp Leu His Asp
1 5 10 15

Trp Asp Ser

<210> SEQ ID NO 31
<211> LENGTH: 19
<212> TYPE: PRT
<213> ORGANISM: Artificial
<220> FEATURE:
<223> OTHER INFORMATION: synthesized

<400> SEQUENCE: 31

Ser Cys Phe Trp Tyr Ser Trp Leu Cys Ser Ala Ser Ser Ser Asp Ala
1 5 10 15

Leu Ile Ser

<210> SEQ ID NO 32
<211> LENGTH: 19
<212> TYPE: PRT
<213> ORGANISM: Artificial
<220> FEATURE:
<223> OTHER INFORMATION: synthesized

<400> SEQUENCE: 32

Ser Cys Phe Gly Asn Phe Leu Ser Phe Gly Phe Asn Cys Glu Ser Ala
1 5 10 15

Leu Gly Ser

<210> SEQ ID NO 33
<211> LENGTH: 19
<212> TYPE: PRT
<213> ORGANISM: Artificial
<220> FEATURE:
<223> OTHER INFORMATION: synthesized

<400> SEQUENCE: 33

Ser Cys Leu Tyr Cys His Leu Asn Asn Gln Phe Leu Ser Trp Val Ser
1 5 10 15

Gly Asn Ser

<210> SEQ ID NO 34
<211> LENGTH: 19
<212> TYPE: PRT
<213> ORGANISM: Artificial
<220> FEATURE:
<223> OTHER INFORMATION: synthesized

<400> SEQUENCE: 34

```
Ser Cys Phe Gly Phe Ser Asp Cys Leu Ser Trp Phe Val Gln Pro Ser
1               5                   10                  15

Thr Ala Ser
```

<210> SEQ ID NO 35
<211> LENGTH: 19
<212> TYPE: PRT
<213> ORGANISM: Artificial
<220> FEATURE:
<223> OTHER INFORMATION: synthesized

<400> SEQUENCE: 35

```
Ser Cys Asn His Leu Gly Phe Phe Ser Ser Phe Cys Asp Arg Leu Val
1               5                   10                  15

Glu Asn Ser
```

<210> SEQ ID NO 36
<211> LENGTH: 19
<212> TYPE: PRT
<213> ORGANISM: Artificial
<220> FEATURE:
<223> OTHER INFORMATION: synthesized

<400> SEQUENCE: 36

```
Ser Cys Gly Tyr Phe Cys Ser Phe Tyr Asn Tyr Leu Asp Ile Gly Thr
1               5                   10                  15

Ala Ser Ser
```

<210> SEQ ID NO 37
<211> LENGTH: 19
<212> TYPE: PRT
<213> ORGANISM: Artificial
<220> FEATURE:
<223> OTHER INFORMATION: synthesized

<400> SEQUENCE: 37

```
Ser Cys Asn Ser Ser Ser Tyr Ser Trp Tyr Cys Trp Phe Gly Gly Ser
1               5                   10                  15

Ser Pro Ser
```

<210> SEQ ID NO 38
<211> LENGTH: 13
<212> TYPE: PRT
<213> ORGANISM: Artificial
<220> FEATURE:
<223> OTHER INFORMATION: synthesized

<400> SEQUENCE: 38

```
Phe Gly His Gly Trp Leu Asn Thr Leu Asn Leu Gly Trp
1               5                   10
```

<210> SEQ ID NO 39
<211> LENGTH: 13
<212> TYPE: PRT
<213> ORGANISM: Artificial
<220> FEATURE:
<223> OTHER INFORMATION: synthesized

<400> SEQUENCE: 39

Phe Ser Pro Phe Ser Ala Asn Leu Trp Tyr Asp Met Phe
1 5 10

<210> SEQ ID NO 40
<211> LENGTH: 13
<212> TYPE: PRT
<213> ORGANISM: Artificial
<220> FEATURE:
<223> OTHER INFORMATION: synthesized

<400> SEQUENCE: 40

Val Phe Val Pro Phe Gly Asn Trp Leu Ser Thr Ser Val
1 5 10

<210> SEQ ID NO 41
<211> LENGTH: 13
<212> TYPE: PRT
<213> ORGANISM: Artificial
<220> FEATURE:
<223> OTHER INFORMATION: synthesized

<400> SEQUENCE: 41

Phe Trp Asn Val Asn Tyr Asn Pro Trp Gly Trp Asn Tyr
1 5 10

<210> SEQ ID NO 42
<211> LENGTH: 13
<212> TYPE: PRT
<213> ORGANISM: Artificial
<220> FEATURE:
<223> OTHER INFORMATION: synthesized

<400> SEQUENCE: 42

Phe Tyr Trp Asp Arg Leu Asn Val Gly Trp Gly Leu Leu
1 5 10

<210> SEQ ID NO 43
<211> LENGTH: 13
<212> TYPE: PRT
<213> ORGANISM: Artificial
<220> FEATURE:
<223> OTHER INFORMATION: synthesized

<400> SEQUENCE: 43

Leu Tyr Ser Thr Met Tyr Pro Gly Met Ser Trp Leu Val
1 5 10

<210> SEQ ID NO 44
<211> LENGTH: 19
<212> TYPE: PRT
<213> ORGANISM: Artificial
<220> FEATURE:
<223> OTHER INFORMATION: synthesized

<400> SEQUENCE: 44

Ser Cys Phe Tyr Gln Asn Val Ile Ser Ser Ser Phe Ala Gly Asn Pro
1 5 10 15

Trp Glu Cys

<210> SEQ ID NO 45
<211> LENGTH: 19
<212> TYPE: PRT
<213> ORGANISM: Artificial
<220> FEATURE:
<223> OTHER INFORMATION: synthesized

<400> SEQUENCE: 45

Ser Cys Asn Met Leu Leu Asn Ser Leu Pro Leu Pro Ser Glu Asp Trp
1 5 10 15

Ser Ala Cys

<210> SEQ ID NO 46
<211> LENGTH: 19
<212> TYPE: PRT
<213> ORGANISM: Artificial
<220> FEATURE:
<223> OTHER INFORMATION: synthesized

<400> SEQUENCE: 46

Ser Cys Pro Phe Thr His Ser Leu Ala Leu Asn Thr Asp Arg Ala Ser
1 5 10 15

Pro Gly Cys

<210> SEQ ID NO 47
<211> LENGTH: 19
<212> TYPE: PRT
<213> ORGANISM: Artificial
<220> FEATURE:
<223> OTHER INFORMATION: synthesized

<400> SEQUENCE: 47

Ser Cys Phe Glu Ser Asp Phe Pro Asn Val Arg His His Val Leu Lys
1 5 10 15

Gln Ser Cys

<210> SEQ ID NO 48
<211> LENGTH: 19
<212> TYPE: PRT
<213> ORGANISM: Artificial
<220> FEATURE:
<223> OTHER INFORMATION: synthesized

<400> SEQUENCE: 48

Ser Cys Val Phe Asp Ser Lys His Phe Ser Pro Thr His Ser Pro His
1 5 10 15

Asp Val Cys

<210> SEQ ID NO 49
<211> LENGTH: 19
<212> TYPE: PRT
<213> ORGANISM: Artificial
<220> FEATURE:
<223> OTHER INFORMATION: synthesized

<400> SEQUENCE: 49

Ser Cys Gly Asp His Met Thr Asp Lys Asn Met Pro Asn Ser Gly Ile
1 5 10 15

Ser Gly Cys

<210> SEQ ID NO 50
<211> LENGTH: 19
<212> TYPE: PRT
<213> ORGANISM: Artificial
<220> FEATURE:
<223> OTHER INFORMATION: synthesized

<400> SEQUENCE: 50

Ser Cys Asp Phe Phe Asn Arg His Gly Tyr Asn Ser Gly Cys Glu His
1 5 10 15

Ser Val Cys

<210> SEQ ID NO 51
<211> LENGTH: 19
<212> TYPE: PRT
<213> ORGANISM: Artificial
<220> FEATURE:
<223> OTHER INFORMATION: synthesized

<400> SEQUENCE: 51

Ser Cys Gly Asp His Met Thr Asp Lys Asn Met Pro Asn Ser Gly Ile
1 5 10 15

Ser Gly Cys

<210> SEQ ID NO 52
<211> LENGTH: 19
<212> TYPE: PRT
<213> ORGANISM: Artificial
<220> FEATURE:
<223> OTHER INFORMATION: synthesized

<400> SEQUENCE: 52

Ser Cys Tyr Tyr Asn Gly Leu Val Val His His Ser Asn Ser Gly His
1 5 10 15

Lys Asp Cys

<210> SEQ ID NO 53
<211> LENGTH: 18
<212> TYPE: PRT
<213> ORGANISM: Artificial
<220> FEATURE:
<223> OTHER INFORMATION: synthesized

<400> SEQUENCE: 53

Cys Trp Ser Arg Phe Arg Leu Phe Met Leu Phe Cys Met Phe Tyr Leu
1 5 10 15

Val Ser

<210> SEQ ID NO 54
<211> LENGTH: 18
<212> TYPE: PRT
<213> ORGANISM: Artificial
<220> FEATURE:
<223> OTHER INFORMATION: synthesized

<400> SEQUENCE: 54

Cys Ile Lys Tyr Pro Phe Leu Tyr Cys Cys Leu Leu Ser Leu Phe Leu
1 5 10 15

Phe Ser

<210> SEQ ID NO 55
<211> LENGTH: 19
<212> TYPE: PRT
<213> ORGANISM: Artificial
<220> FEATURE:
<223> OTHER INFORMATION: synthesized

<400> SEQUENCE: 55

Ser Cys Phe Trp Phe Leu Arg Trp Ser Leu Phe Ile Val Leu Phe Thr
1 5 10 15

Cys Cys Ser

<210> SEQ ID NO 56
<211> LENGTH: 19

<212> TYPE: PRT
<213> ORGANISM: Artificial
<220> FEATURE:
<223> OTHER INFORMATION: synthesized

<400> SEQUENCE: 56

Ser Cys Glu Ser Val Asp Cys Phe Ala Asp Ser Arg Met Ala Lys Val
1 5 10 15

Ser Met Ser

<210> SEQ ID NO 57
<211> LENGTH: 19
<212> TYPE: PRT
<213> ORGANISM: Artificial
<220> FEATURE:
<223> OTHER INFORMATION: synthesized

<400> SEQUENCE: 57

Ser Cys Val Gly Phe Phe Cys Ile Thr Gly Ser Asp Val Ala Ser Val
1 5 10 15

Asn Ser Ser

<210> SEQ ID NO 58
<211> LENGTH: 19
<212> TYPE: PRT
<213> ORGANISM: Artificial
<220> FEATURE:
<223> OTHER INFORMATION: synthesized

<400> SEQUENCE: 58

Ser Cys Ser Asp Cys Leu Lys Ser Val Asp Phe Ile Pro Ser Ser Leu
1 5 10 15

Ala Ser Ser

<210> SEQ ID NO 59
<211> LENGTH: 19
<212> TYPE: PRT
<213> ORGANISM: Artificial
<220> FEATURE:
<223> OTHER INFORMATION: synthesized

<400> SEQUENCE: 59

Ser Cys Ala Phe Asp Cys Pro Ser Ser Val Ala Arg Ser Pro Gly Glu
1 5 10 15

Trp Ser Ser

<210> SEQ ID NO 60
<211> LENGTH: 18
<212> TYPE: PRT
<213> ORGANISM: Artificial
<220> FEATURE:
<223> OTHER INFORMATION: synthesized

<400> SEQUENCE: 60

Ser Cys Val Asp Val Met His Ala Asp Ser Pro Gly Pro Asp Gly Leu
1 5 10 15

Asn Ser

<210> SEQ ID NO 61
<211> LENGTH: 19
<212> TYPE: PRT
<213> ORGANISM: Artificial
<220> FEATURE:
<223> OTHER INFORMATION: synthesized

<400> SEQUENCE: 61

Ser Cys Ser Ser Phe Glu Val Ser Glu Met Phe Thr Cys Ala Val Ser
1 5 10 15

Ser Tyr Ser

<210> SEQ ID NO 62
<211> LENGTH: 19
<212> TYPE: PRT
<213> ORGANISM: Artificial
<220> FEATURE:
<223> OTHER INFORMATION: synthesized

<400> SEQUENCE: 62

Ser Cys Gly Leu Asn Phe Pro Leu Cys Ser Phe Val Asp Phe Ala Gln
1 5 10 15

Asp Ala Ser

<210> SEQ ID NO 63
<211> LENGTH: 19
<212> TYPE: PRT
<213> ORGANISM: Artificial
<220> FEATURE:
<223> OTHER INFORMATION: synthesized

<400> SEQUENCE: 63

Ser Cys Met Leu Phe Ser Ser Val Phe Asp Cys Gly Met Leu Ile Ser
1 5 10 15

Asp Leu Ser

<210> SEQ ID NO 64
<211> LENGTH: 19
<212> TYPE: PRT
<213> ORGANISM: Artificial
<220> FEATURE:
<223> OTHER INFORMATION: synthesized

<400> SEQUENCE: 64

Ser Cys Val Asp Tyr Val Met His Ala Asp Ser Pro Gly Pro Asp Gly
1 5 10 15

Leu Asn Ser

<210> SEQ ID NO 65
<211> LENGTH: 19
<212> TYPE: PRT
<213> ORGANISM: Artificial
<220> FEATURE:
<223> OTHER INFORMATION: synthesized

<400> SEQUENCE: 65

Ser Cys Ser Glu Asn Phe Met Phe Asn Met Tyr Gly Thr Gly Val Cys
1 5 10 15

Thr Glu Ser

<210> SEQ ID NO 66
<211> LENGTH: 13
<212> TYPE: PRT
<213> ORGANISM: Artificial
<220> FEATURE:
<223> OTHER INFORMATION: synthesized

<400> SEQUENCE: 66

His Lys His Pro Val Thr Pro Arg Phe Phe Val Val Glu
1 5 10

<210> SEQ ID NO 67
<211> LENGTH: 18
<212> TYPE: PRT
<213> ORGANISM: Artificial
<220> FEATURE:
<223> OTHER INFORMATION: synthesized

<400> SEQUENCE: 67

Cys Asn Cys Tyr Val Thr Pro Asn Leu Leu Lys His Lys Cys Tyr Lys
1 5 10 15

Ile Cys

<210> SEQ ID NO 68
<211> LENGTH: 18
<212> TYPE: PRT
<213> ORGANISM: Artificial
<220> FEATURE:
<223> OTHER INFORMATION: synthesized

<400> SEQUENCE: 68

Cys Ser His Asn His His Lys Leu Thr Ala Lys His Gln Val Ala His
1 5 10 15

Lys Cys

<210> SEQ ID NO 69
<211> LENGTH: 18
<212> TYPE: PRT
<213> ORGANISM: Artificial
<220> FEATURE:
<223> OTHER INFORMATION: synthesized

<400> SEQUENCE: 69

Cys Asp Gln Asn Asp Ile Phe Tyr Thr Ser Lys Lys Ser His Lys Ser
1 5 10 15

His Cys

<210> SEQ ID NO 70
<211> LENGTH: 18
<212> TYPE: PRT
<213> ORGANISM: Artificial
<220> FEATURE:
<223> OTHER INFORMATION: synthesized

<400> SEQUENCE: 70

Ser Ser Asp Val Tyr Leu Val Ser His Lys His His Leu Thr Arg His
1 5 10 15

Asn Ser

<210> SEQ ID NO 71
<211> LENGTH: 18
<212> TYPE: PRT
<213> ORGANISM: Artificial
<220> FEATURE:
<223> OTHER INFORMATION: synthesized

<400> SEQUENCE: 71

Ser Asp Lys Cys His Lys His Trp Tyr Cys Tyr Glu Ser Lys Tyr Gly
1 5 10 15

Gly Ser

<210> SEQ ID NO 72
<211> LENGTH: 18
<212> TYPE: PRT
<213> ORGANISM: Artificial

<220> FEATURE:
<223> OTHER INFORMATION: synthesized

<400> SEQUENCE: 72

Ser Asp Lys Ser His Lys His Trp Tyr Ser Tyr Glu Ser Lys Tyr Gly
1 5 10 15

Gly Ser

<210> SEQ ID NO 73
<211> LENGTH: 14
<212> TYPE: PRT
<213> ORGANISM: Artificial
<220> FEATURE:
<223> OTHER INFORMATION: synthesized

<400> SEQUENCE: 73

His His Lys Leu Lys His Gln Met Leu His Leu Asn Gly Gly
1 5 10

<210> SEQ ID NO 74
<211> LENGTH: 14
<212> TYPE: PRT
<213> ORGANISM: Artificial
<220> FEATURE:
<223> OTHER INFORMATION: synthesized

<400> SEQUENCE: 74

Gly His His His Lys Lys Asp Gln Leu Pro Gln Leu Gly Gly
1 5 10

<210> SEQ ID NO 75
<211> LENGTH: 17
<212> TYPE: PRT
<213> ORGANISM: Artificial
<220> FEATURE:
<223> OTHER INFORMATION: synthesized

<400> SEQUENCE: 75

Ser Ser His Lys His Pro Val Thr Pro Arg Phe Phe Val Val Glu Ser
1 5 10 15

Arg

<210> SEQ ID NO 76
<211> LENGTH: 22
<212> TYPE: PRT
<213> ORGANISM: Artificial
<220> FEATURE:
<223> OTHER INFORMATION: synthesized

<400> SEQUENCE: 76

Ser Ser Cys Asn Cys Tyr Val Thr Pro Asn Leu Leu Lys His Lys Cys
1 5 10 15

Tyr Lys Ile Cys Ser Arg
20

<210> SEQ ID NO 77
<211> LENGTH: 22
<212> TYPE: PRT
<213> ORGANISM: Artificial
<220> FEATURE:
<223> OTHER INFORMATION: synthesized

<400> SEQUENCE: 77

Ser Ser Cys Ser His Asn His His Lys Leu Thr Ala Lys His Gln Val
1 5 10 15

```
Ala His Lys Cys Ser Arg
            20


<210> SEQ ID NO 78
<211> LENGTH: 22
<212> TYPE: PRT
<213> ORGANISM: Artificial
<220> FEATURE:
<223> OTHER INFORMATION: synthesized

<400> SEQUENCE: 78

Ser Ser Cys Asp Gln Asn Asp Ile Phe Tyr Thr Ser Lys Lys Ser His
1               5                   10                  15

Lys Ser His Cys Ser Arg
            20


<210> SEQ ID NO 79
<211> LENGTH: 22
<212> TYPE: PRT
<213> ORGANISM: Artificial
<220> FEATURE:
<223> OTHER INFORMATION: synthesized

<400> SEQUENCE: 79

Ser Ser Ser Ser Asp Val Tyr Leu Val Ser His Lys His His Leu Thr
1               5                   10                  15

Arg His Asn Ser Ser Arg
            20


<210> SEQ ID NO 80
<211> LENGTH: 22
<212> TYPE: PRT
<213> ORGANISM: Artificial
<220> FEATURE:
<223> OTHER INFORMATION: synthesized

<400> SEQUENCE: 80

Ser Ser Ser Asp Lys Cys His Lys His Trp Tyr Cys Tyr Glu Ser Lys
1               5                   10                  15

Tyr Gly Gly Ser Ser Arg
            20


<210> SEQ ID NO 81
<211> LENGTH: 14
<212> TYPE: PRT
<213> ORGANISM: Artificial
<220> FEATURE:
<223> OTHER INFORMATION: synthesized

<400> SEQUENCE: 81

His His Lys Leu Lys His Gln Met Leu His Leu Asn Gly Gly
1               5                   10


<210> SEQ ID NO 82
<211> LENGTH: 14
<212> TYPE: PRT
<213> ORGANISM: Artificial
<220> FEATURE:
<223> OTHER INFORMATION: synthesized

<400> SEQUENCE: 82

Gly His His His Lys Lys Asp Gln Leu Pro Gln Leu Gly Gly
1               5                   10


<210> SEQ ID NO 83
<211> LENGTH: 13
```

<212> TYPE: PRT
<213> ORGANISM: Artificial
<220> FEATURE:
<223> OTHER INFORMATION: synthesized

<400> SEQUENCE: 83

Cys Phe Val Leu Asn Cys His Leu Val Leu Asp Arg Pro
1 5 10

<210> SEQ ID NO 84
<211> LENGTH: 19
<212> TYPE: PRT
<213> ORGANISM: Artificial
<220> FEATURE:
<223> OTHER INFORMATION: synthesized

<400> SEQUENCE: 84

Ser Cys Phe Gly Asn Phe Leu Ser Phe Gly Phe Asn Cys Glu Tyr Ala
1 5 10 15

Leu Gly Ser

<210> SEQ ID NO 85
<211> LENGTH: 13
<212> TYPE: PRT
<213> ORGANISM: Artificial
<220> FEATURE:
<223> OTHER INFORMATION: synthesized

<400> SEQUENCE: 85

Asp Gly Phe Phe Ile Leu Tyr Lys Asn Pro Asp Val Leu
1 5 10

<210> SEQ ID NO 86
<211> LENGTH: 7
<212> TYPE: PRT
<213> ORGANISM: Artificial
<220> FEATURE:
<223> OTHER INFORMATION: synthesized

<400> SEQUENCE: 86

Asn His Gln Asn Gln Thr Asn
1 5

<210> SEQ ID NO 87
<211> LENGTH: 7
<212> TYPE: PRT
<213> ORGANISM: Artificial
<220> FEATURE:
<223> OTHER INFORMATION: synthesized

<400> SEQUENCE: 87

Ala Thr His Met Val Gly Ser
1 5

<210> SEQ ID NO 88
<211> LENGTH: 7
<212> TYPE: PRT
<213> ORGANISM: Artificial
<220> FEATURE:
<223> OTHER INFORMATION: synthesized

<400> SEQUENCE: 88

Gly Ile Asn Pro Asn Phe Ile
1 5

<210> SEQ ID NO 89
<211> LENGTH: 7

<212> TYPE: PRT
<213> ORGANISM: Artificial
<220> FEATURE:
<223> OTHER INFORMATION: synthesized

<400> SEQUENCE: 89

Thr Ala Ile Ser Gly His Phe
1 5

<210> SEQ ID NO 90
<211> LENGTH: 13
<212> TYPE: PRT
<213> ORGANISM: Artificial
<220> FEATURE:
<223> OTHER INFORMATION: synthesized

<400> SEQUENCE: 90

Leu Tyr Gly Thr Pro Glu Tyr Ala Val Gln Pro Leu Arg
1 5 10

<210> SEQ ID NO 91
<211> LENGTH: 13
<212> TYPE: PRT
<213> ORGANISM: Artificial
<220> FEATURE:
<223> OTHER INFORMATION: synthesized

<400> SEQUENCE: 91

Cys Phe Leu Thr Gln Asp Tyr Cys Val Leu Ala Gly Lys
1 5 10

<210> SEQ ID NO 92
<211> LENGTH: 13
<212> TYPE: PRT
<213> ORGANISM: Artificial
<220> FEATURE:
<223> OTHER INFORMATION: synthesized

<400> SEQUENCE: 92

Val Leu His Leu Asp Ser Tyr Gly Pro Ser Val Pro Leu
1 5 10

<210> SEQ ID NO 93
<211> LENGTH: 13
<212> TYPE: PRT
<213> ORGANISM: Artificial
<220> FEATURE:
<223> OTHER INFORMATION: synthesized

<400> SEQUENCE: 93

Val Val Asp Ser Thr Gly Tyr Leu Arg Pro Val Ser Thr
1 5 10

<210> SEQ ID NO 94
<211> LENGTH: 13
<212> TYPE: PRT
<213> ORGANISM: Artificial
<220> FEATURE:
<223> OTHER INFORMATION: synthesized

<400> SEQUENCE: 94

Val Leu Gln Asn Ala Thr Asn Val Ala Pro Phe Val Thr
1 5 10

<210> SEQ ID NO 95
<211> LENGTH: 13
<212> TYPE: PRT
<213> ORGANISM: Artificial

<220> FEATURE:
<223> OTHER INFORMATION: synthesized

<400> SEQUENCE: 95

Trp Trp Ser Ser Met Pro Tyr Val Gly Asp Tyr Thr Ser
1 5 10

<210> SEQ ID NO 96
<211> LENGTH: 19
<212> TYPE: PRT
<213> ORGANISM: Artificial
<220> FEATURE:
<223> OTHER INFORMATION: synthesized

<400> SEQUENCE: 96

Ser Ser Tyr Phe Asn Leu Gly Leu Val Lys His Asn His Val Arg His
1 5 10 15

His Asp Ser

<210> SEQ ID NO 97
<211> LENGTH: 18
<212> TYPE: PRT
<213> ORGANISM: Artificial
<220> FEATURE:
<223> OTHER INFORMATION: synthesized

<400> SEQUENCE: 97

Cys His Asp His Ser Asn Lys Tyr Leu Lys Ser Trp Lys His Gln Gln
1 5 10 15

Asn Cys

<210> SEQ ID NO 98
<211> LENGTH: 19
<212> TYPE: PRT
<213> ORGANISM: Artificial
<220> FEATURE:
<223> OTHER INFORMATION: synthesized

<400> SEQUENCE: 98

Ser Cys Lys His Asp Ser Glu Phe Ile Lys Lys His Val His Ala Val
1 5 10 15

Lys Lys Cys

<210> SEQ ID NO 99
<211> LENGTH: 19
<212> TYPE: PRT
<213> ORGANISM: Artificial
<220> FEATURE:
<223> OTHER INFORMATION: synthesized

<400> SEQUENCE: 99

Ser Cys His His Leu Lys His Asn Thr His Lys Glu Ser Lys Met His
1 5 10 15

His Glu Cys

<210> SEQ ID NO 100
<211> LENGTH: 11
<212> TYPE: PRT
<213> ORGANISM: Artificial
<220> FEATURE:
<223> OTHER INFORMATION: synthesized

<400> SEQUENCE: 100

Val Asn Lys Met Asn Arg Leu Trp Glu Pro Leu
1 5 10

<210> SEQ ID NO 101
<211> LENGTH: 19
<212> TYPE: PRT
<213> ORGANISM: Artificial
<220> FEATURE:
<223> OTHER INFORMATION: synthesized

<400> SEQUENCE: 101

Ser Ser His Arg Thr Asn His Lys Lys Asn Asn Pro Lys Lys Lys Asn
1 5 10 15

Lys Thr Arg

<210> SEQ ID NO 102
<211> LENGTH: 19
<212> TYPE: PRT
<213> ORGANISM: Artificial
<220> FEATURE:
<223> OTHER INFORMATION: synthesized

<400> SEQUENCE: 102

Asn His Thr Ile Ser Lys Asn His Lys Lys Lys Asn Lys Asn Ser Asn
1 5 10 15

Lys Thr Arg

<210> SEQ ID NO 103
<211> LENGTH: 14
<212> TYPE: PRT
<213> ORGANISM: Artificial
<220> FEATURE:
<223> OTHER INFORMATION: synthesized

<400> SEQUENCE: 103

Ser Lys Lys His Gly Gly Lys Lys His Gly Ser Ser Gly Lys
1 5 10

<210> SEQ ID NO 104
<211> LENGTH: 14
<212> TYPE: PRT
<213> ORGANISM: Artificial
<220> FEATURE:
<223> OTHER INFORMATION: synthesized

<400> SEQUENCE: 104

Ser Lys His Lys Gly Gly Lys His Lys Gly Ser Ser Gly Lys
1 5 10

<210> SEQ ID NO 105
<211> LENGTH: 19
<212> TYPE: PRT
<213> ORGANISM: Artificial
<220> FEATURE:
<223> OTHER INFORMATION: synthesized

<400> SEQUENCE: 105

Ser His Lys His Gly Gly His Lys His Gly Gly His Lys His Gly Ser
1 5 10 15

Ser Gly Lys

<210> SEQ ID NO 106
<211> LENGTH: 14
<212> TYPE: PRT
<213> ORGANISM: Artificial
<220> FEATURE:
<223> OTHER INFORMATION: synthesized

<400> SEQUENCE: 106

Ser Lys His Lys Gly Gly His Lys His Gly Ser Ser Gly Lys
1 5 10

<210> SEQ ID NO 107
<211> LENGTH: 14
<212> TYPE: PRT
<213> ORGANISM: Artificial
<220> FEATURE:
<223> OTHER INFORMATION: synthesized

<400> SEQUENCE: 107

Ser His Lys His Gly Gly Lys His Lys Gly Ser Ser Gly Lys
1 5 10

<210> SEQ ID NO 108
<211> LENGTH: 16
<212> TYPE: PRT
<213> ORGANISM: Artificial
<220> FEATURE:
<223> OTHER INFORMATION: synthesized

<400> SEQUENCE: 108

Ser Lys His Lys Gly Gly Gly Gly Lys His Lys Gly Ser Ser Gly Lys
1 5 10 15

<210> SEQ ID NO 109
<211> LENGTH: 16
<212> TYPE: PRT
<213> ORGANISM: Artificial
<220> FEATURE:
<223> OTHER INFORMATION: synthesized

<400> SEQUENCE: 109

Ser His Lys His Gly Gly Gly Gly His Lys His Gly Ser Ser Gly Lys
1 5 10 15

<210> SEQ ID NO 110
<211> LENGTH: 14
<212> TYPE: PRT
<213> ORGANISM: Artificial
<220> FEATURE:
<223> OTHER INFORMATION: synthesized

<400> SEQUENCE: 110

Ser His Lys His Gly Gly His Lys His Gly Ser Ser Gly Lys
1 5 10

<210> SEQ ID NO 111
<211> LENGTH: 14
<212> TYPE: PRT
<213> ORGANISM: Artificial
<220> FEATURE:
<223> OTHER INFORMATION: synthesized

<400> SEQUENCE: 111

Ser His His Lys Gly Gly His His Lys Gly Ser Ser Gly Lys
1 5 10

<210> SEQ ID NO 112
<211> LENGTH: 19
<212> TYPE: PRT
<213> ORGANISM: Artificial
<220> FEATURE:
<223> OTHER INFORMATION: synthesized

<400> SEQUENCE: 112

```
Ser Lys His Lys Gly Gly Lys His Lys Gly Gly Lys His Lys Gly Ser
1               5                   10                  15

Ser Gly Lys


<210> SEQ ID NO 113
<211> LENGTH: 17
<212> TYPE: PRT
<213> ORGANISM: Artificial
<220> FEATURE:
<223> OTHER INFORMATION: synthesized

<400> SEQUENCE: 113

Gly Gly Ala Leu Gly Phe Pro Leu Lys Gly Glu Val Val Glu Gly Trp
1               5                   10                  15

Ala


<210> SEQ ID NO 114
<211> LENGTH: 13
<212> TYPE: PRT
<213> ORGANISM: Artificial
<220> FEATURE:
<223> OTHER INFORMATION: synthesized

<400> SEQUENCE: 114

Phe Asp Ile Asp Trp Ser Gly Met Arg Ser Trp Trp Gly
1               5                   10


<210> SEQ ID NO 115
<211> LENGTH: 7
<212> TYPE: PRT
<213> ORGANISM: Artificial
<220> FEATURE:
<223> OTHER INFORMATION: synthesized

<400> SEQUENCE: 115

Leu Ser Pro Ser Arg Met Lys
1               5


<210> SEQ ID NO 116
<211> LENGTH: 21
<212> TYPE: PRT
<213> ORGANISM: Artificial
<220> FEATURE:
<223> OTHER INFORMATION: synthesized

<400> SEQUENCE: 116

Ser Arg Lys Ser Ser Gln Lys Asn Pro His His Pro Lys Pro Pro Lys
1               5                   10                  15

Lys Pro Thr Ala Arg
            20


<210> SEQ ID NO 117
<211> LENGTH: 12
<212> TYPE: PRT
<213> ORGANISM: Artificial
<220> FEATURE:
<223> OTHER INFORMATION: synthesized

<400> SEQUENCE: 117

Ala Leu Pro Ser Thr Ser Ser Gln Met Pro Gln Leu
1               5                   10


<210> SEQ ID NO 118
<211> LENGTH: 23
<212> TYPE: PRT
<213> ORGANISM: Artificial
```

<220> FEATURE:
<223> OTHER INFORMATION: synthesized

<400> SEQUENCE: 118

Ser Ser Ser Cys Gln His Val Ser Leu Leu Arg Pro Ser Ala Ala Leu
1 5 10 15

Gly Pro Asp Asn Cys Ser Arg
20

<210> SEQ ID NO 119
<211> LENGTH: 12
<212> TYPE: PRT
<213> ORGANISM: Artificial
<220> FEATURE:
<223> OTHER INFORMATION: synthesized

<400> SEQUENCE: 119

His Thr Pro His Pro Asp Ala Ser Ile Gln Gly Val
1 5 10

<210> SEQ ID NO 120
<211> LENGTH: 4
<212> TYPE: PRT
<213> ORGANISM: Artificial
<220> FEATURE:
<223> OTHER INFORMATION: synthesized

<400> SEQUENCE: 120

Val Met Asn Val
1

<210> SEQ ID NO 121
<211> LENGTH: 4
<212> TYPE: PRT
<213> ORGANISM: Artificial
<220> FEATURE:
<223> OTHER INFORMATION: synthesized

<400> SEQUENCE: 121

Ala Glu Asp Gly
1

<210> SEQ ID NO 122
<211> LENGTH: 24
<212> TYPE: PRT
<213> ORGANISM: Artificial
<220> FEATURE:
<223> OTHER INFORMATION: synthesized

<400> SEQUENCE: 122

Ser Ser His Arg Thr Asn His Lys Lys Asn Asn Pro Lys Lys Lys Asn
1 5 10 15

Lys Thr Arg Gly Ser Ser Gly Lys
20

<210> SEQ ID NO 123
<211> LENGTH: 17
<212> TYPE: PRT
<213> ORGANISM: Artificial
<220> FEATURE:
<223> OTHER INFORMATION: synthesized

<400> SEQUENCE: 123

His Lys Lys Asn Asn Pro Lys Lys Lys Asn Lys Thr Arg Gly Ser Ser
1 5 10 15

Lys

<210> SEQ ID NO 124
<211> LENGTH: 24
<212> TYPE: PRT
<213> ORGANISM: Artificial
<220> FEATURE:
<223> OTHER INFORMATION: synthesized

<400> SEQUENCE: 124

```
Ser Ser Ser Cys Leu Ile Asp Met Tyr Gly Val Cys His Asn Phe Asp
1               5                   10                  15

Gly Ala Tyr Asp Ser Ser Arg Gly
            20
```

<210> SEQ ID NO 125
<211> LENGTH: 17
<212> TYPE: PRT
<213> ORGANISM: Artificial
<220> FEATURE:
<223> OTHER INFORMATION: synthesized

<400> SEQUENCE: 125

```
Ser Ser Cys Leu Ile Asp Ile Tyr Gly Val Cys His Asn Phe Asp Ala
1               5                   10                  15

Tyr
```

<210> SEQ ID NO 126
<211> LENGTH: 16
<212> TYPE: PRT
<213> ORGANISM: Artificial
<220> FEATURE:
<223> OTHER INFORMATION: synthesized

<400> SEQUENCE: 126

```
Ser Ser Cys Leu Ile Asp Ile Tyr Gly Lys Cys His Asn Pro Leu Arg
1               5                   10                  15
```

<210> SEQ ID NO 127
<211> LENGTH: 16
<212> TYPE: PRT
<213> ORGANISM: Artificial
<220> FEATURE:
<223> OTHER INFORMATION: synthesized

<400> SEQUENCE: 127

```
Lys Trp Lys Leu Phe Lys Lys Ile Gly Ala Val Leu Lys Val Leu Lys
1               5                   10                  15
```

<210> SEQ ID NO 128
<211> LENGTH: 8
<212> TYPE: PRT
<213> ORGANISM: Artificial
<220> FEATURE:
<223> OTHER INFORMATION: synthesized

<400> SEQUENCE: 128

```
Arg Ala Asp Ala Arg Ala Asp Ala
1               5
```

<210> SEQ ID NO 129
<211> LENGTH: 8
<212> TYPE: PRT
<213> ORGANISM: Artificial
<220> FEATURE:
<223> OTHER INFORMATION: synthesized

<400> SEQUENCE: 129

Tyr Trp Ala Trp Ala Tyr Ala Trp
1 5

<210> SEQ ID NO 130
<211> LENGTH: 18
<212> TYPE: PRT
<213> ORGANISM: Artificial
<220> FEATURE:
<223> OTHER INFORMATION: synthesized

<400> SEQUENCE: 130

Ser Leu Ile Asp Met Tyr Gly Val Cys His Asn Phe Asp Gly Ala Tyr
1 5 10 15

Asp Ser

<210> SEQ ID NO 131
<211> LENGTH: 18
<212> TYPE: PRT
<213> ORGANISM: Artificial
<220> FEATURE:
<223> OTHER INFORMATION: synthesized

<400> SEQUENCE: 131

Cys Leu Ile Asp Met Tyr Gly Val Cys His Asn Phe Asp Gly Ala Tyr
1 5 10 15

Asp Ser

<210> SEQ ID NO 132
<211> LENGTH: 18
<212> TYPE: PRT
<213> ORGANISM: Artificial
<220> FEATURE:
<223> OTHER INFORMATION: synthesized

<400> SEQUENCE: 132

Cys Leu Phe Asp Ile Phe Gly Val Cys His Ser Phe Asp Gly Ala Tyr
1 5 10 15

Asp Ser

<210> SEQ ID NO 133
<211> LENGTH: 14
<212> TYPE: PRT
<213> ORGANISM: Artificial
<220> FEATURE:
<223> OTHER INFORMATION: synthesized

<400> SEQUENCE: 133

Pro Cys Glu Leu Ile Asp Met Phe Gly Asn Asp His Cys Pro
1 5 10

<210> SEQ ID NO 134
<211> LENGTH: 19
<212> TYPE: PRT
<213> ORGANISM: Artificial
<220> FEATURE:
<223> OTHER INFORMATION: synthesized

<400> SEQUENCE: 134

Ser Cys Asp Met Leu Phe Cys Glu Asn Phe Ser Gly Ser Gly Asn Asn
1 5 10 15

Trp Phe Ser

<210> SEQ ID NO 135
<211> LENGTH: 12

<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Cysteine residues 1 and 12 are disulfide bonded
<220> FEATURE:
<221> NAME/KEY: MISC_FEATURE
<222> LOCATION: (2)..(4)
<223> OTHER INFORMATION: Xaa at residues 2, 3 and 4 represent any amino acid and can be present or absent
<220> FEATURE:
<221> NAME/KEY: MISC_FEATURE
<222> LOCATION: (9)..(11)
<223> OTHER INFORMATION: Xaa at residues 9, 10 and 11 represent any amino acid and can be present or absent

<400> SEQUENCE: 135

```
Cys Xaa Xaa Xaa Asp Met Phe Gly Xaa Xaa Xaa Cys
1               5                   10
```

<210> SEQ ID NO 136
<211> LENGTH: 12
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(2)
<223> OTHER INFORMATION: Xaa1 and Xaa2 are any amino acid, and either Xaa1 or Xaa2 is C, and Xaa2 can be absent if Xaa1 is C
<220> FEATURE:
<221> NAME/KEY: MISC_FEATURE
<222> LOCATION: (3)..(3)
<223> OTHER INFORMATION: Position three is L, M, I, V or A
<220> FEATURE:
<221> NAME/KEY: MISC_FEATURE
<222> LOCATION: (4)..(4)
<223> OTHER INFORMATION: Position four is I, M or F
<220> FEATURE:
<221> NAME/KEY: MISC_FEATURE
<222> LOCATION: (5)..(5)
<223> OTHER INFORMATION: Position five is D or C
<220> FEATURE:
<221> NAME/KEY: MISC_FEATURE
<222> LOCATION: (6)..(6)
<223> OTHER INFORMATION: Position six is M or I
<220> FEATURE:
<221> NAME/KEY: MISC_FEATURE
<222> LOCATION: (7)..(7)
<223> OTHER INFORMATION: Position seven is F or Y
<220> FEATURE:
<221> NAME/KEY: MISC_FEATURE
<222> LOCATION: (9)..(9)
<223> OTHER INFORMATION: Position nine is any amino acid except C or P
<220> FEATURE:
<221> NAME/KEY: MISC_FEATURE
<222> LOCATION: (10)..(10)
<223> OTHER INFORMATION: Postion 10 is any amino acid, except if position 11 or 12 is C, position 10 is not C and can be absent
<220> FEATURE:
<221> NAME/KEY: MISC_FEATURE
<222> LOCATION: (11)..(11)
<223> OTHER INFORMATION: Position 11 is C or H unless position 10 or 12 is C and then position 11 is not C
<220> FEATURE:
<221> NAME/KEY: MISC_FEATURE
<222> LOCATION: (12)..(12)
<223> OTHER INFORMATION: Position 12 is C or H unless position 10 or 11 is C and then position 12 is not C

<400> SEQUENCE: 136

```
Xaa Xaa Xaa Xaa Xaa Xaa Xaa Gly Xaa Xaa Xaa Xaa
1               5                   10
```

<210> SEQ ID NO 137
<211> LENGTH: 12
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(2)
<223> OTHER INFORMATION: Xaa1 and Xaa2 are any amino acid, and either
Xaa1 or Xaa2 is C, and Xaa2 can be absent if Xaa1 is C
<220> FEATURE:
<221> NAME/KEY: MISC_FEATURE
<222> LOCATION: (3)..(3)
<223> OTHER INFORMATION: Position 3 is any amino acid except C, G, P, Q
or T
<220> FEATURE:
<221> NAME/KEY: MISC_FEATURE
<222> LOCATION: (4)..(4)
<223> OTHER INFORMATION: Position 4 is is any amino acid except A, G, P
or S
<220> FEATURE:
<221> NAME/KEY: MISC_FEATURE
<222> LOCATION: (5)..(5)
<223> OTHER INFORMATION: Position 5 is D or C
<220> FEATURE:
<221> NAME/KEY: MISC_FEATURE
<222> LOCATION: (6)..(6)
<223> OTHER INFORMATION: Position 6 is M or I
<220> FEATURE:
<221> NAME/KEY: MISC_FEATURE
<222> LOCATION: (7)..(7)
<223> OTHER INFORMATION: Position 7 is F or Y
<220> FEATURE:
<221> NAME/KEY: MISC_FEATURE
<222> LOCATION: (8)..(8)
<223> OTHER INFORMATION: Position 8 is is any amino acid except A, R, S
or V
<220> FEATURE:
<221> NAME/KEY: MISC_FEATURE
<222> LOCATION: (9)..(9)
<223> OTHER INFORMATION: Position 9 is is any amino acid except C or P
<220> FEATURE:
<221> NAME/KEY: MISC_FEATURE
<222> LOCATION: (10)..(10)
<223> OTHER INFORMATION: Position 10 is any amino acid except if
position 11 or 12 is C, position 10 is any amino acid except C and
can be absent
<220> FEATURE:
<221> NAME/KEY: MISC_FEATURE
<222> LOCATION: (11)..(11)
<223> OTHER INFORMATION: Position 11 is C or H unless position 10 or 12
is C and then position 11 is not C
<220> FEATURE:
<221> NAME/KEY: MISC_FEATURE
<222> LOCATION: (12)..(12)
<223> OTHER INFORMATION: Position 12 is C or H unless position 10 or 11
is C and then position 12 is not C

<400> SEQUENCE: 137

```
Xaa Xaa Xaa Xaa Xaa Xaa Xaa Xaa Xaa Xaa Xaa Xaa
1               5                   10
```

<210> SEQ ID NO 138
<211> LENGTH: 16
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Postion 1 is K, N, or S
<220> FEATURE:
<221> NAME/KEY: MISC_FEATURE
<222> LOCATION: (3)..(4)

<223> OTHER INFORMATION: Postion 3 and 4 are any amino acid
<220> FEATURE:
<221> NAME/KEY: MISC_FEATURE
<222> LOCATION: (5)..(7)
<223> OTHER INFORMATION: Postion 5-7 are K, N, or H
<220> FEATURE:
<221> NAME/KEY: MISC_FEATURE
<222> LOCATION: (9)..(10)
<223> OTHER INFORMATION: Postion 9-10 are K, N, or S
<220> FEATURE:
<221> NAME/KEY: MISC_FEATURE
<222> LOCATION: (11)..(11)
<223> OTHER INFORMATION: Postion 11 is any amino acid
<220> FEATURE:
<221> NAME/KEY: MISC_FEATURE
<222> LOCATION: (13)..(14)
<223> OTHER INFORMATION: Postion 13-14 is K, N, or S

<400> SEQUENCE: 138

```
Xaa His Xaa Xaa Xaa Xaa Xaa Lys Xaa Xaa Xaa Lys Xaa Xaa Asn Lys
1               5                   10                  15
```

<210> SEQ ID NO 139
<211> LENGTH: 11
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(2)
<223> OTHER INFORMATION: Postion 1-2 is K, N, or H
<220> FEATURE:
<221> NAME/KEY: MISC_FEATURE
<222> LOCATION: (4)..(5)
<223> OTHER INFORMATION: Postion 4-5 is K, N, or S
<220> FEATURE:
<221> NAME/KEY: MISC_FEATURE
<222> LOCATION: (6)..(6)
<223> OTHER INFORMATION: Postion 6 is any amino acid
<220> FEATURE:
<221> NAME/KEY: MISC_FEATURE
<222> LOCATION: (8)..(9)
<223> OTHER INFORMATION: Postion 8-9 are K, N, or S

<400> SEQUENCE: 139

```
Xaa Xaa Lys Xaa Xaa Xaa Lys Xaa Xaa Asn Lys
1               5                   10
```

<210> SEQ ID NO 140
<211> LENGTH: 18
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (2)..(2)
<223> OTHER INFORMATION: Postion 2 is N or E
<220> FEATURE:
<221> NAME/KEY: MISC_FEATURE
<222> LOCATION: (3)..(5)
<223> OTHER INFORMATION: Postion 3-5 is any amino acid
<220> FEATURE:
<221> NAME/KEY: MISC_FEATURE
<222> LOCATION: (6)..(6)
<223> OTHER INFORMATION: Postion 6 is L or I
<220> FEATURE:
<221> NAME/KEY: MISC_FEATURE
<222> LOCATION: (7)..(7)
<223> OTHER INFORMATION: Postion 7 is any amino acid
<220> FEATURE:
<221> NAME/KEY: MISC_FEATURE
<222> LOCATION: (8)..(8)
<223> OTHER INFORMATION: Postion 8 is K, R, or H
<220> FEATURE:

<221> NAME/KEY: MISC_FEATURE
<222> LOCATION: (10)..(12)
<223> OTHER INFORMATION: Position 10-12 is any amino acid
<220> FEATURE:
<221> NAME/KEY: MISC_FEATURE
<222> LOCATION: (13)..(13)
<223> OTHER INFORMATION: Position 13 is L or I
<220> FEATURE:
<221> NAME/KEY: MISC_FEATURE
<222> LOCATION: (14)..(14)
<223> OTHER INFORMATION: Postion 14 is any amino acid
<220> FEATURE:
<221> NAME/KEY: MISC_FEATURE
<222> LOCATION: (16)..(16)
<223> OTHER INFORMATION: Position 16 is D or E
<220> FEATURE:
<221> NAME/KEY: MISC_FEATURE
<222> LOCATION: (17)..(17)
<223> OTHER INFORMATION: Position 17 is N or E

<400> SEQUENCE: 140

Cys Xaa Xaa Xaa Xaa Xaa Xaa Xaa Pro Xaa Xaa Xaa Xaa Xaa Pro Xaa
1               5                   10                  15

Xaa Cys

<210> SEQ ID NO 141
<211> LENGTH: 7
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Position 1 is W, F, or Y
<220> FEATURE:
<221> NAME/KEY: MISC_FEATURE
<222> LOCATION: (2)..(3)
<223> OTHER INFORMATION: Position 2-3 is any amino acid
<220> FEATURE:
<221> NAME/KEY: MISC_FEATURE
<222> LOCATION: (5)..(5)
<223> OTHER INFORMATION: Position 5 is any amino acid
<220> FEATURE:
<221> NAME/KEY: MISC_FEATURE
<222> LOCATION: (6)..(6)
<223> OTHER INFORMATION: Position 6 is S, T, A, or G

<400> SEQUENCE: 141

Xaa Xaa Xaa Phe Xaa Xaa Leu
1               5

<210> SEQ ID NO 142
<211> LENGTH: 7
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Position 1 is L or V
<220> FEATURE:
<221> NAME/KEY: MISC_FEATURE
<222> LOCATION: (2)..(2)
<223> OTHER INFORMATION: Position 2 is any amino acid
<220> FEATURE:
<221> NAME/KEY: MISC_FEATURE
<222> LOCATION: (6)..(6)
<223> OTHER INFORMATION: Position 6 is K or R

<400> SEQUENCE: 142

Xaa Xaa Phe Pro Leu Xaa Gly
1               5

<210> SEQ ID NO 143
<211> LENGTH: 43
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (21)..(22)
<223> OTHER INFORMATION: There is a polymer of 6 aminoundecanoic acid residues between residue 21 and 22
<220> FEATURE:
<221> NAME/KEY: MISC_FEATURE
<222> LOCATION: (43)..(43)
<223> OTHER INFORMATION: Residue 43 is biotinylated

<400> SEQUENCE: 143

```
Ser Ser Gly Gly Val Gly Gly Trp Ala Leu Phe Glu Thr Leu Arg Gly
1               5                   10                  15

Lys Glu Val Ser Arg Tyr Phe Arg Ala Phe Arg Lys Phe Val Lys Pro
            20                  25                  30

Phe Lys Arg Ala Phe Lys Gly Ser Ser Gly Lys
        35                  40
```

<210> SEQ ID NO 144
<211> LENGTH: 43
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (17)..(18)
<223> OTHER INFORMATION: There is a polymer of 6 aminoundecanoic acid residues between residue 17 and 18
<220> FEATURE:
<221> NAME/KEY: MISC_FEATURE
<222> LOCATION: (43)..(43)
<223> OTHER INFORMATION: Residue 43 is biotinylated

<400> SEQUENCE: 144

```
Tyr Phe Arg Ala Phe Arg Lys Phe Val Lys Pro Phe Lys Arg Ala Phe
1               5                   10                  15

Lys Ser Ser Gly Gly Val Gly Gly Trp Ala Leu Phe Glu Thr Leu Arg
            20                  25                  30

Gly Lys Glu Val Ser Arg Gly Ser Ser Gly Lys
        35                  40
```

<210> SEQ ID NO 145
<211> LENGTH: 43
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: There is a polymer of 4 aminoundecanoic acid residues on residue 1
<220> FEATURE:
<221> NAME/KEY: MISC_FEATURE
<222> LOCATION: (19)..(20)
<223> OTHER INFORMATION: There are 2 two 6 unit polyethylene glycol units between resitdues 19 and 20
<220> FEATURE:
<221> NAME/KEY: MISC_FEATURE
<222> LOCATION: (43)..(43)
<223> OTHER INFORMATION: Residue 43 is biotinylated

<400> SEQUENCE: 145

```
Ser Ser Gly Gly Val Gly Gly Trp Ala Leu Phe Glu Thr Leu Arg Gly
1               5                   10                  15

Lys Glu Val Ser Arg Tyr Phe Arg Ala Phe Arg Lys Phe Val Lys Pro
            20                  25                  30

Phe Lys Arg Ala Phe Lys Gly Ser Ser Gly Lys
        35                  40


<210> SEQ ID NO 146
<211> LENGTH: 43
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: There is a myristic acid linked to an
      aminohexanoic acid at amino acid 1
<220> FEATURE:
<221> NAME/KEY: MISC_FEATURE
<222> LOCATION: (21)..(22)
<223> OTHER INFORMATION: There are two 6 unit polyethylene glycol units
      between residues 21 and 22
<220> FEATURE:
<221> NAME/KEY: MISC_FEATURE
<222> LOCATION: (43)..(43)
<223> OTHER INFORMATION: Residue 43 is biotinylated

<400> SEQUENCE: 146

Ser Ser Gly Gly Val Gly Gly Trp Ala Leu Phe Glu Thr Leu Arg Gly
1               5                   10                  15

Lys Glu Val Ser Arg Tyr Phe Arg Ala Phe Arg Lys Phe Val Lys Pro
            20                  25                  30

Phe Lys Arg Ala Phe Lys Gly Ser Ser Gly Lys
        35                  40


<210> SEQ ID NO 147
<211> LENGTH: 43
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (17)..(18)
<223> OTHER INFORMATION: There are two 6 unit polyethylene glycol units
      between residues 17 and 18
<220> FEATURE:
<221> NAME/KEY: MISC_FEATURE
<222> LOCATION: (43)..(43)
<223> OTHER INFORMATION: Amino acid 43 is biotinylated

<400> SEQUENCE: 147

Tyr Phe Arg Ala Phe Arg Lys Phe Val Lys Pro Phe Lys Arg Ala Phe
1               5                   10                  15

Lys Ser Ser Gly Gly Val Gly Gly Trp Ala Leu Phe Glu Thr Leu Arg
            20                  25                  30

Gly Lys Glu Val Ser Arg Gly Ser Ser Gly Lys
        35                  40


<210> SEQ ID NO 148
<211> LENGTH: 43
<212> TYPE: PRT
<213> ORGANISM: Artificial
<220> FEATURE:
<223> OTHER INFORMATION: synthesized
<220> FEATURE:
<221> NAME/KEY: MISC_FEATURE
```

<222> LOCATION: (21)..(22)
<223> OTHER INFORMATION: There are two 6 unit polyethylene glycol units between residues 21 and 22
<220> FEATURE:
<221> NAME/KEY: MISC_FEATURE
<222> LOCATION: (43)..(43)
<223> OTHER INFORMATION: Amino acid 43 is biotinylated

<400> SEQUENCE: 148

```
Ser Ser Gly Gly Val Gly Gly Trp Ala Leu Phe Glu Thr Leu Arg Gly
1               5                   10                  15

Lys Glu Val Ser Arg Tyr Phe Arg Ala Phe Arg Lys Phe Val Lys Pro
            20                  25                  30

Phe Lys Arg Ala Phe Lys Gly Ser Ser Gly Lys
        35                  40
```

<210> SEQ ID NO 149
<211> LENGTH: 43
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (21)..(22)
<223> OTHER INFORMATION: There is one 10 unit polyethylene glycol unit between residues 21 and 22
<220> FEATURE:
<221> NAME/KEY: MISC_FEATURE
<222> LOCATION: (43)..(43)
<223> OTHER INFORMATION: Amino acid 43 is biotinylated

<400> SEQUENCE: 149

```
Ser Ser Gly Gly Val Gly Gly Trp Ala Leu Phe Glu Thr Leu Arg Gly
1               5                   10                  15

Lys Glu Val Ser Arg Tyr Phe Arg Ala Phe Arg Lys Phe Val Lys Pro
            20                  25                  30

Phe Lys Arg Ala Phe Lys Gly Ser Ser Gly Lys
        35                  40
```

<210> SEQ ID NO 150
<211> LENGTH: 46
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (46)..(46)
<223> OTHER INFORMATION: Amino acid 46 is biotinylated

<400> SEQUENCE: 150

```
Ser Trp Trp Gly Phe Trp Asn Gly Ser Ala Ala Pro Val Trp Ser Arg
1               5                   10                  15

Gly Ser Ser Gly Ser Ser Gly Gly Val Gly Gly Trp Ala Leu Phe Glu
            20                  25                  30

Thr Leu Arg Gly Lys Glu Val Ser Arg Gly Ser Ser Gly Lys
        35                  40                  45
```

<210> SEQ ID NO 151
<211> LENGTH: 41
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (41)..(41)

<223> OTHER INFORMATION: Amino acid 41 is biotinylated

<400> SEQUENCE: 151

```
Ser Ser Gly Gly Val Gly Gly Trp Ala Leu Phe Glu Thr Leu Arg Gly
1               5                   10                  15

Lys Glu Val Ser Arg Gly Ser Ser Gly Ser Trp Trp Gly Phe Trp Asn
            20                  25                  30

Gly Ser Ala Ala Pro Val Trp Ser Arg
        35                  40
```

<210> SEQ ID NO 152
<211> LENGTH: 42
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (21)..(22)
<223> OTHER INFORMATION: There are two 6 unit polyethylene glycol units between residues 21 and 22
<220> FEATURE:
<221> NAME/KEY: MISC_FEATURE
<222> LOCATION: (42)..(42)
<223> OTHER INFORMATION: Amino acid 42 is biotinylated

<400> SEQUENCE: 152

```
Ser Ser Gly Gly Val Gly Gly Trp Ala Leu Phe Glu Thr Leu Arg Gly
1               5                   10                  15

Lys Glu Val Ser Arg Ser Trp Trp Gly Phe Trp Asn Gly Ser Ala Ala
            20                  25                  30

Pro Val Trp Ser Arg Gly Ser Ser Gly Lys
        35                  40
```

<210> SEQ ID NO 153
<211> LENGTH: 42
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (21)..(22)
<223> OTHER INFORMATION: There is one 10 unit polyethylene glycol units between residues 21 and 22
<220> FEATURE:
<221> NAME/KEY: MISC_FEATURE
<222> LOCATION: (42)..(42)
<223> OTHER INFORMATION: Amino acid 42 is biotinylated

<400> SEQUENCE: 153

```
Ser Ser Gly Gly Val Gly Gly Trp Ala Leu Phe Glu Thr Leu Arg Gly
1               5                   10                  15

Lys Glu Val Ser Arg Ser Trp Trp Gly Phe Trp Asn Gly Ser Ala Ala
            20                  25                  30

Pro Val Trp Ser Arg Gly Ser Ser Gly Lys
        35                  40
```

<210> SEQ ID NO 154
<211> LENGTH: 42
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (21)..(22)
<223> OTHER INFORMATION: There are 6 poly-aminoundecanoic acid units between residues 21 and 22
<220> FEATURE:
<221> NAME/KEY: MISC_FEATURE
<222> LOCATION: (42)..(42)
<223> OTHER INFORMATION: Amino acid 42 is biotinylated

<400> SEQUENCE: 154

```
Ser Ser Gly Gly Val Gly Gly Trp Ala Leu Phe Glu Thr Leu Arg Gly
1               5                   10                  15

Lys Glu Val Ser Arg Ser Trp Trp Gly Phe Trp Asn Gly Ser Ala Ala
            20                  25                  30

Pro Val Trp Ser Arg Gly Ser Ser Gly Lys
        35                  40
```

<210> SEQ ID NO 155
<211> LENGTH: 47
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (47)..(47)
<223> OTHER INFORMATION: Amino acid 47 is biotinylated

<400> SEQUENCE: 155

```
Ser Ser Gly Gly Val Gly Gly Trp Ala Leu Phe Glu Thr Leu Arg Gly
1               5                   10                  15

Lys Glu Val Ser Arg Gly Ser Ser Gly Tyr Phe Arg Ala Phe Arg Lys
            20                  25                  30

Phe Val Lys Pro Phe Lys Arg Ala Phe Lys Gly Ser Ser Gly Lys
        35                  40                  45
```

<210> SEQ ID NO 156
<211> LENGTH: 37
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (37)..(37)
<223> OTHER INFORMATION: Amino acid 37 is biotinylated

<400> SEQUENCE: 156

```
Arg Arg Arg Arg Arg Arg Arg Pro Ser Ser His Arg Thr Asn His Lys
1               5                   10                  15

Lys Asn Asn Pro Lys Lys Lys Asn Lys Thr Arg Gly Pro Arg Arg Arg
            20                  25                  30

Arg Arg Arg Arg Lys
        35
```

<210> SEQ ID NO 157
<211> LENGTH: 30
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (29)..(30)
<223> OTHER INFORMATION: There are 6 poly-aminoundecanoic acid units between residues 29 and 30
<220> FEATURE:
<221> NAME/KEY: MISC_FEATURE
<222> LOCATION: (30)..(30)
<223> OTHER INFORMATION: Amino acid 30 is biotinylated

<400> SEQUENCE: 157

Arg Arg Arg Arg Arg Arg Arg Pro Ser Ser His Arg Thr Asn His Lys
1 5 10 15

Lys Asn Asn Pro Lys Lys Lys Asn Lys Thr Arg Gly Pro Lys
20 25 30

<210> SEQ ID NO 158
<211> LENGTH: 30
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: There are 6 poly-aminoundecanoic acid units at residue 1
<220> FEATURE:
<221> NAME/KEY: MISC_FEATURE
<222> LOCATION: (30)..(30)
<223> OTHER INFORMATION: Amino acid 30 is biotinylated

<400> SEQUENCE: 158

Pro Ser Ser His Arg Thr Asn His Lys Lys Asn Asn Pro Lys Lys Lys
1 5 10 15

Asn Lys Thr Arg Gly Pro Arg Arg Arg Arg Arg Arg Arg Lys
20 25 30

<210> SEQ ID NO 159
<211> LENGTH: 31
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: There are 6 poly-aminoundecanoic acid units at residue 1
<220> FEATURE:
<221> NAME/KEY: MISC_FEATURE
<222> LOCATION: (31)..(31)
<223> OTHER INFORMATION: Amino acid 31 is biotinylated

<400> SEQUENCE: 159

Ser Ser His Arg Thr Asn His Lys Lys Asn Asn Pro Lys Lys Lys Asn
1 5 10 15

Lys Thr Arg Gly Ser Ser Gly Arg Arg Arg Arg Arg Arg Arg Lys
20 25 30

<210> SEQ ID NO 160
<211> LENGTH: 41
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (7)..(8)
<223> OTHER INFORMATION: There is one 6 unit polyethylene glycol unit between residue 7 and 8
<220> FEATURE:
<221> NAME/KEY: MISC_FEATURE
<222> LOCATION: (24)..(25)
<223> OTHER INFORMATION: There are two 6 unit polyethylene glycol units between residue 24 and 25
<220> FEATURE:
<221> NAME/KEY: MISC_FEATURE
<222> LOCATION: (41)..(41)
<223> OTHER INFORMATION: Amino acid 41 is biotinylated

<400> SEQUENCE: 160

Arg Arg Arg Arg Arg Arg Arg Ser Ser Cys Leu Ile Asp Ile Tyr Gly
1 5 10 15

Val Cys His Asn Phe Asp Ala Tyr His Lys Lys Asn Asn Pro Lys Lys
20 25 30

Lys Asn Lys Thr Arg Gly Ser Ser Lys
35 40

<210> SEQ ID NO 161
<211> LENGTH: 41
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (7)..(8)
<223> OTHER INFORMATION: There is one 6 unit polyethylene glycol unit between residue 7 and 8
<220> FEATURE:
<221> NAME/KEY: MISC_FEATURE
<222> LOCATION: (24)..(25)
<223> OTHER INFORMATION: There is a string of five poly-aminoundecanoic acids between residue 24 and 25
<220> FEATURE:
<221> NAME/KEY: MISC_FEATURE
<222> LOCATION: (41)..(41)
<223> OTHER INFORMATION: Amino acid 41 is biotinylated

<400> SEQUENCE: 161

Arg Arg Arg Arg Arg Arg Arg Ser Ser Cys Leu Ile Asp Ile Tyr Gly
1 5 10 15

Val Cys His Asn Phe Asp Ala Tyr His Lys Lys Asn Asn Pro Lys Lys
20 25 30

Lys Asn Lys Thr Arg Gly Ser Ser Lys
35 40

<210> SEQ ID NO 162
<211> LENGTH: 39
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (17)..(18)
<223> OTHER INFORMATION: There are two 6 unit polyethylene glycol units between residue 17 and 18
<220> FEATURE:
<221> NAME/KEY: MISC_FEATURE
<222> LOCATION: (31)..(32)
<223> OTHER INFORMATION: There is one 6 unit polyethylene glycol unit between residue 31 and 32
<220> FEATURE:
<221> NAME/KEY: MISC_FEATURE
<222> LOCATION: (39)..(39)
<223> OTHER INFORMATION: Amino acid 39 is biotinylated

<400> SEQUENCE: 162

Ser Ser Cys Leu Ile Asp Ile Tyr Gly Val Cys His Asn Phe Asp Ala
1 5 10 15

Tyr His Lys Lys Asn Asn Pro Lys Lys Lys Asn Lys Thr Arg Gly Arg
20 25 30

Arg Arg Arg Arg Arg Arg Lys
35

<210> SEQ ID NO 163
<211> LENGTH: 48

<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (24)..(25)
<223> OTHER INFORMATION: There are two 6 unit polyethylene glycol units between residue 24 and 25
<220> FEATURE:
<221> NAME/KEY: MISC_FEATURE
<222> LOCATION: (48)..(48)
<223> OTHER INFORMATION: Amino acid 48 is biotinylated

<400> SEQUENCE: 163

```
Ser Ser Ser Cys Leu Ile Asp Met Tyr Gly Val Cys His Asn Phe Asp
1               5                   10                  15

Gly Ala Tyr Asp Ser Ser Arg Gly Ser Ser His Arg Thr Asn His Lys
            20                  25                  30

Lys Asn Asn Pro Lys Lys Lys Asn Lys Thr Arg Gly Ser Ser Gly Lys
        35                  40                  45
```

<210> SEQ ID NO 164
<211> LENGTH: 34
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: There is a myristic acid linked to an aminohexanoic acid at residue 1
<220> FEATURE:
<221> NAME/KEY: MISC_FEATURE
<222> LOCATION: (17)..(18)
<223> OTHER INFORMATION: There are two 6 unit polyethylene glycol units between residue 17 and 18
<220> FEATURE:
<221> NAME/KEY: MISC_FEATURE
<222> LOCATION: (34)..(34)
<223> OTHER INFORMATION: Amino acid 34 is biotinylated

<400> SEQUENCE: 164

```
Ser Ser Cys Leu Ile Asp Ile Tyr Gly Val Cys His Asn Phe Asp Ala
1               5                   10                  15

Tyr His Lys Lys Asn Asn Pro Lys Lys Lys Asn Lys Thr Arg Gly Ser
            20                  25                  30

Ser Lys
```

<210> SEQ ID NO 165
<211> LENGTH: 38
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: There is a myristic acid linked to an aminohexanoic acid at residue 1
<220> FEATURE:
<221> NAME/KEY: MISC_FEATURE
<222> LOCATION: (17)..(18)
<223> OTHER INFORMATION: There are two 6 unit polyethylene glycol units between residue 17 and 18
<220> FEATURE:
<221> NAME/KEY: MISC_FEATURE
<222> LOCATION: (38)..(38)
<223> OTHER INFORMATION: Amino acid 38 is biotinylated

<400> SEQUENCE: 165

Ser Ser Cys Leu Ile Asp Ile Tyr Gly Val Cys His Asn Phe Asp Ala
1 5 10 15

Tyr Tyr Phe Arg Ala Phe Arg Lys Phe Val Lys Pro Phe Lys Arg Ala
20 25 30

Phe Lys Gly Ser Ser Lys
35

<210> SEQ ID NO 166
<211> LENGTH: 34
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: There is a pyrene linked to butyric at residue 1
<220> FEATURE:
<221> NAME/KEY: MISC_FEATURE
<222> LOCATION: (17)..(18)
<223> OTHER INFORMATION: There are two 6 unit polyethylene glycol units between residue 17 and 18
<220> FEATURE:
<221> NAME/KEY: MISC_FEATURE
<222> LOCATION: (34)..(34)
<223> OTHER INFORMATION: Amino acid 34 is biotinylated

<400> SEQUENCE: 166

Ser Ser Cys Leu Ile Asp Ile Tyr Gly Val Cys His Asn Phe Asp Ala
1 5 10 15

Tyr His Lys Lys Asn Asn Pro Lys Lys Lys Asn Lys Thr Arg Gly Ser
20 25 30

Ser Lys

<210> SEQ ID NO 167
<211> LENGTH: 23
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (17)..(18)
<223> OTHER INFORMATION: There is a 6 unit polyethylene glycol unit between residue 17 and 18

<400> SEQUENCE: 167

Ser Ser Cys Leu Ile Asp Ile Tyr Gly Val Cys His Asn Phe Asp Ala
1 5 10 15

Tyr Asp Asp Asp Asp Asp Asp
20

<210> SEQ ID NO 168
<211> LENGTH: 23
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (6)..(7)
<223> OTHER INFORMATION: There is a 6 unit polyethylene glycol unit between residue 6 and 7

<400> SEQUENCE: 168

Glu Glu Glu Glu Glu Glu Ser Ser Cys Leu Ile Asp Ile Tyr Gly Val
1 5 10 15

```
Cys His Asn Phe Asp Ala Tyr
            20


<210> SEQ ID NO 169
<211> LENGTH: 29
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (6)..(7)
<223> OTHER INFORMATION: There is a 6 unit polyethylene glycol unit
      between residue 6 and 7
<220> FEATURE:
<221> NAME/KEY: MISC_FEATURE
<222> LOCATION: (23)..(24)
<223> OTHER INFORMATION: There is a 6 unit polyethylene glycol unit
      between residue 23 and 24

<400> SEQUENCE: 169

Glu Glu Glu Glu Glu Glu Ser Ser Cys Leu Ile Asp Ile Tyr Gly Val
1               5                   10                  15

Cys His Asn Phe Asp Ala Tyr Glu Glu Glu Glu Glu Glu
            20                  25


<210> SEQ ID NO 170
<211> LENGTH: 9
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (6)..(7)
<223> OTHER INFORMATION: There is a 6 unit polyethylene glycol unit
      between residue 6 and 7
<220> FEATURE:
<221> NAME/KEY: MISC_FEATURE
<222> LOCATION: (8)..(9)
<223> OTHER INFORMATION: The alanine residues at positions 8 and 9 are
      D-alanine

<400> SEQUENCE: 170

Asp Asp Asp Asp Asp Asp Lys Ala Ala
1               5


<210> SEQ ID NO 171
<211> LENGTH: 39
<212> TYPE: PRT
<213> ORGANISM: Artificial
<220> FEATURE:
<223> OTHER INFORMATION: synthesized

<400> SEQUENCE: 171

Glu Glu Glu Glu Glu Glu Glu Pro Ser Ser Cys Leu Ile Asp Ile Tyr
1               5                   10                  15

Gly Val Cys His Asn Phe Asp Gly Ala Tyr Asp Ser Ser Arg Gly Pro
            20                  25                  30

Glu Glu Glu Glu Glu Glu Glu
        35


<210> SEQ ID NO 172
<211> LENGTH: 23
<212> TYPE: PRT
<213> ORGANISM: Artificial
<220> FEATURE:
<223> OTHER INFORMATION: synthesized
<220> FEATURE:
```

```
<221> NAME/KEY: MISC_FEATURE
<222> LOCATION: (17)..(18)
<223> OTHER INFORMATION: There is a 6 unit polyethylene glycol unit
      between residue 17 and 18

<400> SEQUENCE: 172

Ser Ser Cys Leu Ile Asp Ile Tyr Gly Val Cys His Asn Phe Asp Ala
1               5                   10                  15

Tyr Asp Glu Asp Glu Asp Glu
            20


<210> SEQ ID NO 173
<211> LENGTH: 39
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (17)..(18)
<223> OTHER INFORMATION: There are two 6 unit polyethylene glycol units
      between residue 17 and 18
<220> FEATURE:
<221> NAME/KEY: MISC_FEATURE
<222> LOCATION: (31)..(32)
<223> OTHER INFORMATION: There are two 6 unit polyethylene glycol units
      between residue 31 and 32
<220> FEATURE:
<221> NAME/KEY: MISC_FEATURE
<222> LOCATION: (39)..(39)
<223> OTHER INFORMATION: Amino acid 39 is biotinylated

<400> SEQUENCE: 173

Ser Ser Cys Leu Ile Asp Ile Tyr Gly Val Cys His Asn Phe Asp Ala
1               5                   10                  15

Tyr His Lys Lys Asn Asn Pro Lys Lys Lys Asn Lys Thr Arg Gly Arg
            20                  25                  30

Arg Arg Arg Arg Arg Arg Lys
        35


<210> SEQ ID NO 174
<211> LENGTH: 31
<212> TYPE: PRT
<213> ORGANISM: Artificial
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: There are 6 poly-aminoundecanoic acid units at
      residue 1
<220> FEATURE:
<221> NAME/KEY: MISC_FEATURE
<222> LOCATION: (31)..(31)
<223> OTHER INFORMATION: Amino acid 31 is biotinylated

<400> SEQUENCE: 174

Ser Ser His Arg Thr Asn His Lys Lys Asn Asn Pro Lys Lys Lys Asn
1               5                   10                  15

Lys Thr Arg Gly Ser Ser Gly Lys Arg Arg Arg Arg Arg Arg Arg
            20                  25                  30


<210> SEQ ID NO 175
<211> LENGTH: 38
<212> TYPE: PRT
<213> ORGANISM: Artificial
<220> FEATURE:
<223> OTHER INFORMATION: Synthesized
<220> FEATURE:
<221> NAME/KEY: MISC_FEATURE
```

<222> LOCATION: (38)..(38)
<223> OTHER INFORMATION: Amino acid 38 is biotinylated

<400> SEQUENCE: 175

Cys Arg Arg Arg Arg Arg Arg Arg Pro Ser Ser His Arg Thr Asn His
1 5 10 15

Lys Lys Asn Asn Pro Lys Lys Lys Asn Lys Thr Arg Gly Pro Arg Arg
20 25 30

Arg Arg Arg Arg Arg Lys
35

<210> SEQ ID NO 176
<211> LENGTH: 23
<212> TYPE: PRT
<213> ORGANISM: Artificial
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: There is a maleoyl-propionic acid at residue 1

<400> SEQUENCE: 176

Ser Ser Cys Leu Ile Asp Ile Tyr Gly Val Cys His Asn Phe Asp Ala
1 5 10 15

Tyr Asp Asp Asp Asp Asp Asp
20

<210> SEQ ID NO 177
<211> LENGTH: 13
<212> TYPE: PRT
<213> ORGANISM: Artificial
<220> FEATURE:
<223> OTHER INFORMATION: Synthesized
<220> FEATURE:
<221> NAME/KEY: MISC_FEATURE
<222> LOCATION: (1)..(2)
<223> OTHER INFORMATION: Positions 1-2 are F, W, or Y
<220> FEATURE:
<221> NAME/KEY: MISC_FEATURE
<222> LOCATION: (3)..(3)
<223> OTHER INFORMATION: Position 3 is any amino acid
<220> FEATURE:
<221> NAME/KEY: MISC_FEATURE
<222> LOCATION: (4)..(5)
<223> OTHER INFORMATION: Positions 4-5 are F, W, or Y
<220> FEATURE:
<221> NAME/KEY: MISC_FEATURE
<222> LOCATION: (6)..(12)
<223> OTHER INFORMATION: Positions 6-12 are any amino acid
<220> FEATURE:
<221> NAME/KEY: MISC_FEATURE
<222> LOCATION: (13)..(13)
<223> OTHER INFORMATION: Position 13 is F, W, or Y

<400> SEQUENCE: 177

Xaa Xaa Xaa Xaa Xaa Xaa Xaa Xaa Xaa Xaa Xaa Xaa Xaa
1 5 10

<210> SEQ ID NO 178
<211> LENGTH: 12
<212> TYPE: PRT
<213> ORGANISM: Artificial
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Position 1 is F, W, or Y
<220> FEATURE:
<221> NAME/KEY: MISC_FEATURE -continued

```
<222> LOCATION: (2)..(3)
<223> OTHER INFORMATION: Positions 2-3 are any amino acid
<220> FEATURE:
<221> NAME/KEY: MISC_FEATURE
<222> LOCATION: (4)..(6)
<223> OTHER INFORMATION: Positions 4-6 are F, W, or Y
<220> FEATURE:
<221> NAME/KEY: MISC_FEATURE
<222> LOCATION: (7)..(12)
<223> OTHER INFORMATION: Positions 7-12 are any amino acid

<400> SEQUENCE: 178

Xaa Xaa Xaa Xaa Xaa Xaa Xaa Xaa Xaa Xaa Xaa Xaa
1               5                   10
```